United States Patent
Lifton et al.

(10) Patent No.: US 9,732,138 B2
(45) Date of Patent: Aug. 15, 2017

(54) LOSS OF FUNCTION MUTATIONS IN KCNJ10 CAUSE SESAME, A HUMAN SYNDROME WITH SENSORY, NEUROLOGICAL, AND RENAL DEFICITS

(75) Inventors: Richard P. Lifton, North Haven, CT (US); Ute Scholl, Aachen (DE)

(73) Assignee: Yale University, New Haven, CT (US)

(*) Notice: Subject to any disclaimer, the term of this patent is extended or adjusted under 35 U.S.C. 154(b) by 1124 days.

(21) Appl. No.: 13/024,084

(22) Filed: Feb. 9, 2011

(65) Prior Publication Data
US 2011/0195863 A1    Aug. 11, 2011

Related U.S. Application Data

(60) Provisional application No. 61/302,865, filed on Feb. 9, 2010.

(51) Int. Cl.
| | |
|---|---|
| C12P 21/06 | (2006.01) |
| C07K 14/705 | (2006.01) |
| C12Q 1/68 | (2006.01) |
| G01N 33/68 | (2006.01) |

(52) U.S. Cl.
CPC .......... *C07K 14/705* (2013.01); *C12Q 1/6883* (2013.01); *G01N 33/6872* (2013.01); *C12Q 2600/118* (2013.01); *G01N 2500/10* (2013.01); *Y10T 436/143333* (2015.01)

(58) Field of Classification Search
CPC .............................. C07K 14/705; C07K 1/6883
See application file for complete search history.

(56) References Cited

U.S. PATENT DOCUMENTS

| | | |
|---|---|---|
| 7,262,290 B2 | 8/2007 | Berrettini |
| 2003/0104457 A1* | 6/2003 | Harris et al. ............ 435/6 |

OTHER PUBLICATIONS

NCBI potassium inwardly-rectifying channel, subfamily J, member 10, May 2008.*
Nollau et al., Methods for detection of point mutations: performance and quality assessment, Clinical Chemistry 43:7 1114-1128 (1997).*
Buono, et al., "Association between variation in the human *KCNJ10* potassium ion channel gene and seizure susceptibility," *Epilepsy Research*, 2004, 58:175-183.
Djukic, et al., "Conditional Knock-Out of $K_{ir}4.1$ Leads to Glial Membrane Depolarization, Inhibition of Potassium and Glutamate Uptake, and Enhanced Short-Term Synaptic Potentiation," *The Journal of Neuroscience*, Oct. 17, 2007, 27(42):11354-11365.
Ji, et al., "Rare independent mutations in renal salt handling genes contribute to blood pressure variation," *Nature Genetics*, May 2008, 40(5):592-599.

(Continued)

*Primary Examiner* — Reza Ghafoorian
(74) *Attorney, Agent, or Firm* — Saul Ewing LLP; Kathryn Doyle; Domingos J. Silva

(57) ABSTRACT

The invention includes a method of identifying a human subject at-risk of developing SeSAME syndrome. The invention also includes a method of diagnosing a human subject afflicted with SeSAME syndrome. The invention further includes a method of identifying a therapeutic agent that modulates a given KCNJ10 mediated $K^+$ current in a mammalian cell. The invention also includes a method of diagnosing a subject as a carrier of SeSAME syndrome.

8 Claims, 4 Drawing Sheets

(56) References Cited

OTHER PUBLICATIONS

Lopes, et al., "Alterations in Conserved Kir Channel-PIP$_2$ Interactions Underlie Channelopathies," *Neuron*, Jun. 13, 2002, 34:933-944.
Neusch, et al., "Kir4.1 Potassium Channel Subunit is Crucial for Oligodendrocyte Development and In Vivo Myelination," *The Journal of Neuroscience*, Aug. 1, 2001, 21(15):5429-5438.
Nishida, et al., "Crystal structure of a Kir3.1-prokaryotic Kir channel chimera," *The EMBO Journal*, 2007, 26(17):4005-4015.
Tanemoto, et al., "PDZ binding motif-dependent localization of K+ channel on the basolateral side in distal tubules," *Am J Physiol Renal Physiol*, 2004, 287:F1148-F1153.
Rapedius, et al., "Control of pH and PIP$_2$ Gating in Heteromeric Kir4.1/Kir5.1 Channels by H-Bonding at the Helix-Bundle Crossing," *Channels*, 2007, 1(5):327-330.
Rozengurt, et al., "Time course of inner ear degeneration and deafness in mice lacking the Kir4.1 potassium channel subunit," *Hearing Research*, 2003, 177:71-80.
Scholl, et al., "Seizures, sensorineural deafness, ataxia, mental retardation, and electrolyte imbalance (SeSAME syndrome) caused by mutations in *KCNJ10*," *PNAS*, Apr. 7, 2009, 106(14):5842-5847.
Schulte, et al., "pH-dependent Gating of ROMK (K$_{ir}$1.1) Channels Involves Conformational Changes in Both N and C Termini," *The Journal of Biological Chemistry*, Dec. 18, 1998, 273(50:34575-34579.

\* cited by examiner

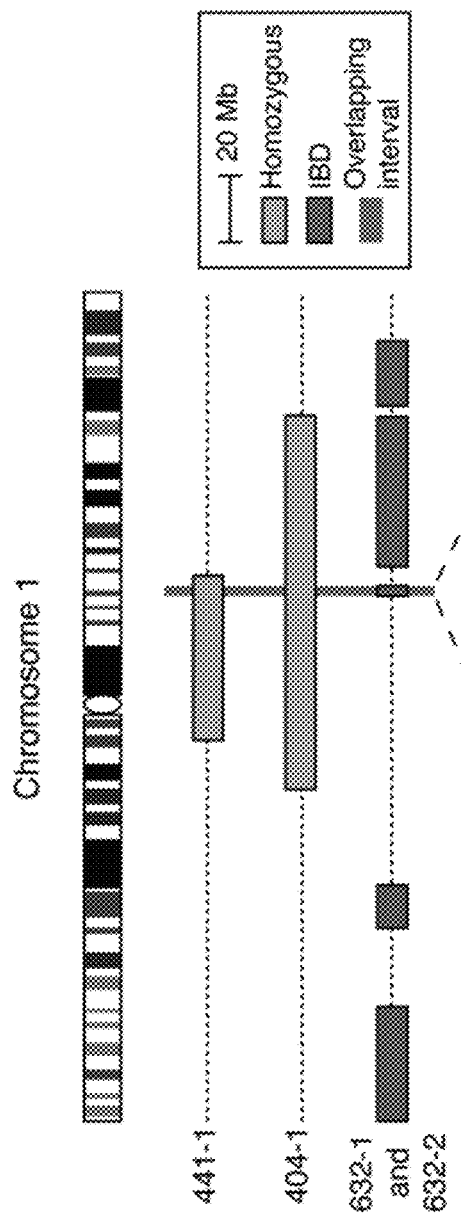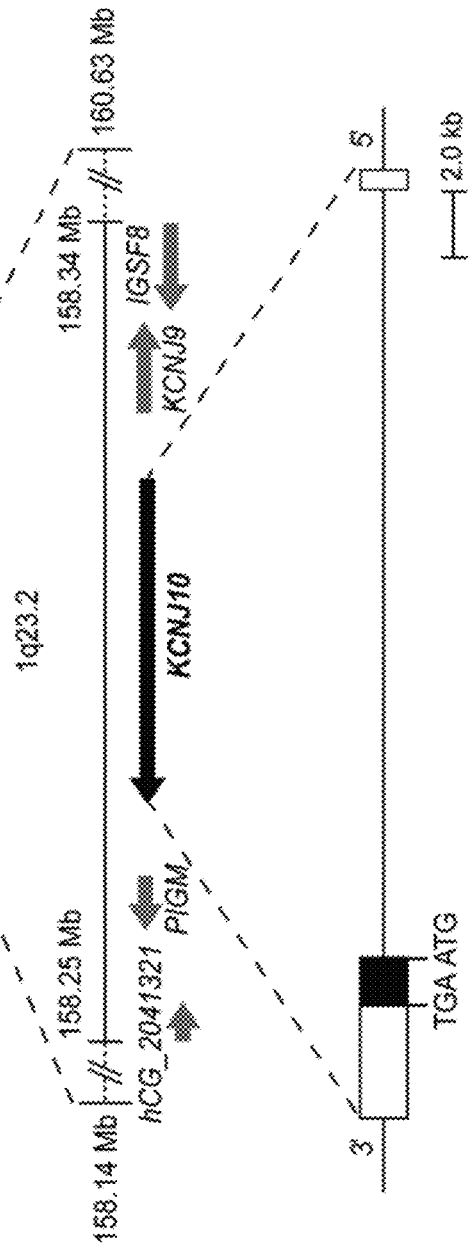

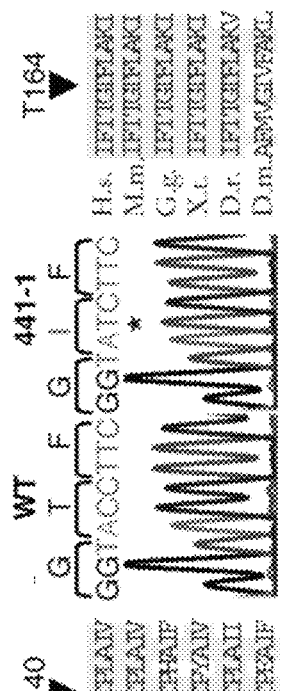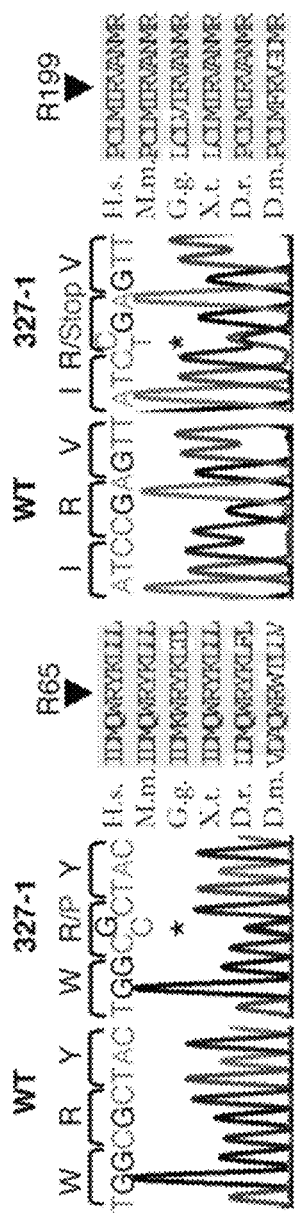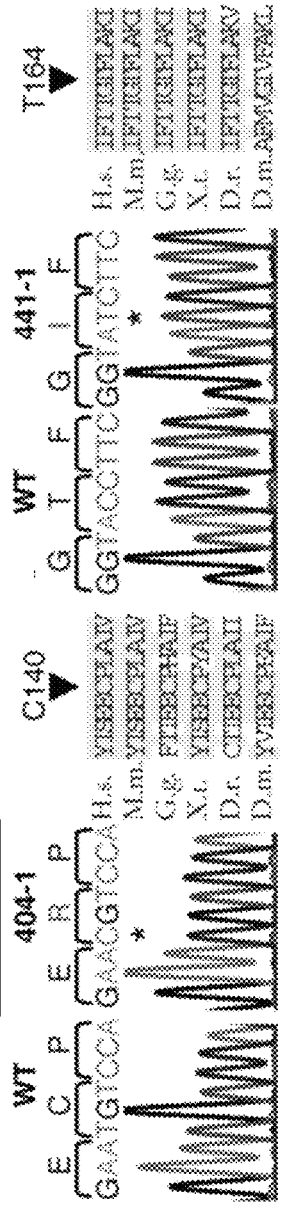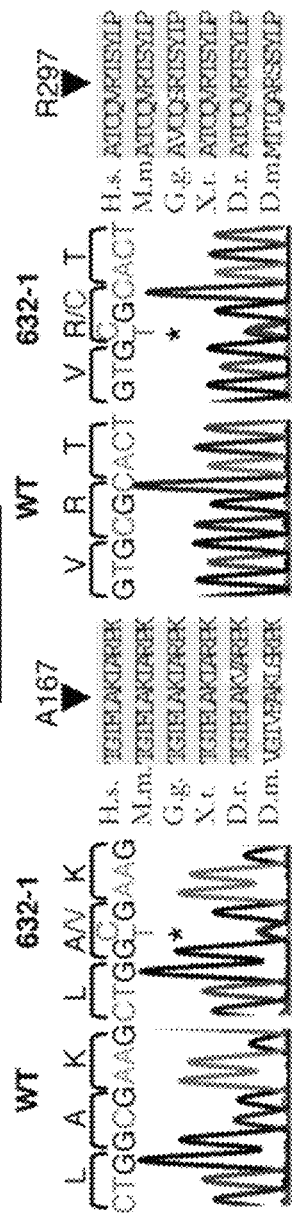
Figure 2A
Figure 2B
Figure 2C
Figure 2D

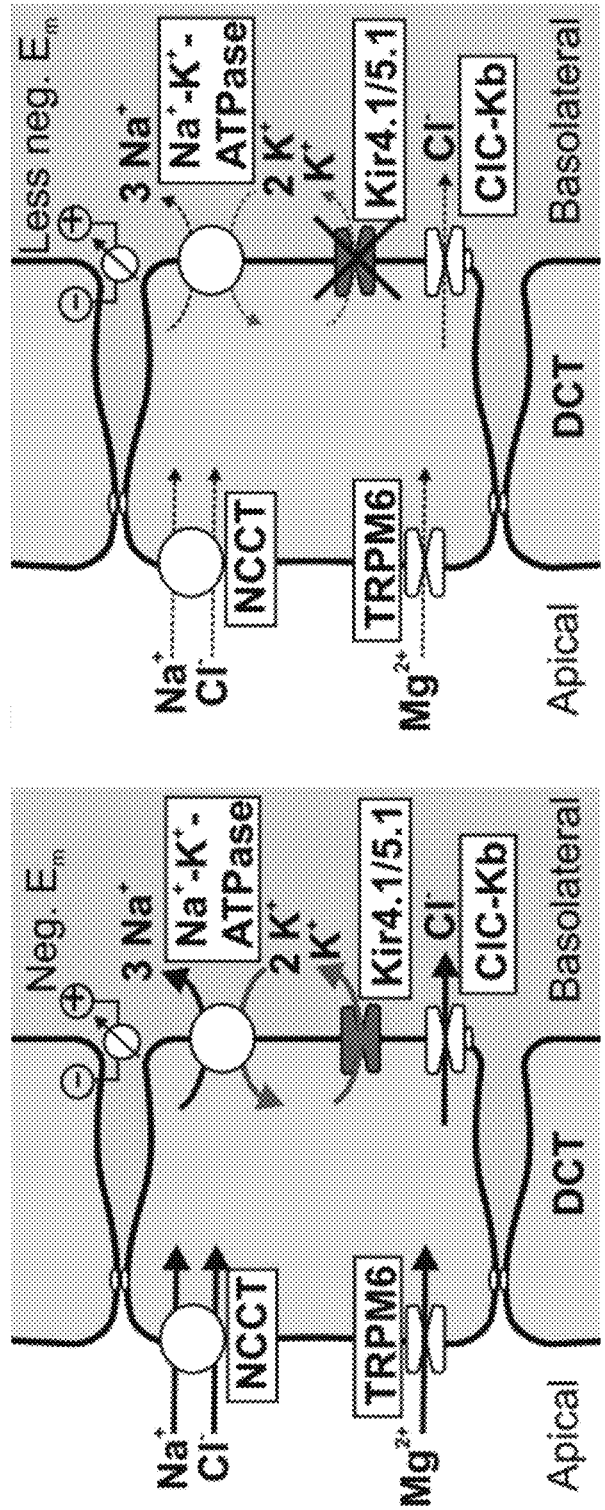

LOSS OF FUNCTION MUTATIONS IN KCNJ10 CAUSE SESAME, A HUMAN SYNDROME WITH SENSORY, NEUROLOGICAL, AND RENAL DEFICITS

CROSS REFERENCE TO RELATED APPLICATIONS

The present application is entitled to priority under 35 U.S.C. §119(e) to U.S. Provisional Application No. 61/302,865, filed Feb. 9, 2010, which application is hereby incorporated by reference herein in its entirety.

BACKGROUND OF THE INVENTION

Transmembrane ion flux via channels, transporters, and pumps plays a critical role in diverse physiologic functions, including neuronal signal transmission and electrolyte and volume homeostasis. In many cases, homologous electrolyte flux processes in different tissues are mediated by the encoded products of distinct genes, while in a few cases the identical gene products are involved. Evidence of the latter comes from Mendelian diseases in which mutation in a single gene produces effects on both auditory and renal function. For example, loss-of-function mutations in ATP6B1, which encodes a subunit of the $H^+$-ATPase, result in systemic acidosis because of a renal defect in $H^+$ secretion and sensorineural hearing loss caused by defective $H^+$ secretion into the cochlear endolymph, resulting in impaired hair cell function and deafness (Karet et al., 1999, Nature Genetics 21:84-90). Similarly, mutations in barttin, an accessory subunit of the CLCNKA and CLCNKB chloride channels, result in renal salt wasting and deafness (Birkenhager et al., 2001, Nature Genetics 29:310-314).

The genetic dissection of renal diseases featuring low serum potassium (hypokalemia) and metabolic alkalosis (high serum pH) has identified many components required for normal renal electrolyte homeostasis (Birkenhager et al., 2001, Nature Genetics 29:310-314; Hansson et al., 1995, Nature Genetics 11:76-82; Simon et al., 1997, Nature Genetics 17:171-178; Simon et al., 1996, Nature Genetics 13:183-188; Simon et al., 1996, Nature Genetics 14:152-156; Simon et al., 1996, Nature Genetics 12:24-30). In all cases, this syndrome has resulted from increased activity of the epithelial $Na^+$ channel (ENaC) on the apical membrane, which leads to increased secretion of $K^+$ and $H^+$ because of the more negative luminal potential. Hypokalemia with alkalosis can result either from primary increases in ENaC activity because of mutations in ENaC itself (Hansson et al., 1995, Nature Genetics 11:76-82), or from activation of ENaC by aldosterone in response to reduced intravascular volume (Simon et al., 1996, Nature Genetics 12:24-30). Mutations that cause impaired salt reabsorption in the thick ascending limb of Henle or the distal convoluted tubule cause salt wasting that leads to secondary increases in ENaC activity and hypokalemic alkalosis. These diseases, referred to as Bartter and Gitelman syndromes, are associated with mutations in genes encoding apical $Na^+$—$Cl^-$ transporters that mediate $Na^+$—$Cl^-$ entry into epithelia, $Cl^-$ channel subunits that mediate exit of $Cl^-$ across the basolateral membrane, and an apical $K^+$ channel (Birkenhager et al., 2001, Nature Genetics 29:310-314; Simon et al., 1997, Nature genetics 17:171-178; Simon et al., 1996, Nature genetics 13:183-188; Simon et al., 1996, Nature Genetics 14:152-156; Simon et al., 1996, Nature Genetics 12:24-30). These syndromes are distinguished clinically by marked hypomagnesemia and low urinary calcium in Gitelman syndrome, while hypercalciuria with normal or modest reductions in $Mg^{2+}$ is observed in Bartter syndrome.

Similarly, a number of Mendelian seizure disorders have been described. Many of these result from mutations that depolarize neurons, increasing neuronal excitability and reducing seizure threshold. Examples include benign familial neonatal seizures caused by mutations in the KCNQ2/3 $K^+$ channels (Biervert et al., 1998, Science 279:403-406; Charlier et al., 1998, Nature Genetics 18:53-55), benign familial neonatal/infantile seizures caused by mutations in the SCN2A gene encoding the alpha subunit of voltage gated $Na^+$ channels (Heron et al., 2002, Lancet 360:851-852), and several idiopathic epilepsy syndromes caused by mutations in the SCN1A sodium channel (Weber et al., 2008, Dev. Med. Child. Neurol. 50:648-654).

Considering the many similarities in the mechanisms governing renal electrolyte homeostasis and neuronal function, it is surprising that relatively few single-gene disorders that have effects on both have been identified. Here, we describe a previously unrecognized complex syndrome featuring seizures, sensorineural deafness, ataxia, mental retardation and electrolyte imbalance (SeSAME), and demonstrate that it is caused by mutation in KCNJ10, which encodes a $K^+$ channel expressed in epithelia of the kidney and inner ear, as well as glial cells in the CNS.

There is need in the art for compositions and methods to diagnose and treat subjects afflicted with SeSAME syndrome. The present invention fulfills this need.

BRIEF SUMMARY OF THE INVENTION

The invention includes a composition comprising an isolated nucleic acid selected from the group consisting of SEQ ID NO:3-8 and a fragment thereof.

The invention also includes a composition comprising an isolated nucleic acid complementary to a sequence selected from the group consisting of SEQ ID NO:3-8 and a fragment thereof.

The invention further includes a recombinant cell comprising an isolated nucleic acid, wherein the nucleic acid is selected from the group consisting of SEQ ID NO:3-8 and a fragment thereof.

The invention also includes a composition comprising an expression vector comprising an isolated nucleic acid selected from the group consisting of SEQ ID NO:3-8 and a fragment thereof.

The invention further includes a composition comprising an expression vector comprising an isolated nucleic acid, wherein the nucleic acid is complementary to a sequence selected from the group consisting of SEQ ID NO:3-8 and a fragment thereof.

The invention also includes a composition comprising an isolated polypeptide comprising an amino acid sequence selected from the group consisting of SEQ ID NO:9, SEQ ID NO:10, SEQ ID NO:11, SEQ ID NO:12, SEQ ID NO:13, SEQ ID NO:14 and a fragment thereof.

The invention further includes a method of identifying a human subject at-risk of developing SeSAME syndrome. The method comprises the step of obtaining a bodily sample from the subject. The method further comprises the step of assaying the sample for the presence of at least one mutation in the KCNJ10 gene or at least one disrupted KCNJ10 gene product in the sample, wherein, if the at least one mutation or disrupted gene product is present in the sample, then the subject is at-risk of developing the SeSAME syndrome.

In one embodiment, the bodily sample is selected from the group consisting of a tissue, a cell and a bodily fluid. In another embodiment, the bodily fluid comprises maternal serum or amniotic fluid. In yet another embodiment, the assaying comprises a method selected from the group consisting of a PCR assay, a sequencing assay, a probe array assay, a gene chip assay, a microarray assay, a Northern blot assay, an in situ hybridization assay, and a RT-PCR assay. In yet another embodiment, the assaying comprises evaluating a nucleic acid in the sample for at least one mutation or at least one gene product disruption, wherein the nucleic acid comprises a sequence selected from the group consisting of SEQ ID NO:1, SEQ ID NO:3-8, a complementary sequence thereof, and a fragment thereof. In yet another embodiment, the assaying comprises evaluating the sample for a protein comprising an amino acid sequence selected from the group consisting of SEQ ID NO:2, SEQ ID NO:9, SEQ ID NO:10, SEQ ID NO:11, SEQ ID NO.12, SEQ ID NO:13, SEQ ID NO:14 and a fragment thereof. In yet another embodiment, the evaluating comprises a method selected from the group consisting of a Western blot assay, a radioimmunoassay (RIA), an immunoassay, chemiluminescent assay, and an enzyme-linked immunosorbent assay (ELISA). In yet another embodiment, the at least one mutation or disrupted gene product is derived from a process selected from the group consisting of a nonsense mutation, a missense mutation, a truncated coding mRNA, a change in protein sequence, and a truncated protein. In yet another embodiment, the at least one mutation comprises a mutation selected from the group consisting of a homozygous missense mutation, a compound heterozygous missense mutation, a homozygous nonsense mutation, a compound heterozygous mutation, and a compound heterozygous missense/nonsense mutation.

The invention further includes a method of diagnosing a human subject afflicted with SeSAME syndrome. The method comprises the step of obtaining a bodily sample from the subject. The method further comprises the step of assaying the sample for the presence of at least one mutation in the KCNJ10 gene or at least one disrupted KCNJ10 gene product in the sample, wherein, if the at least one mutation or disrupted gene product is present in the sample, then the subject is diagnosed as being afflicted with SeSAME syndrome.

In one embodiment, the bodily sample is selected from the group consisting of a tissue, a cell, and a bodily fluid. In another embodiment, the assaying comprises a method selected from the group consisting of a PCR assay, a sequencing assay, a probe array assay, a gene chip assay, a microarray assay, a Northern blot assay, an in situ hybridization assay, and an RT-PCR assay. In yet another embodiment, the assaying comprises evaluating a nucleic acid in the sample for at least one mutation or gene product disruption, wherein the nucleic acid is selected from the group consisting of SEQ ID NO:1, SEQ ID NO:3-8, a complementary sequence thereof and a fragment thereof. In yet another embodiment, the assaying comprises evaluating the sample for a protein comprising an amino acid sequence selected from the group consisting of SEQ ID NO:2, SEQ ID NO:9, SEQ ID NO:10, SEQ ID NO:11, SEQ ID NO:12, SEQ ID NO:13, SEQ ID NO:14, and a fragment thereof. In yet another embodiment, the evaluating comprises a method selected from the group consisting of a Western blot assay, a radioimmunoassay (RIA), an immunoassay, a chemiluminescent assay, and an enzyme-linked immunosorbent assay (ELISA). In yet another embodiment, the at least one mutation or disrupted gene product is derived from a process selected from the group consisting of a nonsense mutation, a missense mutation, a truncated coding mRNA, a change in protein sequence, and a truncated protein. In yet another embodiment, the at least one mutation comprises a mutation selected from the group consisting of a homozygous missense mutation, a compound heterozygous missense mutation, a homozygous nonsense mutation, a compound heterozygous mutation, and a compound heterozygous missense/nonsense mutation.

The invention also includes a method of identifying a therapeutic agent that modulates a given KCNJ10 mediated $K^+$ current in a mammalian cell. The method comprises the step of (a) placing the cell expressing the given KCNJ10 protein into a bathing solution to measure current. The method further comprises the step of (b) measuring an induced $K^+$ current in the cell of step (a). The method further comprises the step of (c) adding a compound to the bathing solution of step (a). The method further comprises the step of (d) measuring an induced $K^+$ current in the cell of step (c). The method further comprises the step of (e) determining whether the compound resulted in an induced $K^+$ current in step (d) which differs from the induced $K^+$ current measured in step (b), wherein, when a compound results in the induced currents of steps (b) and (d) differing from each other, said compound is identified as the therapeutic agent that modulates the given KCNJ10 mediated $K^+$ current in the mammalian cell, wherein the given KCNJ10 is wild-type KCNJ10 or mutant KCNJ10.

In one embodiment, the mutant KCNJ10 comprises a mutation selected from the group consisting SEQ ID NO:9, SEQ ID NO:10, SEQ ID NO:11, SEQ ID NO:12, SEQ ID NO:13, SEQ ID NO:14 and a fragment thereof.

The invention further includes a method of diagnosing a subject as a carrier of SeSAME syndrome, wherein the subject is capable of contributing to an increase in the risk of offspring of the subject to develop SeSAME syndrome. The method comprises the step of obtaining a bodily sample from the subject. The method further comprises the step of assaying the sample for the presence of at least one mutation in the KCNJ10 gene or at least one disruption in a KCNJ10 gene product in the sample, wherein, if the at least one mutation or gene product disruption is present in the sample, then the subject is diagnosed as a SeSAME syndrome carrier, whereby the subject is capable of contributing to an increase in the risk of offspring of the subject to develop SeSAME syndrome.

In one embodiment, the subject is a parent of offspring previously diagnosed with SESAME syndrome. In another embodiment, the subject is an expecting parent. In yet another embodiment, the bodily sample is selected from the group consisting of a tissue, a cell and a bodily fluid. In yet another embodiment, the assaying comprises a method selected from the group consisting of a PCR assay, a sequencing assay, a probe array assay, a gene chip assay, a microarray assay, a Northern blot assay, an in situ hybridization assay, and an RT-PCR assay. In yet another embodiment, the assaying comprises evaluating a nucleic acid in the sample for at least one mutation or one gene product disruption, wherein the nucleic acid is selected from the group consisting of SEQ ID NO:1, SEQ ID NO:3-8, a complementary sequence thereof, and a fragment thereof. In yet another embodiment, the assaying comprises evaluating the sample for a protein comprising an amino acid sequence selected from the group consisting of SEQ ID NO:2, SEQ ID NO:9-14, and a fragment thereof. In yet another embodiment, the at least one mutation or disrupted gene product is derived from a process selected from the group consisting of a nonsense mutation, a missense mutation, a truncated coding mRNA, a change in protein sequence, and a truncated protein. In yet another embodiment, the at least one mutation comprises a mutation selected from the group consisting of a homozygous missense mutation, a compound heterozygous missense mutation, a homozygous nonsense mutation, a compound heterozygous mutation, and a compound heterozygous missense/nonsense mutation.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIGS. 1A-1B are schematic illustrations depicting mapping the disease locus. FIG. 1A depicts an ideogram of chromosome 1 with homozygous regions in patient 441-1 and 404-1 indicated by light gray boxes, and segments that are identical by descent (IBD) in the siblings 632-1 and 632-2 marked by dark gray boxes. The overlap of these intervals is marked, and represents the maximum likelihood location of the disease locus on chromosome 1q23.2-q23.3, a 4-cM interval covering 2.5 Mb from 158.1M to 160.6Mbase pairs. FIG. 1B depicts the candidate interval that contains KCNJ10 on chromosome 1q23.2. Neighboring genes are represented by arrows in their corresponding transcriptional orientations. KCNJ10 comprises 2 exons indicated by boxes, with the coding sequence indicated in black.

FIGS. 2A-2D are schematic illustrations depicting mutations in KCNJ10 in affected patients. In each panel the DNA sequences of the sense strand of wild-type subjects (Left) and affected subjects (Right) are shown. The sequence of the encoded peptide is indicated in single letter code. A Clustal W alignment of the *Homo sapiens* (H.s.) protein sequence with orthologs and paralogs from *Mus musculus* (M.m.), *Gallus gallus* (G.g.), *Xenopus tropicalis* (X.t.), *Danio rerio* (D.r.), and *Drosophila melanogaster* (D.m.) is shown next to each mutation. The human sequence and residues conserved in orthologs and paralogs are marked in yellow, and the mutant residue is indicated. FIG. 2A depicts the results for patient 327-1 and shows that this patient is compound heterozygous for a missense and a nonsense mutation in KCNJ10. FIG. 2B depicts the results for patient 404-1 and shows that this patient is homozygous for a missense mutation, changing codon TGT (C140) to CGT (R140). FIG. 2C depicts a homozygous missense mutation found in kindred 441, resulting in change of codon ACC (T164) to ATC (I164). FIG. 2D depicts the results for kindred 632, in which both affected siblings are compound heterozygous for missense mutations: A167V and R297C.

FIGS. 4A-4B are schematic illustrations of a model of impaired ion transport in the distal convoluted tubule caused by mutations in the Kir4.1 inwardly rectifying potassium channel. FIG. 4A depicts Kir4.1/5.1 heteromultimers in the basolateral membrane of the distal convoluted tubule (DCT). The channels recycle potassium entering the cell via the $Na^+$—$K^+$-ATPase back into the interstitial space and contribute to the negative membrane potential that promotes basolateral chloride exit. On the luminal surface, sodium and chloride enter the cell via the thiazide sensitive cotransporter NCCT, and $Mg^{2+}$ enters via TrpM6, using the favorable electrical gradient. FIG. 4B depicts how disruption of Kir4.1 function inhibits the function of the $Na^+$—$K^+$-ATPase via loss of potassium recycling, reduces basolateral chloride reabsorption by rendering the membrane potential (Em) less negative, and thereby inhibits both apical $Na^+$ and $Cl^-$ reabsorption by NCCT and $Mg^{2+}$ reabsorption because of a less negative membrane potential. The resulting renal salt loss activates the renin-angiotensin-aldosterone system. Increased amounts of $Na^+$ and $Cl^-$ are delivered to the cortical collecting duct, where aldosterone dependent $Na^+$ reabsorption via ENaC is coupled to $K^+$ and $H^+$ secretion, thus accounting for the hypokalemic alkalosis observed.

DETAILED DESCRIPTION OF THE INVENTION

Figure 3:
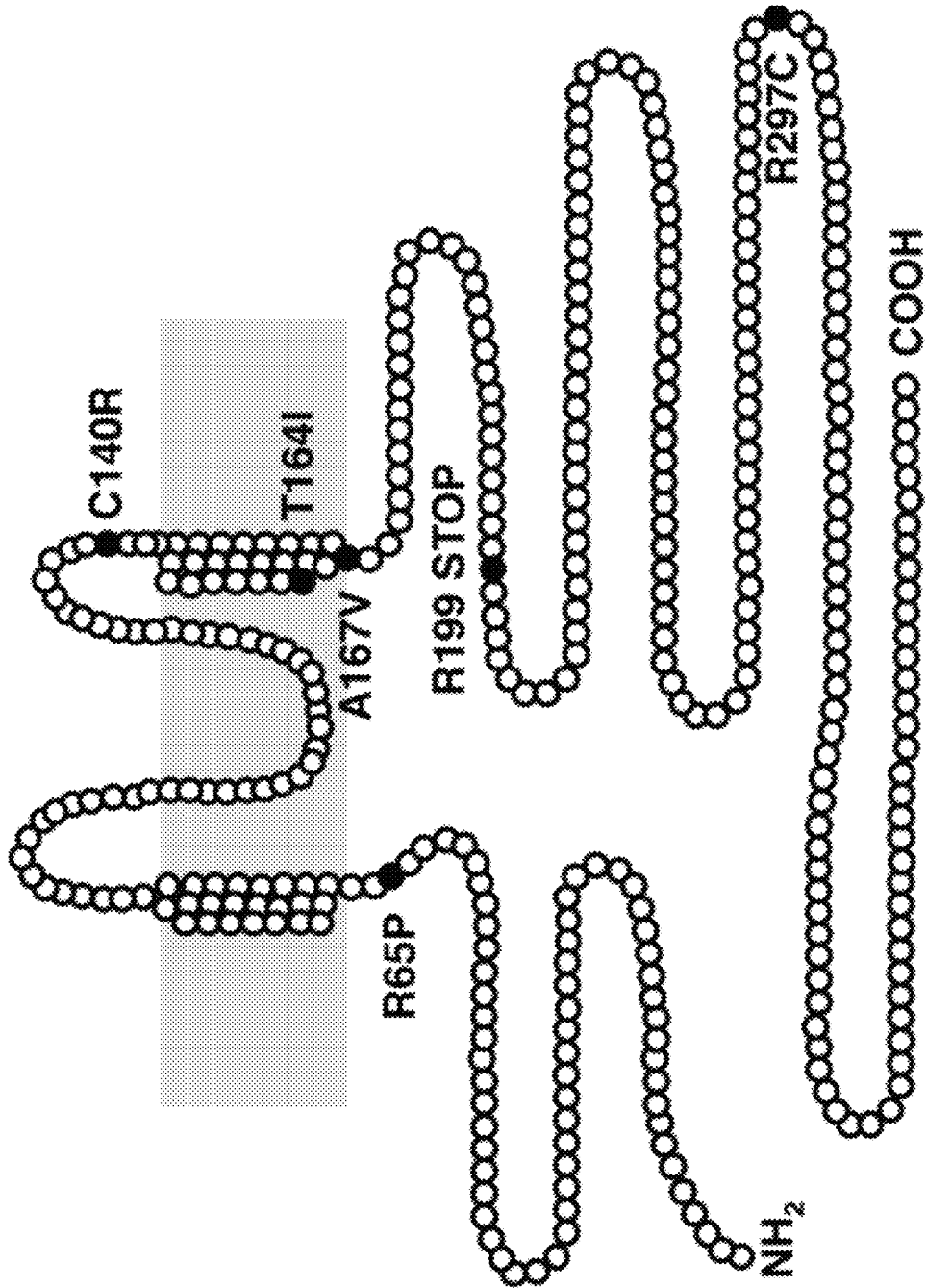
FIG. 3 is a schematic illustration of location of KCNJ10 mutations in patients with SeSAME syndrome. A schematic view of the protein is shown, with intracellular N- and C-termini, two transmembrane helices (plasma membrane shown in shaded gray), and one pore. This structure is characteristic of the inward rectifier family. Locations of mutations are indicated by black circles, and the respective amino acid change is noted.

The present invention describes a novel syndrome, referred to herein as SeSAME syndrome, that is characterized by early onset seizures, sensorineuronal deafness, ataxia, mental retardation, and electrolyte imbalances, including hypokalemia, metabolic alkalosis, and hypomagnesemia. A subject afflicted with SeSAME syndrome may present with all or a subset of these clinical features at a given time. Further, a subject that presents with a subset of clinical features that comprise the SeSAME syndrome phenotype may progressively develop additional clinical features over time. A subject, as used herein, is a mammal, preferably a human.

The present invention describes specific mutations of a KCNJ10 gene product associated with SeSAME syndrome as well as the genes that encode these proteins. The invention also provides a recombinant cell that expresses a wild type KCNJ10 gene product or a mutant KCNJ10 that encodes a mutant KCNJ10 protein associated with SeSAME syndrome. The invention further includes transgenic animals comprising either a wild type KCNJ10 gene product or a mutant KCNJ10 that encodes a mutant KCNJ10 protein associated with SeSAME syndrome.

The present invention provides methods for the examination of cells, tissues, and fluids, collectively known as bodily samples, for the diagnosis or for assessing the prognosis of SeSAME syndrome. In one embodiment, the method of the invention comprises a method of detecting at least one mutation in the KCNJ10 gene or gene product that causes SeSAME syndrome. In another embodiment, the invention comprises a method of detecting a disrupted KCNJ10 transcript wherein said transcript may be detected at either the mRNA or protein level.

In another embodiment, the invention describes a method for screening compounds to identify therapeutic agents useful for treating SeSAME syndrome. The present invention also includes a method of treating SeSAME syndrome using therapeutic agents so identified.

Definitions:

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well known and commonly employed in the art.

Standard techniques are used for nucleic acid and peptide synthesis. The techniques and procedures are generally performed according to conventional methods in the art and various general references (e.g., Sambrook and Russell, 2001, Molecular Cloning, A Laboratory Approach, Cold Spring Harbor Press, Cold Spring Harbor, N.Y., and Ausubel et al., 2002, Current Protocols in Molecular Biology, John Wiley & Sons, NY), which are provided throughout this document.

The nomenclature used herein and the laboratory procedures used in analytical chemistry and organic syntheses described below are those well known and commonly employed in the art. Standard techniques or modifications thereof, are used for chemical syntheses and chemical analyses.

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent on the context in which it is used.

As used herein, an "allele" is one of several alternate forms of a gene or non-coding regions of DNA that occupy the same position on a chromosome.

"Allele specific detection assay" as used herein refers to an assay to detect the presence or absence of a predetermined mutation in a test polynucleotide or oligonucleotide by annealing the test polynucleotide or oligonucleotide with a polynucleotide or oligonucleotide of predetermined sequence such that differential DNA sequence based techniques or DNA amplification methods discriminate between normal and mutant.

"Amplification of polynucleotides" utilizes methods such as the polymerase chain reaction (PCR), ligation amplification (or ligase chain reaction, LCR) and amplification methods based on the use of Q-beta replicase. Also useful are strand displacement amplification (SDA), thermophilic SDA, and nucleic acid sequence based amplification (3SR or NASBA). These methods are well known and widely practiced in the art. See, e.g., U.S. Pat. Nos. 4,683,195 and 4,683,202 and Innis et al., 1990 (for PCR); Wu and Wallace, 1989 (for LCR); U.S. Pat. Nos. 5,270,184 and 5,455,166 and Walker et al., 1992 (for SDA); Spargo et al., 1996 (for thermophilic SDA) and U.S. Pat. No. 5,409,818, Fahy et al., 1991 and Compton, 1991 for 3SR and NASBA. Reagents and hardware for conducting PCR are commercially available. Primers useful to amplify sequences from the KCNJ10 region are preferably complementary to, and hybridize specifically to sequences in the KCNJ10 region or in regions that flank a target region therein. KCNJ10 sequences generated by amplification may be sequenced directly. Alternatively, but less desirably, the amplified sequence(s) may be cloned prior to sequence analysis. A method for the direct cloning and sequence analysis of enzymatically amplified genomic segments has been described by Scharf et al., 1986.

By the term "applicator," as the term is used herein, is meant any device including, but not limited to, a hypodermic syringe, a pipette, and the like, for administering the compounds and compositions of the invention.

As used herein, "aptamer" refers to a small molecule that can bind specifically to another molecule. Aptamers are typically either polynucleotide- or peptide-based molecules. A polynucleotidal aptamer is a DNA or RNA molecule, usually comprising several strands of nucleic acids, that adopt highly specific three-dimensional conformation designed to have appropriate binding affinities and specificities towards specific target molecules, such as peptides, proteins, drugs, vitamins, among other organic and inorganic molecules. Such polynucleotidal aptamers can be selected from a vast population of random sequences through the use of systematic evolution of ligands by exponential enrichment. A peptide aptamer is typically a loop of about 10 to about 20 amino acids attached to a protein scaffold that bind to specific ligands. Peptide aptamers may be identified and isolated from combinatorial libraries, using methods such as the yeast two-hybrid system.

"Binding partner" refers to a molecule capable of binding a ligand molecule with high specificity, as for example, an antigen and an antigen-specific antibody or an enzyme and its inhibitor. In general, the specific binding partners must bind with sufficient affinity to immobilize the analyte copy/complementary strand duplex (in the case of polynucleotide hybridization) under the isolation conditions. Specific binding partners are known in the art and include, for example, biotin and avidin or streptavidin, IgG and protein A, the numerous, known receptor-ligand couples, and complementary polynucleotide strands. In the case of complementary polynucleotide binding partners, the partners are normally at least about 15 bases in length, and may be at least 40 bases in length. It is well recognized by those of skill in the art that lengths shorter than 15 (e.g., 8 bases), between 15 and 40, and greater than 40 bases may also be used. The polynucleotides may be composed of DNA, RNA, or synthetic nucleotide analogs. Further binding partners can be identified using, e.g., the two-hybrid yeast screening assay as described herein.

The phrase "bodily sample" as used herein, means any sample comprising a cell, a tissue, or a bodily fluid in which expression of a KCNJ10 gene or gene product can be detected. Samples that are liquid in nature are referred to herein as "bodily fluids." Bodily samples may be obtained from a patient by a variety of techniques including, for example, by scraping or swabbing an area or by using a needle to aspirate bodily fluids. Methods for collecting various bodily samples are well known in the art.

The phrase "at-risk" as used herein refers to a subject with a greater than average likelihood of developing SeSAME syndrome.

A "biomarker" of the invention is any detectable mutation or variant of a mutation in the KCNJ10 gene or gene product that contributes to a subject being at-risk for SeSAME syndrome. The mutation or variant of the mutation may be detected at either the nucleic acid or protein level.

As used herein, a polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced there from.

The term "isolated" when used in relation to a nucleic acid, as in "isolated oligonucleotide" or "isolated polynucleotide" refers to a nucleic acid sequence that is identified and separated from at least one contaminant with which it is ordinarily associated in its source. Thus, an isolated nucleic acid is present in a form or setting that is different from that in which it is found in nature. In contrast, non-isolated nucleic acids (e.g., DNA and RNA) are found in the state they exist in nature. For example, a given DNA sequence (e.g., a gene) is found on the host cell chromosome in proximity to neighboring genes; RNA sequences (e.g., a specific mRNA sequence encoding a specific protein), are found in the cell as a mixture with numerous other mRNAs that encode a multitude of proteins. However, isolated nucleic acid includes, by way of example, such nucleic acid in cells ordinarily expressing that nucleic acid where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide contains at a minimum, the sense or coding strand (i.e., the oligonucleotide may be single-stranded), but may contain both the sense and anti-sense strands (i.e., the oligonucleotide may be double-stranded).

The term "isolated" when used in relation to a polypeptide, as in "isolated protein" or "isolated polypeptide" refers to a polypeptide that is identified and separated from at least one contaminant with which it is ordinarily associated in its source. Thus, an isolated polypeptide is present in a form or setting that is different from that in which it is found in nature. In contrast, non-isolated polypeptides (e.g., proteins and enzymes) are found in the state they exist in nature.

"Naturally-occurring" as applied to an object refers to the fact that the object can be found in nature. For example, a polypeptide or polynucleotide sequence that is present in an organism (including viruses) that can be isolated from a source in nature and which has not been intentionally modified by man is a naturally-occurring sequence.

"Complementary" as used herein to refer to a nucleic acid, refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

"Substantially complementary to" refers to probe or primer sequences which hybridize to the sequences listed under stringent conditions and/or sequences having sufficient homology with test polynucleotide sequences, such that the allele specific oligonucleotide probe or primers hybridize to the test polynucleotide sequences to which they are complementary.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, are reduced.

The terms "dysregulated" or "dysregulation," as used herein, refer to an impairment in a biological process which in turn may lead to deleterious physiological sequelae, or abnormal expression of a gene, nucleic acid, protein, peptide, or other biological molecule. In the case where expression of a gene, nucleic acid, protein, peptide, or other biological molecule is dysregulated, the gene, nucleic acid, protein, peptide, or other biological molecule is expressed, processed, or maintained at levels that are outside what is considered the normal range for that of that gene, nucleic acid, protein, peptide, or other biological molecule as determined by a skilled artisan. Dysregulation of a gene, nucleic acid, protein, peptide, or other biological molecule in a mammal may be determined by measuring the level of a gene, nucleic acid, protein, peptide, or other biological molecule in the mammal and comparing the level measured in that mammal to level measured in a matched population known not to be experiencing dysregulation of that gene, nucleic acid, protein, peptide, or other biological molecule dysregulated. Alternatively, the level may be compared to one measured in the same individual at a different time.

The terms "effective amount" and "pharmaceutically effective amount" refer to a non-toxic but sufficient amount of an agent that provides the desired biological result. That result can be reduction and/or alleviation of the signs, symptoms, or causes of a disease or disorder, or any other desired alteration of a biological system. An appropriate effective amount in any individual case may be determined by one of ordinary skill in the art using routine experimentation.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

The term "expression vector" as used herein refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules, siRNA, ribozymes, and the like. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). The term "nucleic acid" typically refers to large polynucleotides.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

By "expression cassette" is meant a nucleic acid molecule comprising a coding sequence operably linked to promoter/regulatory sequences necessary for transcription and, optionally, translation of the coding sequence.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a n inducible manner.

An "inducible" promoter is a nucleotide sequence which, when operably linked with a polynucleotide which encodes or specifies a gene product, causes the gene product to be produced substantially only when an inducer which corresponds to the promoter is present.

"Mutation" as used herein refers to an altered genetic sequence which results in the gene coding for a non-functioning protein or a protein with reduced or altered function. Generally, a mutation is associated with pathology or the potential for pathology.

"Polypeptide" refers to a polymer composed of amino acid residues, related naturally occurring structural variants, and synthetic non-naturally occurring analogs thereof linked via peptide bonds. Synthetic polypeptides can be synthesized, for example, using an automated polypeptide synthesizer.

The term "protein" typically refers to large polypeptides.
The term "peptide" typically refers to short polypeptides.
Conventional notation is used herein to portray polypeptide sequences: the left-hand end of a polypeptide sequence is the amino-terminus; the right-hand end of a polypeptide sequence is the carboxyl-terminus.

As used herein, a "peptidomimetic" is a compound containing non-peptidic structural elements that is capable of mimicking the biological action of a parent peptide. A peptidomimetic may or may not comprise peptide bonds.

A "polynucleotide" means a single strand or parallel and anti-parallel strands of a nucleic acid. Thus, a polynucleotide may be either a single-stranded or a double-stranded nucleic acid. In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

The term "oligonucleotide" typically refers to short polynucleotides, generally no greater than about 60 nucleotides. It will be understood that when a nucleotide sequence is represented by a DNA sequence (i.e., A, T, G, C), this also includes an RNA sequence (i.e., A, U, G, C) in which "U" replaces "T."

The term "recombinant DNA" as used herein is defined as DNA produced by joining pieces of DNA from different sources.

The term "recombinant polypeptide" as used herein is defined as a polypeptide produced by using recombinant DNA methods.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATT-GCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

Homology, for polypeptides, is typically measured using sequence analysis software, See, e.g., the Sequence Analysis Software Package of the Genetics Computer Group, University of Wisconsin Biotechnology Center, 910 University Avenue, Madison, Wis. 53705. Protein analysis software matches similar sequences using measures of homology assigned to various substitutions, deletions and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

The terms "substantial homology" or "substantial identity", when referring to polypeptides, indicate that the polypeptide or protein in question exhibits at least about 30% identity with an entire naturally-occurring protein or a portion thereof, usually at least about 70% identity, more usually at least about 80% identity, preferably at least about 90% identity, and more preferably at least about 95% identity.

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

"Variant" as the term is used herein, is a nucleic acid sequence or a peptide sequence that differs in sequence from a reference nucleic acid sequence or peptide sequence respectively, but retains essential properties of the reference molecule. The reference molecule may be a wild-type molecule or a molecule comprising a deleterious mutation. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

"Substantially similar function" or "functionally substantially equivalent" refers to the function of a modified nucleic acid or a modified protein, with reference to the wild-type KCNJ10 nucleic acid or wild-type KCNJ10 polypeptide. The modified polypeptide will be substantially homologous to the wild-type KCNJ10 polypeptide and will have substantially the same function. The modified polypeptide may have an altered amino acid sequence and/or may contain modified amino acids. In addition to the similarity of function, the modified polypeptide may have other useful properties, such as a longer half-life. The similarity of function (activity) of the modified polypeptide may be substantially the same as the activity of the wild-type KCNJ10 polypeptide. Alternatively, the similarity of function (activity) of the modified polypeptide may be higher than the activity of the wild-type KCNJ10 polypeptide. The modified polypeptide is synthesized using conventional techniques, or is encoded by a modified nucleic acid and produced using conventional techniques. The modified nucleic acid is prepared by conventional techniques. A nucleic acid with a function substantially similar to the wild-type KCNJ10 gene function produces the modified protein described above.

A polypeptide "fragment," "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

The polypeptides of the present invention, if soluble, may be coupled to a solid-phase support, e.g., nitrocellulose, nylon, column packing materials (e.g., Sepharose beads), magnetic beads, glass wool, plastic, metal, polymer gels, cells, or other substrates. Such supports may take the form, for example, of beads, wells, dipsticks, or membranes.

By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences with varying degrees of homology to a probe can be identified.

By "high stringent conditions" it is meant conditions wherein target sequences that are 100% complementary to the probe are identified (homologous probing).

By "moderately stringent conditions" it is meant conditions such as those described by Ausubel et al, 2002, Current Protocols in Molecular Biology, John Wiley & Sons, N.Y., wherein stringency conditions can be adjusted to allow some mismatching in sequences so that lower degrees of similarity are detected (heterologous probing).

"Target region" refers to a region of the nucleic acid which is amplified and/or detected. The term "target sequence" refers to a sequence with which a probe or primer will form a stable hybrid under desired conditions.

The practice of the present invention employs, unless otherwise indicated, conventional techniques of chemistry, molecular biology, microbiology, recombinant DNA, genetics, and immunology. See, e.g., Maniatis et al., 1982; Sambrook et al., 2001, Molecular Cloning: A Laboratory Manual, Cold Spring Harbor Laboratory Press, Cold Spring Harbor, N.Y.; Ausubel et al. 2002, Current Protocols in Molecular Biology, John Wiley & Sons, NY; Glover, 1985; Anand, 1992; Guthrie and Fink, 1991. A general discussion of techniques and materials for human gene mapping, including mapping of human chromosome 1, is provided, e.g., in White and Lalouel, 1988.

By the term "specifically binds," as used herein, is meant a molecule, such as an antibody, which recognizes and binds to another molecule or feature, but does not substantially recognize or bind other molecules or features in a sample.

As used herein, the term "transdominant negative mutant gene" refers to a gene encoding a protein product that prevents other copies of the same gene or gene product, which have not been mutated (i.e., which have the wild-type sequence) from functioning properly (e.g., by inhibiting wild type protein function). The product of a transdominant negative mutant gene is referred to herein as "dominant negative" or "DN" (e.g., a dominant negative protein, or a DN protein).

The phrase "inhibit," as used herein, means to reduce a molecule, a reaction, an interaction, a gene, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists.

The phrase "orthologs" or "orthologous genes," as used herein, are genes in different species but within one clade, that are similar to each other because they originated from a common ancestor.

A "paralog," as used here in, refers to homologous genetic sequences separated by a gene duplication event. For example, if a gene in an organism is duplicated to occupy two different positions in the same genome, then the two copies are paralogous. A set of sequences that are paralogous are called paralogs of each other. Paralogs typically have the same or similar function, but sometimes do not: due to lack of the original selective pressure upon one copy of the duplicated gene, this copy is free to mutate and acquire new functions.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like.

It is understood that any and all whole or partial integers between any ranges set forth herein are included herein.

Description:

The present invention provides compositions and methods for identifying a human subject who is at-risk of developing, is afflicted with or is carrier of a newly described syndrome characterized by seizure, sensorineuronal deafness, ataxia, mental retardation, and electrolyte imbalances (SeSAME syndrome). The method comprises detecting at least one mutation or a sequence variation of at least one mutation that contributes to the etiology of SeSAME syndrome, wherein if at least one such mutation or sequence variation of a mutation is detected, then the subject is at-risk of developing, is afflicted with or is a carrier of SeSAME syndrome.

The present invention further comprises a method for screening compounds to identify therapeutic agents useful for treating SeSAME syndrome, wherein when a compound modulates mutant KCNJ10 channel activity such that the activity of the mutant KCNJ10 channel is functionally equivalent to the activity of a wild-type KCNJ10 channel, then the compound is identified as a therapeutic agent that may be used to treat SeSAME syndrome.

In another embodiment, the present invention comprises a method of treating SeSAME syndrome using therapeutic agents so identified.

Compositions of the Invention
A. Nucleic Acids

The present invention discloses mutations in the KCNJ10 gene and gene product that are associated with a newly described syndrome, SeSAME syndrome. As used herein, "KCNJ10" or "KCNJ10 gene" means a nucleic acid molecule comprising the DNA sequence of SEQ ID NO:1; a DNA sequence that encodes a polypeptide containing the amino acid sequence comprising SEQ ID NO:2; and a DNA sequence that hybridizes to the complement of DNA sequences that encode an amino acid sequence comprising SEQ ID NO:2 under moderately stringent conditions.

The invention also includes a nucleic acid molecule that encodes a KCNJ10 mutant protein that is associated with SeSAME syndrome. Accordingly, the invention includes a nucleic acid molecule (SEQ ID NO:3) that encodes KCNJ10 R65P (SEQ ID NO:9) where the arginine at position 65 is replaced with a proline. In another embodiment, a mutation of the KCNJ10 gene that is associated with SeSAME syndrome includes a nucleic acid molecule (SEQ ID NO:4) that encodes KCNJ10 C140R (SEQ ID NO:10) where the cysteine at position 140 is replaced with an arginine. In still another embodiment, a mutation of the KCNJ10 gene includes a nucleic acid molecule (SEQ ID NO:5) that encodes KCNJ10 T164I (SEQ ID NO:11) where the threonine at position 164 is replaced with an isoleucine. In yet another embodiment, a mutation of the KCNJ10 gene includes a nucleic acid molecule (SEQ ID NO:6) that encodes KCNJ10 A167V (SEQ ID NO:12) where the alanine at position 167 is replaced with a valine. In another embodiment, a mutation of the KCNJ10 gene includes a nucleic acid molecule (SEQ ID NO:7) that encodes KCNJ10 R199STOP (SEQ ID NO:13) that results in truncation of the polypeptide at the arginine residue at amino acid 199. In yet another embodiment, a mutation of the KCNJ10 gene includes a nucleic acid molecule (SEQ ID NO:8) that encodes KCNJ10 R297C (SEQ ID NO:14) where the arginine at position 297 is replaced with a cysteine.

The nucleotide sequences encoding a wild type KCNJ10 peptide or a KCNJ10 mutant peptide associated with SeSAME syndrome can alternatively comprise sequence variations with respect to the reference nucleotide sequences, for example, substitutions, insertions and/or deletions of one or more nucleotides, with the condition that the resulting polynucleotide encodes a polypeptide according to the invention. Therefore, the scope of the present invention includes nucleotide sequences that are variants of the nucleotide sequences recited herein that encode a KCNJ10 peptide or a KCNJ10 mutant peptide associated with SeSAME syndrome.

A nucleotide sequence that is a variant of a nucleotide sequence encoding a KCNJ10 peptide or a KCNJ10 mutant-peptide associated with SeSAME syndrome can typically be isolated from a recombinant cell or organism by means of introducing conservative or non-conservative substitutions in the nucleic acid sequence that encodes KCNJ10 peptide or a KCNJ10 mutant peptide associated with SeSAME syndrome. Other examples of possible modifications include the insertion of one or more nucleotides in the sequence, the addition of one or more nucleotides in any of the ends of the sequence, or the deletion of one or more nucleotides in any end or inside the sequence.

In another aspect, the invention relates to a construct, comprising a nucleotide sequence encoding a KCNJ10 peptide or a KCNJ10 mutant peptide associated with SeSAME syndrome. In a particular embodiment, the construct is operatively bound to transcription, and optionally translation, control elements. The construct can incorporate an operatively bound regulatory sequence of the expression of the nucleotide sequence of the invention, thus forming an expression cassette.

A KCNJ10 peptide or a KCNJ10 mutant peptide associated with SeSAME syndrome may be prepared using recombinant DNA methods. Accordingly, nucleic acid molecules which encode a KCNJ10 peptide or a KCNJ10 mutant peptide associated with SeSAME syndrome may be incorporated in a known manner into an appropriate expression vector which ensures expression of the KCNJ10 peptide or a KCNJ10 mutant peptide associated with SeSAME syndrome.

Therefore, in another aspect, the invention relates to a vector, comprising the nucleotide sequence of the invention or the construct of the invention. The choice of the vector will depend on the host cell in which it is to be subsequently introduced. In a particular embodiment, the vector of the invention is an expression vector. Suitable host cells include a wide variety of prokaryotic and eukaryotic host cells. In specific embodiments, the expression vector is selected from the group consisting of a viral vector, a bacterial vector and a mammalian cell vector. Prokaryote- and/or eukaryote-vector based systems can be employed for use with the present invention to produce polynucleotides, or their cognate polypeptides. Many such systems are commercially and widely available.

Further, the expression vector may be provided to a cell in the form of a viral vector. Viral vector technology is well known in the art and is described, for example, in Sambrook et al., 2001, Molecular Cloning: A Laboratory Manual, Cold Spring Harbor Laboratory Press, Cold Spring Harbor, N.Y. and in Ausubel et al. 2002, Current Protocols in Molecular Biology, John Wiley & Sons, NY, and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193.

Vectors suitable for the insertion of the polynucleotides are vectors derived from expression vectors in prokaryotes such as pUC18, pUC19, Bluescript and the derivatives thereof; mp18, mp19, pBR322, pMB9, ColE1, pCR1, RP4, phages and "shuttle" vectors such as pSA3 and pAT28, expression vectors in yeasts such as vectors of the type of 2 micron plasmids, integration plasmids, YEP vectors, centromere plasmids and the like, expression vectors in insect cells such as vectors of the pAC series and of the pVL, expression vectors in plants such as pIBI, pEarleyGate, pAVA, pCAMBIA, pGSA, pGWB, pMDC, pMY, pORE series and the like, and expression vectors in eukaryotic cells based on viral vectors (adenoviruses, viruses associated to adenoviruses such as retroviruses and, particularly, lentiviruses) as well as non-viral vectors such as pSilencer 4.1-CMV (Ambion), pcDNA3, pcDNA3.1/hyg, pHMCV/Zeo, pCR3.1, pEFI/His, pIND/GS, pRc/HCMV2, pSV40/Zeo2, pTRACER-HCMV, pUB6/V5-His, pVAX1, pZeoSV2, pCI, pSVL and PKSV-10, pBPV-1, pML2d and pTDT1.

By way of illustration, the vector in which the nucleic acid sequence is introduced can be a plasmid which is or is not integrated in the genome of a host cell when it is introduced in the cell. Illustrative, non-limiting examples of vectors in which the nucleotide sequence of the invention or the gene construct of the invention can be inserted include a tet-on inducible vector for expression in eukaryote cells.

The vector may be obtained by conventional methods known by persons skilled in the art (Sambrook et al., 2001, Molecular Cloning: A Laboratory Manual, Cold Spring Harbor Laboratory Press, Cold Spring Harbor, N.Y.). In a particular embodiment, the vector is a vector useful for transforming animal cells.

The recombinant expression vectors may also contain nucleic acid molecules which encode a protein which provides increased expression of the recombinant KCNJ10 peptide or a KCNJ10 mutant peptide associated with SeSAME syndrome; increased solubility of the recombinant KCNJ10 peptide or a KCNJ10 mutant peptide associated with SeSAME syndrome; and/or aid in the purification of the recombinant KCNJ10 peptide or a KCNJ10 mutant peptide associated with SeSAME syndrome by acting as a ligand in affinity purification. For example, a proteolytic cleavage site may be inserted in the recombinant peptide to allow separation of the recombinant KCNJ10 peptide or a KCNJ10 mutant peptide associated with SeSAME syndrome after purification of the fusion protein. Examples of fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Additional promoter elements, i.e., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (U.S. Pat. Nos. 4,683,202, 5,928, 906). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al., 2001, Molecular Cloning: A Laboratory Manual, Cold Spring Harbor Laboratory Press, Cold Spring Harbor, N.Y. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

A promoter sequence exemplified in the experimental examples presented herein is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, Moloney virus promoter, the avian leukemia virus promoter, Epstein-Barr virus immediate early promoter, Rous sarcoma virus promoter, as well as human gene promoters such as, but not limited to, the actin promoter, the myosin promoter, the hemoglobin promoter, and the muscle creatine promoter. Further, the invention should not be limited to the use of constitutive promoters. Inducible promoters are also contemplated as part of the invention. The use of an inducible promoter in the invention provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. Further, the invention includes the use of a tissue specific promoter, which promoter is active only in a desired tissue. Tissue specific promoters are well known in the art and include, but are not limited to, the HER-2 promoter and the PSA associated promoter sequences.

In a particular embodiment, the expression of the nucleic acid is externally controlled. In a more particular embodiment, the expression is externally controlled using the doxycycline Tet-On system.

The recombinant expression vectors may also contain a selectable marker gene which facilitates the selection of transformed or transfected host cells. Suitable selectable marker genes are genes encoding proteins such as G418 and hygromycin which confer resistance to certain drugs, β-galactosidase, chloramphenicol acetyltransferase, firefly luciferase, or an immunoglobulin or portion thereof such as the Fc portion of an immunoglobulin preferably IgG. The selectable markers may be introduced on a separate vector from the nucleic acid of interest.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. Expression of the reporter gene is assayed at a suitable time after the DNA has been introduced into the recipient cells.

Suitable reporter genes may include genes encoding luciferase, beta-galactosidase, chloramphenicol acetyl transferase, secreted alkaline phosphatase, or the green fluorescent protein gene (see, e.g., Ui-Tei et al., 2000 FEBS Lett. 479:79-82). Suitable expression systems are well known and may be prepared using well known techniques or obtained commercially. Internal deletion constructs may be generated using unique internal restriction sites or by partial digestion of non-unique restriction sites. Constructs may then be transfected into cells that display high levels of siRNA polynucleotide and/or polypeptide expression. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Recombinant expression vectors may be introduced into host cells to produce a recombinant cell. The cells can be prokaryotic or eukaryotic. The vector of the invention can be used to transform eukaryotic cells such as yeast cells, *Saccharomyces cerevisiae*, or mammal cells for example epithelial kidney 293 cells or U2OS cells, or prokaryotic cells such as bacteria, *Escherichia coli* or *Bacillus subtilis*, for example. Nucleic acid can be introduced into a cell using conventional techniques such as calcium phosphate or calcium chloride co-precipitation, DEAE-dextran-mediated transfection, lipofectin, electroporation or microinjection. Suitable methods for transforming and transfecting host cells may be found in Sambrook et al., (2001, Molecular Cloning: A Laboratory Manual, Cold Spring Harbor Laboratory Press, Cold Spring Harbor, N.Y.), and other laboratory textbooks. For example, a KCNJ10 peptide or a KCNJ10 mutant peptide associated with SeSAME syndrome may be expressed in bacterial cells such as *E. coli*, insect cells (using baculovirus), yeast cells or mammalian cells. Other suitable host cells can be found in Goeddel, Gene Expression Technology: Methods in Enzymology 185, Academic Press, San Diego, Calif. (1991).

B. Polypeptides

The present invention also relates to a KCNJ10 gene product. As used herein, a "KCNJ10 gene product" includes amino acid sequences encoded by a normal KCNJ10 gene, including, for example, SEQ ID NO:2. This term is also meant to include functionally equivalent KCNJ10 gene products.

The invention also describes mutant KCNJ10 gene products that are associated with SeSAME syndrome. A mutation of the KCNJ10 gene that is associated with SeSAME in a human subject includes a polypeptide KCNJ10 R65P of SEQ ID NO:9 where the arginine at position 65 is replaced with a praline. In another embodiment, a mutant KCNJ10 gene product that is associated with SeSAME syndrome includes KCNJ10 C140R of SEQ ID NO:10 where the cysteine at position 140 is replaced with an arginine. In still another embodiment, a mutation of the KCNJ10 gene product includes KCNJ10 T164I of SEQ ID NO:11 where the threonine at position 164 is replaced with an isoleucine. In yet another embodiment, a mutation of the KCNJ10 gene product includes KCNJ10 A167V of SEQ ID NO:12 where the alanine at position 167 is replaced with a valine. In another embodiment, a mutation of the KCNJ10 gene product includes KCNJ10 R199STOP of SEQ ID NO:13 that results in truncation of the polypeptide at the arginine residue at amino acid 199. In yet another embodiment, a mutation of the KCNJ10 gene product includes KCNJ10 R297C of SEQ ID NO:14 where the arginine at position 297 is replaced with a cysteine.

A variant of the KCNJ10 protein or a mutant KCNJ10 protein associated with SeSAME syndrome may be (i) one in which one or more of the amino acid residues are substituted with a conserved or non-conserved amino acid residue (preferably a conserved amino acid residue) and such substituted amino acid residue may be one encoded by the genetic code or a non-natural amino acid, (ii) one in which there are one or more modified amino acid residues, e.g., residues that are modified by the attachment of substituent groups, (iii) one in which the polypeptide is an alternative splice variant of the polypeptide of the present invention, (iv) fragments of the polypeptides and/or (v) one in which the polypeptide is fused with another polypeptide, such as a leader or secretory sequence or a sequence which is employed for purification (for example, His-tag) or for detection (for example, Sv5 epitope tag). The fragments include polypeptides generated via proteolytic cleavage (including multi-site proteolysis) of an original sequence. Variants may be post-translationally, or chemically modified. Such variants are deemed to be within the scope of those skilled in the art from the teaching herein.

The polypeptides of the invention can be post-translationally modified. For example, post-translational modifications that fall within the scope of the present invention include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine microsomal membranes or Xenopus egg extracts (U.S. Pat. No. 6,103,489) to a standard translation reaction.

The polypeptides of the invention may include unnatural amino acids formed by post-translational modification or by introducing unnatural amino acids during translation. A variety of approaches are available for introducing unnatural amino acids during protein translation. By way of example, special tRNAs, such as tRNAs which have suppressor properties, suppressor tRNAs, have been used in the process of site-directed non-native amino acid replacement (SNAAR). In SNAAR, a unique codon is required on the mRNA and the suppressor tRNA, acting to target a non-native amino acid to a unique site during the protein synthesis (described in WO90/05785). However, the suppressor tRNA must not be recognizable by the aminoacyl tRNA synthetases present in the protein translation system. In certain cases, a non-native amino acid can be formed after the tRNA molecule is aminoacylated using chemical reactions which specifically modify the native amino acid and do not significantly alter the functional activity of the aminoacylated tRNA. These reactions are referred to as post-aminoacylation modifications. For example, the epsilon-amino group of the lysine linked to its cognate tRNA (tRNA$_{LYS}$), could be modified with an amine specific photoaffinity label.

Peptides of the invention may be developed using a biological expression system. The use of these systems allows the production of large libraries of random peptide sequences and the screening of these libraries for peptide sequences that bind to particular proteins. Libraries may be produced by cloning synthetic DNA that encodes random peptide sequences into appropriate expression vectors. (see Christian et al 1992, J. Mol. Biol. 227:711; Devlin et al, 1990 Science 249:404; Cwirla et al 1990, Proc. Natl. Acad. Sci. USA, 87:6378). Libraries may also be constructed by concurrent synthesis of overlapping peptides (see U.S. Pat. No. 4,708,871).

The peptides and chimeric proteins of the invention may be converted into pharmaceutical salts by reacting with inorganic acids such as hydrochloric acid, sulfuric acid, hydrobromic acid, phosphoric acid, etc., or organic acids such as formic acid, acetic acid, propionic acid, glycolic acid, lactic acid, pyruvic acid, oxalic acid, succinic acid, malic acid, tartaric acid, citric acid, benzoic acid, salicylic acid, benzenesulfonic acid, and toluenesulfonic acids.

Methods of the Invention

The present invention relates to the KCNJ10 gene and KCNJ10 gene products as well as mutations therein associated with SeSAME syndrome and their use as diagnostic markers for diagnosing an individual at risk for developing and/or being afflicted with SeSAME syndrome. The KCNJ10 gene and KCNJ10 gene products as well as mutations thereof are also useful in identifying new methods of treatment and therapeutic agents useful in treating subjects afflicted with SeSAME syndrome.

In one embodiment, the diagnostic methods of the invention comprise collecting a bodily sample from a subject and analyzing the sample for the presence of KCNJ10 mutations that are associated with SeSAME syndrome at the nucleic acid or protein level.

The invention also includes a method of diagnosing a subject as a carrier of SeSAME syndrome. In one aspect, a "carrier" is a subject that is capable of contributing to an increase in the risk of offspring of the subject to develop SeSAME syndrome. The method comprises the step of obtaining a bodily sample from the subject. The method further comprises the step of assaying the sample for the presence of at least one mutation in the KCNJ10 gene or at least one disruption in a KCNJ10 gene product in the sample, wherein, if the at least one mutation or gene product disruption is present in the sample, then the subject is diagnosed as a SeSAME syndrome carrier.

In one embodiment, the carrier is a female. In another embodiment, the carrier is a male. In yet another embodiment, the carrier is screened before conception of the offspring. In yet another embodiment, the carrier is screened during the gestation of the offspring. In yet another embodiment, the carrier is screened after the birth of the offspring. In yet another embodiment, the carrier is screened after the birth of the offspring and the diagnosis of the offspring as at-risk of developing or afflicted with SeSAME. In a non-limiting embodiment, both parents of the offspring are evaluated for being carriers of the SeSAME syndrome when at least one of the parents has a family member that is affected by the syndrome or is determined to be a carrier of the syndrome.

Any method available in the art for detecting a mutation or a disrupted gene product is encompassed herein. The invention should not be limited to those methods for detecting mutations or disrupted gene products recited herein, but rather should encompasses all known or heretofore unknown methods for detection as are, or become, known in the art.

Methods for detecting a mutation or disrupted gene product of KCNJ10 comprise any method that interrogates the KCNJ10 gene or its products at either the nucleic acid or protein level. Such methods are well known in the art and include, but are not limited to, nucleic acid hybridization techniques, nucleic acid reverse transcription methods, and nucleic acid amplification methods, western blots, northern blots, southern blots, ELISA, immunoprecipitation, immunofluorescence, flow cytometry, immunocytochemistry. In particular embodiments, disrupted gene transcription is detected on a protein level using, for example, antibodies that are directed against specific KCNJ10 proteins. These antibodies can be used in various methods such as Western blot, ELISA, immunoprecipitation, or immunocytochemistry techniques.

A. Detection of Mutations in the KCNJ10 Gene

In one embodiment, a diagnostic marker of the invention may comprise a nucleic acid. Accordingly, a mutation in the human KCNJ10 gene sequence or a variant of a mutation in the human KCNJ10 gene, may serve as a diagnostic marker for SeSAME syndrome. A subject may be diagnosed with SeSAME syndrome by detecting a mutation in the KCNJ10 gene of SEQ ID NO:1 or the KCNJ10 gene product of SEQ ID NO:2 in a biological sample obtained from the subject. Examples of a mutation of the KCNJ10 gene associated with SeSAME syndrome include SEQ ID NO:3, SEQ ID NO:4, SEQ ID NO:5, SEQ ID NO:6, SEQ ID NO:7, and SEQ ID NO:8. Examples of mutations of KCNJ10 gene products associated with SeSAME syndrome include SEQ ID NO:9, SEQ ID NO:10, SEQ ID NO:11, SEQ ID NO:12, SEQ ID NO:13, and SEQ ID NO:14.

A number of assay formats known in the art are useful for detecting chromosomal abnormalities. These methods commonly involve nucleic acid binding, e.g., to filters, beads, or microliter plates and the like; and include dot-blot methods, Northern blots, Southern blots, PCR, and RFLP methods, and the like. In one aspect, one skilled in the art may use these methods to determine complete or partial sequences of coding sequences of genes. In a non-limiting embodiment, the nucleic acid sequence of the gene coding sequence may be determined based on the sequence of the one or more corresponding mRNA sequences. Thus, reference to determination of a sequence as used herein may refer to sequencing of all or a portion of the coding sequence of a genomic DNA sequence, and may also refer to the sequencing of all of a portion of the coding sequence of an RNA.

"Locus of interest" refers to a selected region of nucleic acid that is within a larger region of nucleic acid wherein the locus contains a mutation or a variant of a mutation that contributes to the etiology of SeSAME syndrome. In one embodiment, a locus of interest comprises any region of the KCNJ10 gene. A locus of interest can include, but is not limited to, 1-100, 1-50, 1-20, or 1-10 nucleotides, preferably 1-6, 1-5, 1-4, 1-3, 1-2, or 1 nucleotide(s).

The loci of interest can be analyzed by a variety of methods including but not limited to fluorescence detection, DNA sequencing gel, capillary electrophoresis on an automated DNA sequencing machine, microchannel electrophoresis, and other methods of sequencing, Sanger dideoxy sequencing, mass spectrometry, time of flight mass spectrometry, quadrupole mass spectrometry, magnetic sector mass spectrometry, electric sector mass spectrometry infrared spectrometry, ultraviolet spectrometry, palentiostatic amperometry or by DNA hybridization techniques including Southern Blot, Slot Blot, Dot Blot, and DNA microarray, wherein DNA fragments would be useful as both "probes" and "targets," ELISA, fluorimetry, fluorescence polarization, Fluorescence Resonance Energy Transfer (FRET), SNP-IT, Gene Chips, HuSNP, BeadArray, TaqMan assay, Invader assay, MassExtend, or MassCleave™ (hMC) method.

Hybridization Assays

In one embodiment of the invention, chromosomal abnormalities are detected using a hybridization assay.

"Probe" refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

Fluorescence in situ hybridization ("FISH") is a cytogenetic technique that can be used to detect and localize the presence or absence of specific DNA sequences on chromosomes (Verma et al., 1988, Human Chromosomes: A Manual Of Basic Techniques, Pergamon Press, New York). Fluorescent probes are used that only bind to those portions of a chromosome with which they share a high degree of sequence homology. FISH can also be used to detect and localize specific mRNAs within a tissue sample. FISH of a cDNA clone to a metaphase chromosomal spread can be used to provide a precise chromosomal location in one step. This technique can be used with probes from the cDNA as short as 50 or 60 bp.

A FISH probe is constructed from fragments of isolated DNA and tagged directly with fluorophores, with targets for antibodies, or with biotin. Tagging can be done in various ways, for example nick translation and PCR using tagged nucleotides.

An interphase or metaphase chromosome preparation is produced from a sample obtained from a human subject. The chromosomes are firmly attached to a substrate, usually glass. Repetitive DNA sequences must be blocked by adding short fragments of DNA to the sample. The probe is then applied to the chromosome DNA and incubated for approximately 12 hours while hybridizing. Several wash steps remove all unhybridized or partially-hybridized probes. The results are then visualized and quantified using a microscope that is capable of exciting the dye and recording images.

Once a sequence has been mapped to a precise chromosomal location, the physical position of the sequence on the chromosome can be correlated with genetic map data. Such data are found, for example, in V. McKusick, Mendelian Inheritance In Man, available on-line through Johns Hopkins University, Welch Medical Library. The relationship between genes and diseases that have been mapped to the same chromosomal region are then identified through linkage analysis (coinheritance of physically adjacent genes).

Allele specific hybridization can be used to detect a pre-determined mutation or set of known mutations in a test gene. In accordance with the invention, such pre-determined mutations are detected by allele specific hybridization, a sequence-dependent-based technique which permits discrimination between normal and mutant alleles. An allele specific assay is dependent on the differential ability of mismatched nucleotide sequences (e.g., normal:mutant) to hybridize with each other, as compared with matching (e.g., normal:normal or mutant:mutant) sequences.

A variety of methods well-known in the art can be used for detection of a pre-determined mutation by allele specific hybridization. Preferably, the test gene is probed with allele specific oligonucleotides (ASOs); and each ASO contains the sequence of a known mutation. ASO analysis detects specific sequence variations in a target polynucleotide fragment by testing the ability of a specific oligonucleotide probe to hybridize to the target polynucleotide fragment. Preferably, the oligonucleotide contains the mutant sequence (or its complement). The presence of a mutation in the target sequence is indicated by hybridization between the oligonucleotide probe and the target fragment under conditions in which an oligonucleotide probe containing a normal sequence does not hybridize to the target fragment. A lack of hybridization between the mutant oligonucleotide probe and the target polynucleotide fragment indicates the absence of the specific mutation in the target fragment. In a preferred embodiment, the test samples are probed in a standard dot blot format. Each region within the test gene that contains the sequence corresponding to the ASO is individually applied to a solid surface, for example, as an individual dot on a membrane. Each individual region can be produced, for example, as a separate PCR amplification product using methods well-known in the art (see, for example, U.S. Pat. No. 4,683,202).

Membrane-based formats that can be used as alternatives to the dot blot format for performing ASO analysis include, but are not limited to, reverse dot blot, (multiplex amplification assay), and multiplex allele-specific diagnostic assay (MASDA).

In a reverse dot blot format, oligonucleotide or polynucleotide probes having known sequence are immobilized on the solid surface, and are subsequently hybridized with the labeled test polynucleotide sample. In this situation, the primers may be labeled or the NTPs maybe labeled prior to amplification to prepare a labeled test polynucleotide sample. Alternatively, the test polynucleotide sample may be labeled subsequent to isolation and/or synthesis.

In a multiplex format, individual samples contain multiple target sequences within the test gene, instead of just a single target sequence. For example, multiple PCR products each containing at least one of the ASO target sequences are applied within the same sample dot. Multiple PCR products can be produced simultaneously in a single amplification reaction using the methods of Caskey et al., U.S. Pat. No. 5,582,989. The same blot, therefore, can be probed by each ASO whose corresponding sequence is represented in the sample dots.

A MASDA format expands the level of complexity of the multiplex format by using multiple ASOs to probe each blot (containing dots with multiple target sequences). This procedure is described in detail in U.S. Pat. No. 5,589,330 and in Michalowsky et al., 1996 (American Journal of Human Genetics, 59(4): A272, poster 1573) each of which is incorporated herein by reference in its entirety. First, hybridization between the multiple ASO probe and immobilized sample is detected. This method relies on the prediction that the presence of a mutation among the multiple target sequences in a given dot is sufficiently rare that any positive hybridization signal results from a single ASO within the probe mixture hybridizing with the corresponding mutant target. The hybridizing ASO is then identified by isolating it from the site of hybridization and determining its nucleotide sequence.

Suitable materials that can be used in the dot blot, reverse dot blot, multiplex, and MASDA formats are well-known in the art and include, but are not limited to nylon and nitrocellulose membranes.

When the target sequences are produced by PCR amplification, the starting material can be chromosomal DNA in which case the DNA is directly amplified. Alternatively, the starting material can be mRNA, in which case the mRNA is first reversed transcribed into cDNA and then amplified according to the well known technique of RT-PCR (see, for example, U.S. Pat. No. 5,561,058).

Large scale arrays allow for the rapid analysis of many sequences. A review of the differences in the application and development of chip arrays is covered by Southern, 1996, Trends In Genetics 12: 110-115 and Cheng et al., 1996, Molecular Diagnosis, 1:183-200. Several approaches exist involving the manufacture of chip arrays. Differences include, but not restricted to: type of solid support to attach the immobilized oligonucleotides, labeling techniques for identification of mutations and variants thereof and changes in the sequence-based techniques of the target polynucleotide to the probe.

A promising methodology for large scale analysis on 'DNA chips' is described in detail in Hacia et al., (Nature Genetics, 14:441-447) which is hereby incorporated by reference in its entirety. As described in Hacia et al., 1996, (Nature Genetics, 14:441-447) high density arrays of over 96,000 oligonucleotides, each 20 nucleotides in length, are immobilized to a single glass or silicon chip using light directed chemical synthesis. Contingent on the number and design of the oligonucleotide probe, potentially every base in a sequence can be interrogated for alterations. Oligonucleotides applied to the chip, therefore, can contain sequence variations that are not yet known to occur in the population, or they can be limited to mutations that are known to occur in the population.

Prior to hybridization with oligonucleotide probes on the chip, the test sample is isolated, amplified and labeled (e.g. fluorescent markers) by means well known to those skilled in the art. The test polynucleotide sample is then hybridized to the immobilized oligonucleotides. The intensity of sequence-based techniques of the target polynucleotide to the immobilized probe is quantitated and compared to a reference sequence. The resulting genetic information can be used in molecular diagnosis.

A common, but not limiting, utility of the 'DNA chip' in molecular diagnosis is screening for known mutations. However, this may impose a limitation on the technique by only looking at mutations that have been described in the field. The present invention allows allele specific hybridization analysis be performed with a far greater number of mutations than previously available. Thus, the efficiency and comprehensiveness of large scale ASO analysis will be broadened, reducing the need for cumbersome end-to-end sequence analysis, not only with known mutations but in a comprehensive manner all mutations which might occur as predicted by the principles accepted, and the cost and time associated with these cumbersome tests will be decreased.

Array based comparative hybridization is another methodology that allows high resolution screening by hybridizing differentially labeled test and reference DNAs to arrays consisting of thousands of clones and detects chromosomal variations with high resolution.

Amplification Assays

In one embodiment, chromosomal abnormalities are detected using an amplification assay. Template DNA can be amplified using any suitable method known in the art including but not limited to PCR (polymerase chain reaction), 3SR (self-sustained sequence reaction), LCR (ligase chain reaction), RACE-PCR (rapid amplification of cDNA ends), PLCR (a combination of polymerase chain reaction and ligase chain reaction), Q-beta phage amplification (Shah et al., J. Medical Micro. 33: 143541 (1995)), SDA (strand displacement amplification), SOE-PCR (splice overlap extension PCR), and the like. In a preferred embodiment, the template DNA is amplified using PCR (PCR: A Practical Approach, M. J. McPherson, et al., IRL Press (1991); PCR Protocols: A Guide to Methods and Applications, Innis, et al., Academic Press (1990); and PCR Technology: Principals and Applications of DNA Amplification, H. A. Erlich, Stockton Press (1989)). PCR is also described in numerous U.S. patents, including U.S. Pat. Nos. 4,683,195; 4,683,202; 4,800,159; 4,965,188; 4,889,818; 5,075,216; 5,079,352; 5,104,792, 5,023,171; 5,091,310; and 5,066,584.

Primer Design

Published sequences, including consensus sequences, can be used to design or select primers for use in amplification of template DNA. The selection of sequences to be used for the construction of primers that flank a locus of interest can be made by examination of the sequence of the loci of interest, or immediately thereto. The recently published sequence of the human genome provides a source of useful consensus sequence information from which to design primers to flank a desired human gene locus of interest.

By "flanking" a locus of interest is meant that the sequences of the primers are such that at least a portion of the 3' region of one primer is complementary to the antisense strand of the template DNA and upstream from the locus of interest site (forward primer), and at least a portion of the 3' region of the other primer is complementary to the sense strand of the template DNA and downstream of the locus of interest (reverse primer). A "primer pair" is intended a pair of forward and reverse primers. Both primers of a primer pair anneal in a manner that allows extension of the primers, such that the extension results in amplifying the template DNA in the region of the locus of interest.

Primers can be prepared by a variety of methods including but not limited to cloning of appropriate sequences and direct chemical synthesis using methods well known in the art (Narang et al., Methods Enzymol. 68:90 (1979); Brown et al., Methods Enzymol. 68:109 (1979)). Primers can also be obtained from commercial sources such as Operon Technologies, Amersham Pharmacia Biotech, Sigma, and Life Technologies. The primers can have an identical melting temperature. The lengths of the primers can be extended or shortened at the 5' end or the 3' end to produce primers with desired melting temperatures. In a preferred embodiment, one of the primers of the primer pair is longer than the other primer. In a preferred embodiment, the 3' annealing lengths of the primers, within a primer pair, differ. Also, the annealing position of each primer pair can be designed such that the sequence and length of the primer pairs yield the desired melting temperature. The simplest equation for determining the melting temperature of primers smaller than 25 base pairs is the Wallace Rule (Td=2(A+T)+4(G+C)). Computer programs can also be used to design primers, including but not limited to Array Designer Software (Arrayit Inc.), Oligonucleotide Probe Sequence Design Software for Genetic Analysis (Olympus Optical Co.), NetPrimer, and DNAsis from Hitachi Software Engineering. The $T_M$ (melting or annealing temperature) of each primer is calculated using software programs such as Net Primer (free web based program at <<http://premierbiosoft.com/netprimer/netprlaunch/netprlaunch.html>>.

In another embodiment, the annealing temperature of the primers can be recalculated and increased after any cycle of amplification, including but not limited to cycle 1, 2, 3, 4, 5, cycles 6-10, cycles 10-15, cycles 15-20, cycles 20-25, cycles 25-30, cycles 30-35, or cycles 35-40. After the initial cycles of amplification, the 5' half of the primers is incorporated into the products from each loci of interest, thus the $T_M$ can be recalculated based on both the sequences of the 5' half and the 3' half of each primer.

As used herein, the term "about" with regard to annealing temperatures is used to encompass temperatures within 10° C. of the stated temperatures.

In one embodiment, one primer pair is used for each locus of interest. However, multiple primer pairs can be used for each locus of interest.

Template

Any nucleic acid specimen, in purified or nonpurified form, can be utilized as the starting nucleic acid or acids, providing it contains, or is suspected of containing, the specific nucleic acid sequence containing the CNTNAP2 gene, AUTS2 gene, or portions thereof. The term "template" therefore refers to any nucleic acid molecule that can be used for amplification in the invention. RNA or DNA that is not naturally double stranded can be made into double stranded DNA so as to be used as template DNA. Any double stranded DNA or preparation containing multiple, different double stranded DNA molecules can be used as template DNA to amplify a locus or loci of interest contained in the template DNA. In one embodiment, the sequence which sequence is to be determined is derived from genomic DNA on an exon-by-exon basis. In another embodiment, the sequence which sequence is to be determined is derived from genomic DNA based on targeted exon sequences.

The template DNA can be from any appropriate sample including but not limited to, nucleic acid-containing samples of tissue, bodily fluid, umbilical cord blood, chorionic amniotic fluid, an embryo, a two-celled embryo, a four-celled embryo, an eight-celled embryo, a 16-celled embryo, a 32-celled embryo, a 64-celled embryo, a 128-celled embryo, a 256-celled embryo, a 512-celled embryo, a 1024-celled embryo, embryonic tissues, lymph fluid, cerebrospinal fluid, mucosa secretion, or other bodily exudate, using protocols well established within the art.

In one embodiment, the template DNA can be obtained from a sample of a pregnant female. In another embodiment, the template DNA can be obtained from an embryo. In a preferred embodiment, the template DNA can be obtained from a single-cell of an embryo.

In one embodiment, the template DNA is fetal DNA. Fetal DNA can be obtained from sources including but not limited to maternal blood, maternal serum, maternal plasma, fetal cells, umbilical cord blood, chorionic villi, amniotic fluid, urine, saliva, cells or tissues.

The nucleic acid that is to be analyzed can be any nucleic acid, e.g., genomic, including DNA that has been reverse transcribed from an RNA sample, such as cDNA. The sequence of RNA can be determined according to the invention if it is capable of being made into a double stranded DNA form to be used as template DNA.

Amplification

The amplification step may amplify, for example, DNA or RNA, including messenger RNA, wherein DNA or RNA may be single stranded or double stranded. In the event that RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. The specific nucleic acid sequence to be amplified, i.e., the polymorphic locus, may be a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as contained in whole human DNA.

In one embodiment, the nucleic acid is amplified directly in the original sample containing the source of nucleic acid. It is not essential that the nucleic acid be extracted, purified or isolated; it only needs to be provided in a form that is capable of being amplified. Hybridization of the nucleic acid template with primer, prior to amplification, is not required. For example, amplification can be performed in a cell or sample lysate using standard protocols well known in the art. DNA that is on a solid support, in a fixed biological preparation, or otherwise in a composition that contains non-DNA substances and that can be amplified without first being extracted from the solid support or fixed preparation or non-DNA substances in the composition can be used directly, without further purification, as long as the DNA can anneal with appropriate primers, and be copied, especially amplified, and the copied or amplified products can be recovered and utilized as described herein.

In a preferred embodiment, the nucleic acid is extracted, purified or isolated from non-nucleic acid materials that are in the original sample using methods known in the art prior to amplification.

In another embodiment, the nucleic acid is extracted, purified or isolated from the original sample containing the source of nucleic acid and prior to amplification, the nucleic acid is fragmented using any number of methods well known in the art including but not limited to enzymatic digestion, manual shearing, or sonication. For example, the DNA can be digested with one or more restriction enzymes that have a recognition site, and especially an eight base or six base pair recognition site, which is not present in the loci of interest. Typically, DNA can be fragmented to any desired length, including 50, 100, 250, 500, 1,000, 5,000, 10,000, 50,000 and 100,000 base pairs long. In another embodiment, the DNA is fragmented to an average length of about 1000 to 2000 base pairs. However, it is not necessary that the DNA be fragmented.

Fragments of DNA that contain the loci of interest can be purified from the fragmented DNA before amplification. Such fragments can be purified by using primers that will be used in the amplification (see "Primer Design" section below) as hooks to retrieve the loci of interest, based on the ability of such primers to anneal to the loci of interest. In a preferred embodiment, tag-modified primers are used, such as e.g. biotinylated primers.

By purifying the DNA fragments containing the loci of interest, the specificity of the amplification reaction can be improved. This will minimize amplification of nonspecific regions of the template DNA. Purification of the DNA fragments can also allow multiplex PCR (Polymerase Chain Reaction) or amplification of multiple loci of interest with improved specificity.

The components of a typical PCR reaction include but are not limited to a template DNA, primers, a reaction buffer (dependent on choice of polymerase), dNTPs (dATP, dTTP, dGTP, and dCTP) and a DNA polymerase. Suitable PCR primers can be designed and prepared according to methods well known in the art. Briefly, the reaction is heated to 95° C. for 2 minutes to separate the strands of the template DNA, the reaction is cooled to an appropriate temperature (determined by calculating the annealing temperature of designed primers) to allow primers to anneal to the template DNA, and heated to 72° C. for two minutes to allow extension.

After annealing, the temperature in each cycle is increased to an "extension" temperature to allow the primers to "extend" and then following extension the temperature in each cycle is increased to the denaturization temperature. For PCR products less than 500 base pairs in size, one can eliminate the extension step in each cycle and just have denaturization and annealing steps. A typical PCR reaction consists of 25-45 cycles of denaturation, annealing and extension as described above. However, as previously noted, one cycle of amplification (one copy) can be sufficient for practicing the invention.

In another embodiment, multiple sets of primers wherein a primer set comprises a forward primer and a reverse primer, can be used to amplify the template DNA for 1-5, 5-10, 10-15, 15-20 or more than 20 cycles, and then the amplified product is further amplified in a reaction with a single primer set or a subset of the multiple primer sets. In a preferred embodiment, a low concentration of each primer set is used to minimize primer-dimer formation. A low concentration of starting DNA can be amplified using multiple primer sets. Any number of primer sets can be used in the first amplification reaction including but not limiting to 1-10, 10-20, 20-30, 30-40, 40-50, 50-60, 60-70, 70-80, 80-90, 90-100, 100-150, 150-200, 200-250, 250-300, 300-350, 350-400, 400-450, 450-500, 500-1000, and greater than 1000. In another embodiment, the amplified product is amplified in a second reaction with a single primer set. In another embodiment, the amplified product is further amplified with a subset of the multiple primer pairs including but not limited to 2-10, 10-20, 20-30, 30-40, 40-50, 50-60, 60-70, 70-80, 80-90, 90-100, 100-150, 150-200, 200-250, and more than 250.

The multiple primer sets will amplify the loci of interest, such that a minimal amount of template DNA is not limiting for the number of loci that can be detected. For example, if template DNA is isolated from a single cell or the template DNA is obtained from a pregnant female, which comprises both maternal template DNA and fetal template DNA, low concentrations of each primer set can be used in a first amplification reaction to amplify the loci of interest. The low concentration of primers reduces the formation of primer-dimer and increases the probability that the primers will anneal to the template DNA and allow the polymerase to extend. The optimal number of cycles performed with the multiple primer sets is determined by the concentration of the primers. Following the first amplification reaction, additional primers can be added to further amplify the loci of interest. Additional amounts of each primer set can be added and further amplified in a single reaction. Alternatively, the amplified product can be further amplified using a single primer set in each reaction or a subset of the multiple primers sets. For example, if 150 primer sets were used in the first amplification reaction, subsets of 10 primer sets can be used to further amplify the product from the first reaction.

Any DNA polymerase that catalyzes primer extension can be used including but not limited to E. coli DNA polymerase, Klenow fragment of E. coli DNA polymerase 1, T7 DNA polymerase, T4 DNA polymerase, Taq polymerase, Pfu DNA polymerase, Vent DNA polymerase, bacteriophage 29, REDTaq™ Genomic DNA polymerase, or sequenase. Preferably, a thermostable DNA polymerase is used. A "hot start" PCR can also be performed wherein the reaction is heated to 95° C. for two minutes prior to addition of the polymerase or the polymerase can be kept inactive until the first heating step in cycle 1. "Hot start" PCR can be used to minimize nonspecific amplification. Any number of PCR cycles can be used to amplify the DNA, including but not limited to 2, 5, 10, 15, 20, 25, 30, 35, 40, or 45 cycles. In a most preferred embodiment, the number of PCR cycles performed is such that equimolar amounts of each loci of interest are produced.

Purification of the amplified DNA is not necessary for practicing the invention. However, in one embodiment, if purification is preferred, the 5' end of the primer (first or second primer) can be modified with a tag that facilitates purification of the PCR products. In a preferred embodiment, the first primer is modified with a tag that facilitates purification of the PCR products. The modification is preferably the same for all primers, although different modifications can be used if it is desired to separate the PCR products into different groups.

The tag can be any chemical moiety including but not limited to a radioisotope, fluorescent reporter molecule, chemiluminescent reporter molecule, antibody, antibody fragment, hapten, biotin, derivative of biotin, photobiotin, iminobiotin, digoxigenin, avidin, enzyme, acridinium, sugar, enzyme, apoenzyme, homopolymeric oligonucleotide, hormone, ferromagnetic moiety, paramagnetic moiety, diamagnetic moiety, phosphorescent moiety, luminescent moiety, electrochemiluminescent moiety, chromatic moiety, moiety having a detectable electron spin resonance, electrical capacitance, dielectric constant or electrical conductivity, or combinations thereof.

As one example, the 5' ends of the primers can be biotinylated (Kandpal et al., Nucleic Acids Res. 18:1789-1795 (1990); Kaneoka et al., Biotechniques 10:30-34 (1991); Green et al., Nucleic Acids Res. 18:6163-6164 (1990)). The biotin provides an affinity tag that can be used to purify the copied DNA from the genomic DNA or any other DNA molecules that are not of interest. Biotinylated molecules can be purified using a streptavidin coated matrix, including but not limited to Streptawell, transparent, High-Bind plates from Roche Molecular Biochemicals (catalog number 1 645 692, as listed in Roche Molecular Biochemicals, 2001 Biochemicals Catalog).

The PCR product of each locus of interest is placed into separate wells of a Streptavidin coated plate. Alternatively, the PCR products of the loci of interest can be pooled and placed into a streptavidin coated matrix, including but not limited to the Streptawell, transparent, High-Bind plates from Roche Molecular Biochemicals (catalog number 1 645 692, as listed in Roche Molecular Biochemicals, 2001 Biochemicals Catalog).

The amplified DNA can also be separated from the template DNA using non-affinity methods known in the art, for example, by polyacrylamide gel electrophoresis using standard protocols.

Sequence Analysis of Amplification Products

A variety of methods are employed to analyze the nucleotide sequence of the amplification products. Several techniques for detecting point mutations following amplification by PCR have been described in Chehab et al., 1992, Methods in Enzymology, 216:135-143; Maggio et al., 1993, Blood, 81(1):239-242; Cai and Kan, 1990, Journal of Clinical Investigation, 85(2):550-553; and Cai et al., 1989, Blood, 73:372-374.

One particularly useful technique is analysis of restriction enzyme sites following amplification. In this method, amplified nucleic acid segments are subjected to digestion by restriction enzymes. Identification of differences in restriction enzyme digestion between corresponding amplified segments in different individuals identifies a point mutation. Differences in the restriction enzyme digestion is commonly determined by measuring the size of restriction fragments by electrophoresis and observing differences in the electrophoretic patterns. Generally, the sizes of the restriction fragments is determined by standard gel electrophoresis techniques as described in Sambrook, et al, 2001, Molecular Cloning A Laboratory Manual, Cold Spring Harbor Press, and, e.g., in Polymeropoulos et al., 1992, Genomics, 12:492-496.

The size of the amplified segments obtained from affected and normal individuals and digested with appropriate restriction enzymes are analyzed on agarose or polyacrylamide gels. Because of the high discrimination of the polyacrylamide gel electrophoresis, differences of small magnitude are easily detected. Other mutations resulting in DPDD-related polymorphisms of DPD encoding genes also add unique restriction sites to the gene that are determined by sequencing DPDD-related nucleic acid sequences and comparing them to normal sequences.

Another useful method of identifying point mutations in PCR amplification products employs oligonucleotide probes specific for different sequences. The oligonucleotide probes are mixed with amplification products under hybridization conditions. Probes are either RNA or DNA oligonucleotides and optionally contain not only naturally occurring nucleotides but also analogs such as digoxygenin dCTP, biotin dCTP, 7-azaguanosine, azidothymidine, inosine, or uridine. The advantage of using nucleic acids comprising analogs include selective stability, resistance to nuclease activity, ease of signal attachment, increased protection from extraneous contamination and an increased number of probe-specific colored labels. For instance, in preferred embodiments, oligonucleotide arrays are used for the detection of specific point mutations as described below.

Probes are typically derived from cloned nucleic acids, or are synthesized chemically. When cloned, the isolated nucleic acid fragments are typically inserted into a replication vector, such as lambda phage, pBR322, M13, pJB8, c2RB, pcos1EMBL, or vectors containing the SP6 or 17 promoter and cloned as a library in a bacterial host. General probe cloning procedures are described in Sambrook, et al, 2001, Molecular Cloning A Laboratory Manual, Cold Spring Harbor Press.

The amplification products may also be detected by analyzing it by Southern blots without using radioactive probes. In such a process, for example, a small sample of DNA containing a very low level of the nucleic acid sequence of the polymorphic locus is amplified, and analyzed via a Southern blotting technique or similarly, using dot blot analysis. The use of non-radioactive probes or labels is facilitated by the high level of the amplified signal. Alternatively, probes used to detect the amplified products can be directly or indirectly detectably labeled, for example, with a radioisotope, a fluorescent compound, a bioluminescent compound, a chemiluminescent compound, a metal chelator or an enzyme. Those of ordinary skill in the art will know of other suitable labels for binding to the probe, or will be able to ascertain such, using routine experimentation. In the preferred embodiment, the amplification products are determinable by separating the mixture on an agarose gel containing ethidium bromide which causes DNA to be fluorescent.

Alternative methods of amplification have been described and can also be used in the practice of the instant invention. Such alternative amplification systems include but are not limited to self-sustained sequence replication, which begins with a short sequence of RNA of interest and a T7 promoter. Reverse transcriptase copies the RNA into cDNA and degrades the RNA, followed by reverse transcriptase polymerizing a second strand of DNA. Another nucleic acid amplification technique is nucleic acid sequence-based amplification (NASBA) which uses reverse transcription and T7 RNA polymerase and incorporates two primers to target its cycling scheme. NASBA can begin with either DNA or RNA and finish with either, and amplifies to $10^8$ copies within 60 to 90 minutes. Alternatively, nucleic acid can be amplified by ligation activated transcription (LAT). LAT works from a single-stranded template with a single primer that is partially single-stranded and partially double-stranded. Amplification is initiated by ligating a cDNA to the promoter oligonucleotide and within a few hours, amplification is $10^8$ to $10^9$ fold. The QB replicase system can be utilized by attaching an RNA sequence called MDV-1 to RNA complementary to a DNA sequence of interest. Upon mixing with a sample, the hybrid RNA finds its complement among the specimen's mRNAs and binds, activating the replicase to copy the tag-along sequence of interest. Another nucleic acid amplification technique, ligase chain reaction (LCR), works by using two differently labeled halves of a sequence of interest which are covalently bonded by ligase in the presence of the contiguous sequence in a sample, forming a new target. The repair chain reaction (RCR) nucleic acid amplification technique uses two complementary and target-specific oligonucleotide probe pairs, thermostable polymerase and ligase, and DNA nucleotides to geometrically amplify targeted sequences. A 2-base gap separates the oligonucleotide probe pairs, and the RCR fills and joins the gap, mimicking normal DNA repair. Nucleic acid amplification by strand displacement activation (SDA) utilizes a short primer containing a recognition site for Hine II with short overhang on the 5' end which binds to target DNA. A DNA polymerase fills in the part of the primer opposite the overhang with sulfur-containing adenine analogs. Hine II is added but only cuts the unmodified DNA strand. A DNA polymerase that lacks 5' exonuclease activity enters at the cite of the nick and begins to polymerize, displacing the initial primer strand downstream and building a new one which serves as more primer. SDA produces greater than $10^7$-fold amplification in 2 hours at 37° C. Unlike PCR and LCR, SDA does not require instrumented Temperature cycling. Another amplification system useful in the method of the invention is the QB Replicase System.

Sequencing Assays

In one embodiment, chromosomal abnormalities are detected using a sequencing assay. The term DNA sequencing encompasses biochemical methods for determining the order of the nucleotide bases, adenine, guanine, cytosine, and thymine, in a DNA molecule.

Chain-termination Methods

The classical chain-termination or Sanger method requires a single-stranded DNA template, a DNA primer, a DNA polymerase, radioactively or fluorescently labeled nucleotides, and modified nucleotides that terminate DNA strand elongation. The DNA sample is divided into four separate sequencing reactions, containing all four of the standard deoxynucleotides (dATP, dGTP, dCTP and dTTP) and the DNA polymerase. To each reaction is added only one of the four dideoxynucleotides (ddATP, ddGTP, ddCTP, or ddTTP). These dideoxynucleotides are the chain-terminating nucleotides, lacking a 3'-OH group required for the formation of a phosphodiester bond between two nucleotides during DNA strand elongation. Incorporation of a dideoxynucleotide into the nascent (elongating) DNA strand therefore terminates DNA strand extension, resulting in various DNA fragments of varying length. The dideoxynucleotides are added at lower concentration than the standard deoxynucleotides to allow strand elongation sufficient for sequence analysis.

The newly synthesized and labeled DNA fragments are heat denatured, and separated by size (with a resolution of just one nucleotide) by gel electrophoresis on a denaturing polyacrylamide-urea gel. Each of the four DNA synthesis reactions is run in one of four individual lanes (lanes A, T, G, C); the DNA bands are then visualized by autoradiography or UV light, and the DNA sequence can be directly read off the X-ray film or gel image. X-ray film is exposed to the gel, and the dark bands correspond to DNA fragments of different lengths. A dark band in a lane indicates a DNA fragment that is the result of chain termination after incorporation of a dideoxynucleotide (ddATP, ddGTP, ddCTP, or ddTTP). The terminal nucleotide base can be identified according to which dideoxynucleotide was added in the reaction giving that band. The relative positions of the different bands among the four lanes are then used to read (from bottom to top) the DNA sequence as indicated.

Dye-terminator Sequencing

An alternative to primer labelling is labelling of the chain terminators, a method commonly called 'dye-terminator sequencing'. The major advantage of this method is that the sequencing can be performed in a single reaction, rather than four reactions as in the labelled-primer method. In dye-terminator sequencing, each of the four dideoxynucleotide chain terminators is labelled with a different fluorescent dye, each fluorescing at a different wavelength. The dye-terminator sequencing method, along with automated high-throughput DNA sequence analyzers, is now being used for the vast majority of sequencing projects.

High-throughput Sequencing

The high demand for low cost sequencing has given rise to a number of high-throughput sequencing technologies (Hall, 2007, The Journal of Experimental Biology 209: 1518-1525; Church, 2006, Scientific American 294: 47-54). Many of the new high-throughput methods use methods that parallelize the sequencing process, producing thousands or millions of sequences at once.

In Vitro Clonal Amplification

As molecular detection methods are often not sensitive enough for single molecule sequencing, most approaches use an in vitro cloning step to generate many copies of each individual molecule. Emulsion PCR is one method, isolating individual DNA molecules along with primer-coated beads in aqueous bubbles within an oil phase. A polymerase chain reaction (PCR) then coats each bead with clonal copies of the isolated library molecule and these beads are subsequently immobilized for later sequencing, also known as "emulsion PCR" (Margulies, et al., 2005, Nature 437: 376-380; Shendure, et al., 2005, Science 309:1728-1732).

Another method for in vitro clonal amplification is "bridge PCR", where fragments are amplified upon primers attached to a solid surface, developed and used by Solexa. These methods both produce many physically isolated locations which each contain many copies of a single fragment. The single-molecule method developed by Stephen Quake's laboratory (later commercialized by Helicos) skips this amplification step, directly fixing DNA molecules to a surface.

Parallel Sequencing

Once clonal DNA sequences are physically localized to separate positions on a surface, various sequencing approaches may be used to determine the DNA sequences of all locations, in parallel. "Sequencing by synthesis", like the popular dye-termination electrophoretic sequencing, uses the process of DNA synthesis by DNA polymerase to identify the bases present in the complementary DNA molecule. Reversible terminator methods (used by Illumina and Helicos) use reversible versions of dye-terminators, adding one nucleotide at a time, detecting fluorescence corresponding to that position, then removing the blocking group to allow the polymerization of another nucleotide.

Sequencing by ligation is another enzymatic method of sequencing, using a DNA ligase enzyme rather than polymerase to identify the target sequence (Shendure et al., 2005, Science 309: 1728-1732; U.S. Pat. No. 5,750,341). This method uses a pool of all possible oligonucleotides of a fixed length, labeled according to the sequenced position. Oligonucleotides are annealed and ligated; the preferential ligation by DNA ligase for matching sequences results in a signal corresponding to the complementary sequence at that position.

Pyrosequencing is a method of DNA sequencing (determining the order of nucleotides in DNA) based on the "sequencing by synthesis" principle, which relies on detection of pyrophosphate release on nucleotide incorporation rather than chain termination with dideoxynucleotides (Margulies, et al., 2005, Nature 437:376-380; Ronaghi et al., 1996, Analytical Biochemistry 242:84-89).

"Sequencing by synthesis" involves taking a single strand of the DNA to be sequenced and then synthesizing its complementary strand enzymatically. The Pyrosequencing method is based on detecting the activity of DNA polymerase (a DNA synthesizing enzyme) with another chemiluminescent enzyme. Essentially, the method allows sequencing of a single strand of DNA by synthesizing the complementary strand along it, one base pair at a time, and detecting which base was actually added at each step. The template DNA is immobilized, and solutions of A, C, G, and T nucleotides are added and removed after the reaction, sequentially. Light is produced only when the nucleotide solution complements the first unpaired base of the template. The sequence of solutions which produce chemiluminescent signals allows the determination of the sequence of the template.

ssDNA template is hybridized to a sequencing primer and incubated with the enzymes DNA polymerase, ATP sulfurylase, luciferase and apyrase, and with the substrates adenosine 5' phosphosulfate (APS) and luciferin. The addition of one of the four deoxynucleotide triphosphates (dNTPs) or, in the case of dATP, dATPαS, is added which is not a substrate for a luciferase) initiates the second step. DNA polymerase incorporates the correct, complementary dNTPs onto the template. This incorporation releases pyrophosphate (PPi) stoichiometrically. ATP sulfurylase quantitatively converts PPi to ATP in the presence of adenosine 5' phosphosulfate. This ATP acts as fuel to the luciferase-mediated conversion of luciferin to oxyluciferin that generates visible light in amounts that are proportional to the amount of ATP. The light produced in the luciferase-catalyzed reaction is detected by a camera and analyzed in a program. Unincorporated nucleotides and ATP are degraded by the apyrase, and the reaction can restart with another nucleotide.

Other Sequencing Technologies

Other methods of DNA sequencing may have advantages in terms of efficiency or accuracy. Like traditional dye-terminator sequencing, they are limited to sequencing single isolated DNA fragments. "Sequencing by hybridization" is a non-enzymatic method that uses a DNA microarray. In this method, a single pool of unknown DNA is fluorescently labeled and hybridized to an array of known sequences. If the unknown DNA hybridizes strongly to a given spot on the array, causing it to "light up", then that sequence is inferred to exist within the unknown DNA being sequenced. G. J. Hanna, V. A. Johnson, D. R. Kuritzkes, D. D. Richman, J. Martinez-Picado, L. Sutton, J. D. Hazelwood, R. T. D'Aquila, 2000, Journal of Clinical Microbiology 38 (7): 2715 Mass spectrometry can also be used to sequence DNA molecules; conventional chain-termination reactions produce DNA molecules of different lengths and the length of these fragments is then determined by the mass differences between them (rather than using gel separation; Edwards, et al. Mutation Research 573 (1-2): 3-12).

B. Detection of a Disrupted Gene Product

Protein Assays

In one embodiment, a diagnostic marker of the invention may comprise a KCNJ10 gene product (e.g., SEQ ID NO:2), a mutant of a KCNJ10 gene product (e.g., SEQ ID NO.9, SEQ ID NO:10, SEQ ID NO:11, SEQ ID NO:12, SEQ ID NO:13, SEQ ID NO:14), or a variant of a mutant KCNJ10 gene product. Accordingly, a human KCNJ10 gene product, a mutation thereof, or a variant of a mutation thereof, may serve as a diagnostic biomarker for SeSAME syndrome. A subject may be diagnosed with SeSAME syndrome or identified as being at risk for developing SeSAME syndrome by detecting mutations in the KCNJ10 gene product (SEQ ID NO:2) in a biological sample obtained from the subject. Examples of mutations of KCNJ10 gene products associated with SeSAME syndrome and which may be used as biomarkers for a subject at risk of developing or afflicted with SeSAME syndrome include KCNJ10 R65P (SEQ ID NO:3), where the arginine at position 65 is replaced with a proline. In another embodiment, a mutant gene product includes KCNJ10 C140R (SEQ ID NO:4), where the cysteine at position 140 is replaced with an arginine. In still another embodiment, a mutant gene product includes KCNJ10 T164I (SEQ ID NO:5), where the threonine at position 164 is replaced with an isoleucine. In yet another embodiment, a mutant gene product includes KCNJ10 A167V (SEQ ID NO:6), where the alanine at position 167 is replaced with a valine. In another embodiment, a mutant gene product includes KCNJ10 R199STOP (SEQ ID NO:7), that results in truncation of the polypeptide at the arginine residue at amino acid 199. In yet another embodiment, a mutant gene product includes KCNJ10 R297C (SEQ ID NO:8), where the arginine at position 297 is replaced with a cysteine.

Accordingly, in another embodiment of the invention, disruption of a KCNJ10 gene product is detected at the protein level using antibodies specific for biomarker proteins of the invention. The method comprises obtaining a bodily sample from a patient, contacting the bodily sample with at least one antibody directed to a biomarker. One of skill in the art will recognize that the immunocytochemistry method described herein below is performed manually or in an automated fashion.

When the antibody used in the methods of the invention is a polyclonal antibody (IgG), the antibody is generated by inoculating a suitable animal with a biomarker protein, peptide or a fragment thereof. Antibodies produced in the inoculated animal which specifically bind the biomarker protein are then isolated from fluid obtained from the animal. Biomarker antibodies may be generated in this manner in several non-human mammals such as, but not limited to goat, sheep, horse, rabbit, and donkey. Methods for generating polyclonal antibodies are well known in the art and are described, for example in Harlow, et al. (1988, In: Antibodies, A Laboratory Manual, Cold Spring Harbor, N.Y.). These methods are not repeated herein as they are commonly used in the art of antibody technology.

When the antibody used in the methods of the invention is a monoclonal antibody, the antibody is generated using any well known monoclonal antibody preparation procedures such as those described, for example, in Harlow et al. (supra) and in Tuszynski et al. (1988, Blood, 72:109-115). Given that these methods are well known in the art, they are not replicated herein. Generally, monoclonal antibodies directed against a desired antigen are generated from mice immunized with the antigen using standard procedures as referenced herein. Monoclonal antibodies directed against full length or peptide fragments of biomarker may be prepared using the techniques described in Harlow, et al. (1988, In: Antibodies, A Laboratory Manual, Cold Spring Harbor, N.Y.).

Samples may need to be modified in order to render the biomarker antigens accessible to antibody binding. In a particular aspect of the immunocytochemistry methods, slides are transferred to a pretreatment buffer, for example phosphate buffered saline containing Triton-X. Incubating the sample in the pretreatment buffer rapidly disrupts the lipid bilayer of the cells and renders the antigens (i.e., biomarker proteins) more accessible for antibody binding. The pretreatment buffer may comprise a polymer, a detergent, or a nonionic or anionic surfactant such as, for example, an ethyloxylated anionic or nonionic surfactant, an alkanoate or an alkoxylate or even blends of these surfactants or even the use of a bile salt. The pretreatment buffers of the invention are used in methods for making antigens more accessible for antibody binding in an immunoassay, such as, for example, an immunocytochemistry method or an immunohistochemistry method.

Any method for making antigens more accessible for antibody binding may be used in the practice of the invention, including antigen retrieval methods known in the art. See, for example, Bibbo, 2002, Acta. Cytol. 46:25 29; Saqi, 2003, Diagn. Cytopathol. 27:365 370; Bibbo, 2003, Anal. Quant. Cytol. Histol. 25:8 11. In some embodiments, antigen retrieval comprises storing the slides in 95% ethanol for at least 24 hours, immersing the slides one time in Target Retrieval Solution pH 6.0 (DAKO S1699)/dH2O bath preheated to 95° C., and placing the slides in a steamer for 25 minutes.

Following pretreatment or antigen retrieval to increase antigen accessibility, samples are blocked using an appropriate blocking agent, e.g., a peroxidase blocking reagent such as hydrogen peroxide. In some embodiments, the samples are blocked using a protein blocking reagent to prevent non-specific binding of the antibody. The protein blocking reagent may comprise, for example, purified casein, serum or solution of milk proteins. An antibody directed to a biomarker of interest is then incubated with the sample.

Techniques for detecting antibody binding are well known in the art. Antibody binding to a biomarker of interest may be detected through the use of chemical reagents that generate a detectable signal that corresponds to the level of antibody binding and, accordingly, to the level of biomarker protein expression. In one of the preferred immunocytochemistry methods of the invention, antibody binding is detected through the use of a secondary antibody that is conjugated to a labeled polymer. Examples of labeled polymers include but are not limited to polymer-enzyme conjugates. The enzymes in these complexes are typically used to catalyze the deposition of a chromogen at the antigen-antibody binding site, thereby resulting in cell staining that corresponds to expression level of the biomarker of interest. Enzymes of particular interest include horseradish peroxidase (HRP) and alkaline phosphatase (AP). Commercial antibody detection systems, such as, for example the Dako Envision+ system (Dako North America, Inc., Carpinteria, Calif.) and Mach 3 system (Biocare Medical, Walnut Creek, Calif.), may be used to practice the present invention.

In one particular immunocytochemistry method of the invention, antibody binding to a biomarker is detected through the use of an HRP-labeled polymer that is conjugated to a secondary antibody. Antibody binding can also be detected through the use of a mouse probe reagent, which binds to mouse monoclonal antibodies, and a polymer conjugated to HRP, which binds to the mouse probe reagent. Slides are stained for antibody binding using the chromogen 3,3-diaminobenzidine (DAB) and then counterstained with hematoxylin and, optionally, a bluing agent such as ammonium hydroxide or TBS/Tween-20. In some aspects of the invention, slides are reviewed microscopically by a cytotechnologist and/or a pathologist to assess cell staining (i.e., biomarker overexpression). Alternatively, samples may be reviewed via automated microscopy or by personnel with the assistance of computer software that facilitates the identification of positive staining cells.

Detection of antibody binding can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{35}S$, or $^{3}H$.

In regard to detection of antibody staining in the immunocytochemistry methods of the invention, there also exist in the art video-microscopy and software methods for the quantitative determination of an amount of multiple molecular species (e.g., biomarker proteins) in a biological sample, wherein each molecular species present is indicated by a representative dye marker having a specific color. Such methods are also known in the art as colorimetric analysis methods. In these methods, video-microscopy is used to provide an image of the biological sample after it has been stained to visually indicate the presence of a particular biomarker of interest. Some of these methods, such as those disclosed in U.S. patent application Ser. No. 09/957,446 and U.S. patent application Ser. No. 10/057,729 to Marcelpoil., incorporated herein by reference, disclose the use of an imaging system and associated software to determine the relative amounts of each molecular species present based on the presence of representative color dye markers as indicated by those color dye markers' optical density or transmittance value, respectively, as determined by an imaging system and associated software. These techniques provide quantitative determinations of the relative amounts of each molecular species in a stained biological sample using a single video image that is "deconstructed" into its component color parts.

The antibodies used to practice the invention are selected to have high specificity for the biomarker proteins of interest. Methods for making antibodies and for selecting appropriate antibodies are known in the art. See, for example, Celis, J. E. ed., 2005, Cell Biology & Laboratory Handbook, 3rd edition (Academic Press, New York), which is herein incorporated in its entirety by reference. In some embodiments, commercial antibodies directed to specific biomarker proteins may be used to practice the invention. The antibodies of the invention may be selected on the basis of desirable staining of cytological, rather than histological, samples. That is, in particular embodiments the antibodies are selected with the end sample type (i.e., cytology preparations) in mind and for binding specificity.

One of skill in the art will recognize that optimization of antibody titer and detection chemistry is needed to maximize the signal to noise ratio for a particular antibody. Antibody concentrations that maximize specific binding to the biomarkers of the invention and minimize non-specific binding (or "background") will be determined in reference to the type of biological sample being tested. In particular embodiments, appropriate antibody titers for use cytology preparations are determined by initially testing various antibody dilutions on formalin-fixed paraffin-embedded normal tissue samples. Optimal antibody concentrations and detection chemistry conditions are first determined for formalin-fixed paraffin-embedded tissue samples. The design of assays to optimize antibody titer and detection conditions is standard and well within the routine capabilities of those of ordinary skill in the art. After the optimal conditions for fixed tissue samples are determined, each antibody is then used in cytology preparations under the same conditions. Some antibodies require additional optimization to reduce background staining and/or to increase specificity and sensitivity of staining in the cytology samples.

Furthermore, one of skill in the art will recognize that the concentration of a particular antibody used to practice the methods of the invention will vary depending on such factors as time for binding, level of specificity of the antibody for the biomarker protein, and method of bodily sample preparation. Moreover, when multiple antibodies are used, the required concentration may be affected by the order in which the antibodies are applied to the sample, i.e., simultaneously as a cocktail or sequentially as individual antibody reagents. Furthermore, the detection chemistry used to visualize antibody binding to a biomarker of interest must also be optimized to produce the desired signal to noise ratio.

Immunoassays

Immunoassays, in their simplest and most direct sense, are binding assays. Certain preferred immunoassays are the various types of enzyme linked immunosorbent assays (ELISA) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, antibodies binding to the biomarker proteins of the invention are immobilized onto a selected surface exhibiting protein affinity, such as a well in a polystyrene microtiter plate. Then, a test composition suspected of containing the biomarker antigen, such as a clinical sample, is added to the wells. After binding and washing to remove non-specifically bound immunecomplexes, the bound antibody may be detected. Detection is generally achieved by the addition of a second antibody specific for the target protein, that is linked to a detectable label. This type of ELISA is a simple "sandwich ELISA". Detection may also be achieved by the addition of a second antibody, followed by the addition of a third antibody that has binding affinity for the second antibody, with the third antibody being linked to a detectable label.

In another exemplary ELISA, the samples suspected of containing the biomarker antigen are immobilized onto the well surface and then contacted with the antibodies of the invention. After binding and washing to remove non-specifically bound immunecomplexes, the bound antigen is detected. Where the initial antibodies are linked to a detectable label, the immunecomplexes may be detected directly. Again, the immunecomplexes may be detected using a second antibody that has binding affinity for the first antibody, with the second antibody being linked to a detectable label.

Another ELISA in which the proteins or peptides are immobilized, involves the use of antibody competition in the detection. In this ELISA, labeled antibodies are added to the wells, allowed to bind to the biomarker protein, and detected by means of their label. The amount of marker antigen in an unknown sample is then determined by mixing the sample with the labeled antibodies before or during incubation with coated wells. The presence of marker antigen in the sample acts to reduce the amount of antibody available for binding to the well and thus reduces the ultimate signal. This is appropriate for detecting antibodies in an unknown sample, where the unlabeled antibodies bind to the antigen-coated wells and also reduces the amount of antigen available to bind the labeled antibodies.

Irrespective of the format employed, ELISAs have certain features in common, such as coating, incubating or binding, washing to remove non-specifically bound species, and detecting the bound immunecomplexes. These are described as follows:

In coating a plate with either antigen or antibody, the wells of the plate are incubated with a solution of the antigen or antibody, either overnight or for a specified period of hours. The wells of the plate are then washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating of nonspecific adsorption sites on the immobilizing surface reduces the background caused by nonspecific binding of antisera to the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the control and/or clinical or biological sample to be tested under conditions effective to allow immunecomplex (antigen/antibody) formation. Detection of the immunecomplex then requires a labeled secondary binding ligand or antibody, or a secondary binding ligand or antibody in conjunction with a labeled tertiary antibody or third binding ligand.

Under conditions effective to allow immunecomplex (antigen/antibody) formation" means that the conditions preferably include diluting the antigens and antibodies with solutions such as, but not limited to, BSA, bovine gamma globulin (BOG) and phosphate buffered saline (PBS)/Tween. These added agents also tend to assist in the reduction of nonspecific background.

The "suitable" conditions also mean that the incubation is at a temperature and for a period of time sufficient to allow effective binding. Incubation steps are typically from about 1 to 2 to 4 hours, at temperatures preferably on the order of 25° to 27° C., or may be overnight at about 4° C.

Following all incubation steps in an ELISA, the contacted surface is washed so as to remove non-complexed material. A preferred washing procedure includes washing with a solution such as PBS/Tween, or borate buffer. Following the formation of specific immunecomplexes between the test sample and the originally bound material, and subsequent washing, the occurrence of even minute amounts of immunecomplexes may be determined.

To provide a detecting means, the second or third antibody will have an associated label to allow detection. Preferably, this label is an enzyme that generates a color or other detectable signal upon incubating with an appropriate chromogenic or other substrate. Thus, for example, the first or second immunecomplex can be detected with a urease, glucose oxidase, alkaline phosphatase or hydrogen peroxidase-conjugated antibody for a period of time and under conditions that favor the development of further immunecomplex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azido-di-(3-ethyl-benzthiazoline-6-sulfonic acid [ARTS] and $H_2O_2$, in the case of peroxidase as the enzyme label. Quantitation is then achieved by measuring the degree of color generation, e.g., using a visible spectra spectrophotometer.

mRNA Assays

In another embodiment of the invention, disruption of a gene product is detected at the mRNA level. Nucleic acid-based techniques for assessing mRNA expression are well known in the art and include, for example, determining the level of biomarker mRNA in a bodily sample. Many expression detection methods use isolated RNA. Any RNA isolation technique that does not select against the isolation of mRNA can be utilized for the purification of RNA from bodily samples (see, e.g., Ausubel et al. 2002, Current Protocols in Molecular Biology, John Wiley & Sons, N.Y.). Additionally, large numbers of tissue samples can readily be processed using techniques well known to those of skill in the art, such as, for example, the single-step RNA isolation process of Chomczynski, 1989, U.S. Pat. No. 4,843,155).

Isolated mRNA as a biomarker can be detected in hybridization or amplification assays that include, but are not limited to, Southern or Northern analyses, polymerase chain reaction analyses and probe arrays. One method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to an mRNA or genomic DNA encoding a biomarker of the present invention. Hybridization of an mRNA with the probe indicates that the biomarker in question is being expressed.

In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affymetrix gene chip array (Santa Clara, Calif.). A skilled artisan can readily adapt known mRNA detection methods for use in detecting the level of mRNA encoded by the biomarkers of the present invention.

An alternative method for detecting biomarker mRNA in a sample involves the process of nucleic acid amplification, e.g., by RT-PCR (the experimental embodiment set forth in Mullis, 1987, U.S. Pat. No. 4,683,202), ligase chain reaction (Barany, 1991, Proc. Natl. Acad. Sci. USA, 88:189 193), self sustained sequence replication (Guatelli, 1990, Proc. Natl. Acad. Sci. USA, 87:1874 1878), transcriptional amplification system (Kwoh, 1989, Proc. Natl. Acad. Sci. USA, 86:1173 1177), Q-Beta Replicase (Lizardi, 1988, Bio/Technology, 6:1197), rolling circle replication (Lizardi, U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, biomarker expression is assessed by quantitative fluorogenic RT-PCR (i.e., the TaqMan™ System). Such methods typically use pairs of oligonucleotide primers that are specific for the biomarker of interest. Methods for designing oligonucleotide primers specific for a known sequence are well known in the art.

Biomarker expression levels of RNA may be monitored using a membrane blot (such as used in hybridization analysis such as Northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The detection of biomarker expression may also comprise using nucleic acid probes in solution.

C. Genetic Screening

The identification of the association between the KCNJ10 gene mutations and SeSAME syndrome permits the early presymptomatic screening of individuals to identify those at risk for developing SeSAME syndrome. To identify such individuals, KCNJ10 alleles are screened for mutations either directly or after cloning the alleles. The alleles are tested for the presence of nucleic acid sequence differences from the normal allele using any suitable technique as described elsewhere herein, including but not limited to, one of the following methods: fluorescent in situ hybridization (FISH), direct DNA sequencing, PFGE analysis, Southern blot analysis, single stranded conformation analysis (SSCP), linkage analysis, RNase protection assay, allele specific oligonucleotide (ASO), dot blot analysis and PCR-SSCP analysis. Also useful is the recently developed technique of DNA microchip technology. For example, either (1) the nucleotide sequence of both the cloned alleles and normal KCNJ10 gene or appropriate fragment (coding sequence or genomic sequence) are determined and then compared, or (2) the RNA transcripts of the KCNJ10 gene or gene fragment are hybridized to single stranded whole genomic DNA from an individual to be tested, and the resulting heteroduplex is treated with Ribonuclease A (RNase A) and run on a denaturing gel to detect the location of any mismatches. Two of these methods can be carried out according to the following procedures.

The alleles of the KCNJ10 gene in an individual to be tested are cloned using conventional techniques. For example, a blood sample is obtained from the individual. The genomic DNA isolated from the cells in this sample is partially digested to an average fragment size of approximately 20 kb. Fragments in the range from 18-21 kb are isolated. The resulting fragments are ligated into an appropriate vector. The sequences of the clones are then determined and compared to the normal KCNJ10 gene.

Alternatively, polymerase chain reactions (PCRs) are performed with primer pairs for the 5' region or the exons of the KCNJ10 gene. PCRs can also be performed with primer pairs based on any sequence of the normal KCNQ2 or KCNQ3 gene. For example, primer pairs for one of the introns can be prepared and utilized. Finally, RT-PCR can also be performed on the MRNA. The amplified products are then analyzed by single stranded conformation polymorphisms (SSCP) using conventional techniques to identify any differences and these are then sequenced and compared to the normal gene sequence.

Individuals can be quickly screened for common KCNJ10 gene mutations by amplifying the individual's DNA using suitable primer pairs and analyzing the amplified product, e.g., by dot-blot hybridization using allele-specific oligonucleotide probes.

The second method employs RNase A to assist in the detection of differences between the normal KCNJ10 gene and defective genes. This comparison is performed in steps using small (~500 bp) restriction fragments of the KCNJ10 gene as the probe. First, the KCNJ10 gene is digested with a restriction enzyme(s) that cuts the gene sequence into fragments of approximately 500 bp. These fragments are separated on an electrophoresis gel, purified from the gel and cloned individually, in both orientations, into an SP6 vector (e.g., pSP64 or pSP65). The SP6-based plasmids containing inserts of the KCNJ10 gene fragments are transcribed in vitro using the SP6 transcription system, well known in the art, in the presence of $[\alpha^{32}P]GTP$, generating radiolabeled RNA transcripts of both strands of the gene.

Individually, these RNA transcripts are used to form heteroduplexes with the allelic DNA using conventional techniques. Mismatches that occur in the RNA:DNA heteroduplex, owing to sequence differences between the KCNJ10 fragment and the KCNJ10 allele subclone from the individual, result in cleavage in the RNA strand when treated with RNase A. Such mismatches can be the result of point mutations or small deletions in the individual's allele. Cleavage of the RNA strand yields two or more small RNA fragments, which run faster on the denaturing gel than the RNA probe itself.

Any differences which are found, will identify an individual as having a molecular mutation of the KCNJ10 gene and the consequent presence of SeSAME syndrome. These mutations can take a number of forms. The most severe forms would be frame shift mutations or large deletions which would cause the gene to code for an abnormal protein or one which would significantly alter protein expression. Less severe disruptive mutations would include small in-frame deletions and nonconservative base pair substitutions which would have a significant effect on the protein produced, such as changes to or from a cysteine residue, from a basic to an acidic amino acid or vice versa, from a hydrophobic to hydrophilic amino acid or vice versa, or other mutations which would affect secondary or tertiary protein structure. Silent mutations or those resulting in conservative amino acid substitutions would not generally be expected to disrupt protein function.

Genetic testing will enable practitioners to identify individuals at risk SeSAME syndrome, at, or even before, birth. Presymptomatic diagnosis of these subjects will enable prevention of this disorder.

D. Methods of Screening for Therapeutic Agents

The KCNJ10 gene and KCNJ10 gene products, SEQ ID NO:1 and SEQ ID NO:2, respectively, also provide useful tools for development of new treatments for SeSAME syndrome. For example, as demonstrated herein, mutations in the nucleotide sequence of SEQ ID NO:1 lead to disrupted protein function in individuals with SeSAME syndrome. Accordingly, therapeutic agents which mimic the KCNJ10 gene product, or therapeutic agents that inhibit or prevent activity of a KCNJ10 gene product mutation that is associated with SeSAME syndrome, may be useful in treating SeSAME syndrome. Alternatively, agents which alter expression and/or levels of the normal protein may also be useful in the treatment of SeSAME syndrome. Such agents can be identified in routine screening assays which assess levels of the KCNJ10 gene or KCNJ10 gene product.

The KCNJ10 gene and KCNJ10 gene products are also useful for identification of other proteins and/or genes encoding such proteins which interact with KCNJ10 gene products. Various methods for identifying such proteins and/or genes for encoding these proteins are known in the art. Well known techniques include, but are not limited to, yeast two hybrid systems and receptor binding assays.

The KCNJ10 protein, a KCNJ10 protein mutation associated with SeSAME syndrome, or a variant of a mutation associated with SeSAME syndrome employed in such a screen may either be free in solution, affixed to a solid support, or borne on a cell surface. One method of screening for a therapeutic agent utilizes eukaryotic or prokaryotic host cells which are stably transformed with recombinant polynucleotides expressing the polypeptide or fragment, preferably in competitive binding assays. Such cells, either in viable or fixed form, can be used for standard binding assays. One may measure, for example, the formation of complexes between a KCNJ10 protein, a mutant KCNJ10 protein associated with SeSAME syndrome, or a variant of a mutation associated with SeSAME syndrome and the compound being tested, or examine the degree to which the formation of a complex between a KCNJ10 protein, a mutant KCNJ10 protein associated with SeSAME syndrome, or a variant of a mutation associated with SeSAME syndrome and a known ligand is interfered with by the compound being tested.

Thus, the present invention provides methods of screening a compound to determine if it is a therapeutic agent, as defined herein. Methods of screening a compound comprise contacting a KCNJ10 protein, a KCNJ10 mutant protein associated with SeSAME syndrome, or a variant of a KCNJ10 mutant protein associated with SeSAME syndrome with a compound. The mixture is then assayed for the presence of a complex between the compound and a KCNJ10 protein, a KCNJ10 mutant protein associated with SeSAME syndrome, or a variant of a KCNJ10 mutant protein associated with SeSAME syndrome by methods well known in the art. Alternatively, a KCNJ10 protein, a KCNJ10 mutant protein associated with SeSAME syndrome, or a variant of a KCNJ10 mutant protein associated with SeSAME syndrome may be contacted with a compound in the presence of either a fragment derived from a KCNJ10 protein, a fragment of a KCNJ10 mutant protein associated with SeSAME syndrome, a fragment of a variant of a KCNJ10 mutant protein associated with SeSAME syndrome, or a ligand known to bind to a KCNJ10 protein. The mixture is then assayed for the presence of a complex between the compound and a KCNJ10 protein, a KCNJ10 mutant protein associated with SeSAME syndrome, or a variant of a KCNJ10 mutant protein associated with SeSAME syndrome by methods well known in the art. In such competitive binding assays, a KCNJ10 protein, a KCNJ10 mutant protein associated with SeSAME syndrome, or a variant of a KCNJ10 mutant protein associated with SeSAME syndrome is typically labeled. Free KCNJ10 polypeptide, mutant KCNJ10 polypeptide, a variant of a mutant KCNJ10 polypeptide, or a fragment thereof, is separated from that present in a protein:protein complex. The amount of free (i.e., uncomplexed) label is a measure of the binding of the compound being tested to a KCNJ10 protein, a KCNJ10 mutant protein associated with SeSAME syndrome, or a variant of a KCNJ10 mutant protein associated with SeSAME syndrome, or its interference with a KCNJ10 protein, a KCNJ10 mutant protein associated with SeSAME syndrome, or a variant of a KCNJ10 mutant protein associated with SeSAME syndrome:ligand binding, respectively. The amount of bound, rather than free, KCNJ10 protein, KCNJ10 mutant protein associated with SeSAME syndrome, or variant of a KCNJ10 mutant protein associated with SeSAME syndrome may also be measured. It is also possible to label the ligand rather than the KCNJ10 protein, KCNJ10 mutant protein associated with SeSAME syndrome, or variant of a KCNJ10 mutant protein associated with SeSAME syndrome and to measure the amount of ligand binding to a KCNJ10 protein, a KCNJ10 mutant protein associated with SeSAME syndrome, or a variant of a KCNJ10 mutant protein associated with SeSAME syndrome in the presence and in the absence of the compound being tested.

Another technique for screening for therapeutic agents provides high throughput screening for compounds having suitable binding affinity to a KCNJ10 protein, a KCNJ10 mutant protein associated with SeSAME syndrome, or a variant of a KCNJ10 mutant protein associated with SeSAME syndrome and is described in detail in Geysen (published PCT published application WO 84/03564). By way of a non-limiting example, large numbers of different small peptide test compounds are synthesized on a solid substrate, such as plastic pins or some other surface. The peptide test compounds are reacted with a KCNJ10 protein, a KCNJ10 mutant protein associated with SeSAME syndrome, or a variant of a KCNJ10 mutant protein associated with SeSAME syndrome and washed. Bound KCNJ10 protein, a KCNJ10 mutant protein associated with SeSAME syndrome, or a variant of a KCNJ10 mutant protein associated with SeSAME syndrome is then detected by methods well known in the art.

Purified KCNJ10 protein, a KCNJ10 mutant protein associated with SeSAME syndrome, or a variant of a KCNJ10 mutant protein associated with SeSAME syndrome can be coated directly onto plates for use in the aforementioned drug screening techniques. However, non-neutralizing antibodies to the polypeptide can be used to capture antibodies to immobilize a KCNJ10 protein, a KCNJ10 mutant protein associated with SeSAME syndrome, or a variant of a KCNJ10 mutant protein associated with SeSAME syndrome on the solid phase.

The invention also contemplates the use of competitive screening assays in which neutralizing antibodies capable of specifically binding a KCNJ10 protein, a KCNJ10 mutant protein associated with SeSAME syndrome, or a variant of a KCNJ10 mutant protein associated with SeSAME syndrome compete with a test compound for binding to a KCNJ10 protein, a KCNJ10 mutant protein associated with SeSAME syndrome, or a variant of a KCNJ10 mutant protein associated with SeSAME syndrome or fragments thereof. In this manner, the antibodies can be used to detect the presence of any peptide which shares one or more antigenic determinants of a KCNJ10 protein, a KCNJ10 mutant protein associated with SeSAME syndrome, or a variant of a KCNJ10 mutant protein associated with SeSAME syndrome.

The invention is particularly useful for screening compounds for use as therapeutic agents by using a KCNJ10 protein, a KCNJ10 mutant protein associated with SeSAME syndrome, or a variant of a KCNJ10 mutant protein associated with SeSAME syndrome in recombinant cells, transfected oocytes, or transgenic animals. A compound is added to the cells in culture or administered to a transgenic animal expressing a KCNJ10 mutant protein associated with SeSAME syndrome or a variant of a KCNJ10 mutant protein associated with SeSAME syndrome and the effect on the current of the potassium channel is compared to the current of a cell or animal containing the wild-type KCNJ10 protein. Compounds which modulate the KCNJ10 mutant current or the KCNJ10 mutant variant current to a more normal level are identified as therapeutic agents for treating or preventing SeSAME syndrome.

In accordance with these methods, the following assays are examples of assays which can be used for screening for compounds for use as therapeutic agents in treating SeSAME syndrome.

Briefly, a method of screening for a compound which modulates activity of a mutant KCNJ10 protein associated with SeSAME syndrome, or a variant thereof, may include contacting a mutant KCNJ10 protein associated with SeSAME syndrome, or a variant thereof, with one or more test compounds in a suitable reaction medium, testing the activity of the treated mutant KCNJ10 protein associated with SeSAME syndrome, or a variant thereof, and comparing that activity with the activity of the KCNJ10 protein, a mutant KCNJ10 protein associated with SeSAME syndrome, or a variant of a mutant KCNJ10 protein associated with SeSAME syndrome in comparable reaction medium untreated with the test compound. A difference in activity between the treated and untreated mutant KCNJ10 protein associated with SeSAME syndrome, or variant thereof, is indicative of a modulating effect of the relevant test compound.

Prior to or as well as being screened for modulation of activity, a test compound may be screened for ability to interact with a mutant KCNJ10 protein associated with SeSAME syndrome, or a variant thereof, e.g., in a yeast two-hybrid system (e.g., Bartel et al., 1993; Fields and Song, 1989; Chevray and Nathans, 1992; Lee et al., 1995). This system may be used as a coarse screen prior to testing a compound for actual ability to modulate activity of a mutant KCNJ10 protein associated with SeSAME syndrome, or a variant thereof. Alternatively, the screen could be used to screen test compounds for binding to a KCNJ10 protein, a mutant KCNJ10 protein associated with SeSAME syndrome, or a variant of a mutant KCNJ10 protein associated with SeSAME syndrome as a specific binding partner, or to find mimetics of a KCNJ10 protein.

Following identification of a compound as a therapeutic agent which modulates or affects activity of a mutant KCNJ10 protein associated with SeSAME syndrome, or a variant of a mutant KCNJ10 peptide associated with SeSAME syndrome, the therapeutic agent may be investigated further. Furthermore, it may be manufactured and/or used in preparation, i.e., manufacture or formulation, or a composition such as a medicament, pharmaceutical composition or drug. These may be administered to individuals.

The present invention extends in various aspects not only to a compound identified as a therapeutic agent using a nucleic acid molecule as a modulator of the activity of a mutant KCNJ10 protein or a variant of a mutant protein associated with SeSAME syndrome, in accordance with what is disclosed herein, but also a pharmaceutical composition, medicament, drug or other composition comprising such a therapeutic agent, a method comprising administration of such a composition comprising such a therapeutic agent, a method comprising administration of such a composition to a patient, e.g., for treatment (which may include preventative treatment) of SeSAME syndrome, use of such a therapeutic agent in the manufacture of a composition for administration, e.g., for treatment of SeSAME syndrome, and a method of making a pharmaceutical composition comprising admixing such a therapeutic agent with a pharmaceutically acceptable excipient, vehicle or carrier, and optionally other ingredients.

A therapeutic agent identified as a modulator of the function of a mutant KCNJ10 protein associated with SeSAME syndrome or a variant of a mutant KCNJ10 protein associated with SeSAME syndrome may be either a peptide or a non-peptide. Non-peptide "small molecules" are often preferred for many in vivo pharmaceutical uses. Accordingly, a mimetic or mimic of the therapeutic agent (particularly if a peptide) may be designed for pharmaceutical use.

The designing of mimetics to a known pharmaceutically active compound is a known approach to the development of pharmaceuticals based on a "lead" compound. This might be desirable where the active compound is difficult or expensive to synthesize or where it is unsuitable for a particular method of administration, e.g., pure peptides are unsuitable active agents for oral compositions as they tend to be quickly degraded by proteases in the alimentary canal. Mimetic design, synthesis and testing is generally used to avoid randomly screening large numbers of molecules for a target property.

There are several steps commonly taken in the design of a mimetic from a compound having a given target property. First, the particular parts of the compound that are critical and/or important in determining the target property are determined. In the case of a peptide, this can be done by systematically varying the amino acid residues in the peptide, e.g., by substituting each residue in turn. Alanine scans of peptide are commonly used to refine such peptide motifs. These parts or residues constituting the active region of the compound are known as its "pharmacophore".

Once the pharmacophore has been found, its structure is modeled according to its physical properties, e.g., stereochemistry, bonding, size and/or charge, using data from a range of sources, e.g., spectroscopic techniques, x-ray diffraction data and NMR. Computational analysis, similarity mapping (which models the charge and/or volume of a pharmacophore, rather than the bonding between atoms) and other techniques can be used in this modeling process.

In a variant of this approach, the three-dimensional structure of the ligand and its binding partner are modeled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted onto it can conveniently be selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent they exhibit it. Further optimization or modification can then be carried out to arrive at one or more final mimetics for in vivo or clinical testing.

E. Methods of Treating SeSAME Syndrome

Gene Therapy

Contacting cells in an individual with a functionally equivalent KCNJ10 gene product or a therapeutic agent that mimics KCNJ10 function, or ameliorated KCNJ10 function can inhibit or delay the onset of one or more symptoms of SeSAME in the individual. According to the present invention, a method is also provided of supplying wild-type KCNJ10 protein to a cell which carries a mutant KCNJ10 gene associated with SeSAME syndrome. Supplying wild-type KCNJ10 protein to a cell should allow normal functioning of the recipient cells. The wild-type gene or a part of the gene may be introduced into the cell in a vector such that the gene remains extrachromosomal. In such a situation, the gene will be expressed by the cell from the extrachromosomal location. More preferred is the situation where the wild-type gene or a part thereof is introduced into the mutant cell in such a way that it recombines with the endogenous mutant gene present in the cell. Such recombination requires a double recombination event which results in the correction of the gene mutation. Vectors for introduction of genes both for recombination and for extrachromosomal maintenance are known in the art, and any suitable vector may be used. Methods for introducing DNA into cells such as electroporation, calcium phosphate co-precipitation and viral transduction are known in the art, and the choice of method is within the competence of the practitioner.

As generally discussed above, a gene or gene fragment, where applicable, may be employed in gene therapy methods in order to increase the amount of the expression products of the wild type KCNJ10 gene even in those persons in which the wild type gene is expressed at a "normal" level, but the gene product is not fully functional.

Gene therapy would be carried out according to generally accepted methods, for example, as described by Friedman et al., 1991, Cell 66:799-806 or Culver, 1996, Bone Marrow Transplant 3:S6-9; Culver, 1996, Mol. Med, Today 2:234-236. Cells from a patient would be first analyzed by the diagnostic methods described above, to ascertain the production of a KCNJ10 protein or a mutant KCNJ10 protein associated with SeSAME syndrome in the cells. A virus or plasmid vector (see further details below), containing a copy of the KCNJ10 gene or a functional equivalent thereof linked to expression control elements and capable of replicating inside the cells, is prepared. The vector may be capable of replicating inside the cells. Alternatively, the vector may be replication deficient and is replicated in helper cells for use in gene therapy. Suitable vectors are known, such as disclosed in U.S. Pat. No. 5,252,479 and PCT published application WO 93/07282 and U.S. Pat. Nos. 5,691,198; 5,747,469; 5,436,146 and 5,753,500. The vector is then injected into the patient. If the transfected gene is not permanently incorporated into the genome of each of the targeted cells, the treatment may have to be repeated periodically.

Gene transfer systems known in the art may be useful in the practice of the gene therapy methods of the present invention. These include viral and nonviral transfer methods. A number of viruses have been used as gene transfer vectors or as the basis for repairing gene transfer vectors, including papovaviruses (e.g., SV40, Madzak et al., 1992, J. Gen. Virol. 73:1533-1536), adenovirus (Berkner, 1992; Curr. Topics Microbiol. Immunol. 158:39-66), vaccinia virus (Moss, 1992, Current Opin. Biotechnol. 3:518-522; Moss, 1996, PNAS 93:11341-11348), adeno-associated virus (Russell and Hirata, 1998, Mol. Genetics 18:325-330), herpesviruses including HSV and EBV (Fink et al., 1996, Ann. Rev. Neurosci. 19:265-287), lentiviruses (Naldini et al., 1996, PNAS 93:11382-11388), Sindbis and Semliki Forest virus (Berglund et al., 1993, Biotechnol. 11:916-920), and retroviruses of avian (Petropoulos et al., 1992, J. Virol. 66:3391-3397), murine (Miller, 1992, Hum. Gene Ther. 3:619-624), and human origin (Shimada et al., 1991; Helseth et al., 1990; Page et al., 1990; Buchsehacher and Panganiban, 1992, J. Virol. 66:2731-2739). Most human gene therapy protocols have been based on disabled murine retroviruses, although adenovirus and adeno-associated virus are also being used.

Nonviral gene transfer methods known in the art include chemical techniques such as calcium phosphate coprecipitation; mechanical techniques, for example microinjection; membrane fusion-mediated transfer via liposomes; and direct DNA uptake and receptor-mediated DNA transfer (Curiel et al., 1992, Am. J. Respir. Cell. Mol. Biol 6:247-252). Viral-mediated gene transfer can be combined with direct in vitro gene transfer using liposome delivery, allowing one to direct the viral vectors to the tumor cells and not into the surrounding non-dividing cells. Injection of producer cells would then provide a continuous source of vector particles. This technique has been approved for use in humans with inoperable brain tumors.

In an approach which combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalization, and degradation of the endosome before the coupled DNA is damaged. For other techniques for the delivery of adenovirus based vectors see U.S. Pat. Nos. 5,691,198; 5,747,469; 5,436,146 and 5,753,500.

Liposome/DNA complexes have been shown to be capable of mediating direct in vivo gene transfer. While in standard liposome preparations the gene transfer process is nonspecific, localized in vivo uptake and expression have been reported in tumor deposits, for example, following direct in situ administration.

Expression vectors in the context of gene therapy are meant to include those constructs containing sequences sufficient to express a polynucleotide that has been cloned therein. In viral expression vectors, the construct contains viral sequences sufficient to support packaging of the construct. If the polynucleotide encodes KCNJ10, expression will produce KCNJ10. If the polynucleotide encodes an antisense polynucleotide or a ribozyme, expression will produce the antisense polynucleotide or ribozyme. Thus in this context, expression does not require that a protein product be synthesized. In addition to the polynucleotide cloned into the expression vector, the vector also contains a promoter functional in eukaryotic cells. The cloned polynucleotide sequence is under control of this promoter. Suitable eukaryotic promoters include those described above. The expression vector may also include sequences, such as selectable markers and other sequences described herein.

Gene transfer techniques which target DNA directly to brain, cochlear or renal tissue is preferred. Receptor-mediated gene transfer, for example, is accomplished by the conjugation of DNA (usually in the form of covalently closed supercoiled plasmid) to a protein ligand via polylysine. Ligands are chosen on the basis of the presence of the corresponding ligand receptors on the cell surface of the target cell/tissue type. These ligand-DNA conjugates can be injected directly into the blood if desired and are directed to the target tissue where receptor binding and internalization of the DNA-protein complex occurs. To overcome the problem of intracellular destruction of DNA, co-infection with adenovirus can be included to disrupt endosome function.

The therapy is as follows: patients who carry a mutant KCNJ10 allele are treated with a gene delivery vehicle such that some or all of their cochlear or renal cells receive at least one additional copy of a functional normal KCNJ10 allele, respectively. In this step, the treated individuals have reduced risk of SeSAME to the extent that the effect of the susceptible allele has been countered by the presence of the normal allele.

Peptide Therapy

Peptides which have KCNJ10 activity can be supplied to cells which carry mutant or missing KCNJ10 alleles, respectively. Protein can be produced by expression of the cDNA sequence in bacteria, for example, using known expression vectors. Alternatively, KCNJ10 polypeptide can be extracted from KCNJ10-producing mammalian cells. In addition, the techniques of synthetic chemistry can be employed to synthesize KCNJ10 protein. Any of such techniques can provide the preparation of the present invention which comprises the KCNJ10 protein. The preparation is substantially free of other human proteins. This is most readily accomplished by synthesis in a microorganism or in vitro.

Active KCNJ10 molecules can be introduced into cells by microinjection or by use of liposomes, for example. Alternatively, some active molecules may be taken up by cells, actively or by diffusion. Supply of molecules with KCNJ10 activity should lead to partial reversal of SeSAME. Other molecules with KCNJ10 activity (for example, peptides, drugs or organic compounds) may also be used to effect such a reversal. Modified polypeptides having substantially similar function are also used for peptide therapy.

Combined with certain formulations, peptide which have KCNJ10 activity can be effective intracellular agents. However, in order to increase the efficacy of such peptides, the peptide with KCNJ10 activity can be provided a fusion peptide along with a second peptide which promotes "transcytosis", e.g., uptake of the peptide by epithelial cells. To illustrate, the peptide with KCNJ10 activity can be provided as part of a fusion polypeptide with all or a fragment of the N-terminal domain of the HIV protein Tat, e.g., residues 1-72 of Tat or a smaller fragment thereof which can promote transcytosis. In other embodiments, the peptide with KCNJ10 activity can be provided a fusion polypeptide with all or a portion of the antenopedia III protein.

To further illustrate, the peptide with KCNJ10 activity (or peptidomimetic) can be provided as a chimeric peptide which includes a heterologous peptide sequence ("internalizing peptide") which drives the translocation of an extracellular form of a peptide with KCNJ10 activity across a cell membrane in order to facilitate intracellular localization of the peptide with KCNJ10 activity. In this regard, the therapeutic peptide with KCNJ10 activity binding sequence is one which is active intracellularly. The internalizing peptide, by itself, is capable of crossing a cellular membrane by, e.g., transcytosis, at a relatively high rate. The internalizing peptide is conjugated, e.g., as a fusion protein, to the peptide with KCNJ10 activity. The resulting chimeric peptide is transported into cells at a higher rate relative to the activator polypeptide alone to thereby provide a means for enhancing its introduction into cells to which it is applied.

In one embodiment, the internalizing peptide is derived from the *Drosophila* antennapedia protein, or homologs thereof. The 60 amino acid long homeodomain of the homeo-protein antennapedia has been demonstrated to translocate through biological membranes and can facilitate the translocation of heterologous polypeptides to which it is couples. See for example Derossi et al. (1994) J Biol Chem 269:10444-10450; and Perez et al. (1992) J Cell Sci 102: 717-722. Recently, it has been demonstrated that fragments as small as 16 amino acids long of this protein are sufficient to drive internalization. See Derossi et al. (1996) J Biol Chem 271:18188-18193.

The present invention contemplates a peptide with KCNJ10 activity or peptidomimetic sequence as described herein, and at least a portion of the Antennapedia protein (or homolog thereof) sufficient to increase the transmembrane transport of the chimeric protein, relative to the peptide with KCNJ10 activity or peptidomimetic, by a statistically significant amount.

Another example of an internalizing peptide is the HIV transactivator (TAT) protein. This protein appears to be divided into four domains (Kuppuswamy et al. (1989) Nucl. Acids Res. 17:3551-3561). Purified TAT protein is taken up by cells in tissue culture (Frankel and Pabo, (1989) Cell, 55:1189-1193), and peptides, such as the fragment corresponding to residues 37-62 of TAT, are rapidly taken up by cell in vitro (Green and Loewenstein, (1989) Cell 55:1179-1188). The highly basic region mediates internalization and targeting of the internalizing moiety to the nucleus (Ruben et al., (1989) J. Virol. 63:1-8).

Another exemplary transcellular polypeptide can be generated to include a sufficient portion of mastoparan (T. Higashijima et al., (1990) J. Biol. Chem. 265:14176) to increase the transmembrane transport of the chimeric protein.

While not wishing to be bound by any particular theory, it is noted that hydrophilic polypeptides may be also be physiologically transported across the membrane barriers by coupling or conjugating the polypeptide to a transportable peptide which is capable of crossing the membrane by receptor-mediated transcytosis. Suitable internalizing peptides of this type can be generated using all or a portion of, e.g., a histone, insulin, transferrin, basic albumin, prolactin and insulin-like growth factor I (IGF-I), insulin-like growth factor II (IGF-II) or other growth factors. For instance, it has been found that an insulin fragment, showing affinity for the insulin receptor on capillary cells, and being less effective than insulin in blood sugar reduction, is capable of transmembrane transport by receptor-mediated transcytosis and can therefore serve as an internalizing peptide for the subject transcellular peptides and peptidomimetics. Preferred growth factor-derived internalizing peptides include EGF (epidermal growth factor)-derived peptides, such as CMHIESLDSYTC (SEQ ID NO:15) and CMYIEALDKYAC (SEQ ID NO:16); TGF-beta (transforming growth factor beta)-derived peptides; peptides derived from PDGF (platelet-derived growth factor) or PDGF-2; peptides derived from IGF-I (insulin-like growth factor) or IGF-II; and FGF (fibroblast growth factor)-derived peptides.

Another class of translocating/internalizing peptides exhibits pH-dependent membrane binding. For an internalizing peptide that assumes a helical conformation at an acidic pH, the internalizing peptide acquires the property of amphiphilicity, e.g., it has both hydrophobic and hydrophilic interfaces. More specifically, within a pH range of approximately 5.0-5.5, an internalizing peptide forms an alpha-helical, amphiphilic structure that facilitates insertion of the moiety into a target membrane. An alpha-helix-inducing acidic pH environment may be found, for example, in the low pH environment present within cellular endosomes. Such internalizing peptides can be used to facilitate transport of peptide with KCNJ10 activity and peptidomimetics, taken up by an endocytic mechanism, from endosomal compartments to the cytoplasm.

A preferred pH-dependent membrane-binding internalizing peptide includes a high percentage of helix-forming residues, such as glutamate, methionine, alanine and leucine. In addition, a preferred internalizing peptide sequence includes ionizable residues having pKa's within the range of pH 5-7, so that a sufficient uncharged membrane-binding domain will be present within the peptide at pH 5 to allow insertion into the target cell membrane.

A particularly preferred pH-dependent membrane-binding internalizing peptide in this regard is aa1-aa2-aa3-EAALA(EALA)4-EALEALAA-amide, which represents a modification of the peptide sequence of Subbarao et al. (Biochemistry 26:2964, 1987). Within this peptide sequence, the first amino acid residue (aa1) is preferably a unique residue, such as cysteine or lysine, that facilitates chemical conjugation of the internalizing peptide to a targeting protein conjugate. Amino acid residues 2-3 may be selected to modulate the affinity of the internalizing peptide for different membranes. For instance, if both residues 2 and 3 are lys or arg, the internalizing peptide will have the capacity to bind to membranes or patches of lipids having a negative surface charge. If residues 2-3 are neutral amino acids, the internalizing peptide will insert into neutral membranes.

Yet other preferred internalizing peptides include peptides of apo-lipoprotein A-1 and B; peptide toxins, such as melittin, bombolittin, delta homolysin and the pardaxins; antibiotic peptides, such as alamethicin; peptide hormones, such as calcitonin, corticotrophin releasing factor, beta endorphin, glucagon, parathyroid hormone, pancreatic polypeptide; and peptides corresponding to signal sequences of numerous secreted proteins. In addition, exemplary internalizing peptides may be modified through attachment of substituents that enhance the alpha-helical character of the internalizing peptide at acidic pH.

Yet another class of internalizing peptides suitable for use within the present invention include hydrophobic domains that are "hidden" at physiological pH, but are exposed in the low pH environment of the target cell endosome. Upon pH-induced unfolding and exposure of the hydrophobic domain, the moiety binds to lipid bilayers and effects translocation of the covalently linked polypeptide into the cell cytoplasm. Such internalizing peptides may be modeled after sequences identified in, e.g., *Pseudomonas* exotoxin A, clathrin, or Diphtheria toxin.

Pore-forming proteins or peptides may also serve as internalizing peptides herein. Pore-forming proteins or peptides may be obtained or derived from, for example, C9 complement protein, cytolytic T-cell molecules or NK-cell molecules. These moieties are capable of forming ring-like structures in membranes, thereby allowing transport of attached polypeptide through the membrane and into the cell interior.

Mere membrane intercalation of an internalizing peptide may be sufficient for translocation of the peptide with KCNJ10 activity or peptidomimetic, across cell membranes. However, translocation may be improved by attaching to the internalizing peptide a substrate for intracellular enzymes (i.e., an "accessory peptide"). It is preferred that an accessory peptide be attached to a portion(s) of the internalizing peptide that protrudes through the cell membrane to the cytoplasmic face. The accessory peptide may be advantageously attached to one terminus of a translocating/internalizing moiety or anchoring peptide. An accessory moiety of the present invention may contain one or more amino acid residues. In one embodiment, an accessory moiety may provide a substrate for cellular phosphorylation (for instance, the accessory peptide may contain a tyrosine residue).

An exemplary accessory moiety in this regard would be a peptide substrate for N-myristoyl transferase, such as GNAAAARR (SEQ ID NO:17) (Eubanks et al., in: Peptides, Chemistry and Biology, Garland Marshall (ed.), ESCOM, Leiden, 1988, pp. 566-69) In this construct, an internalizing peptide would be attached to the C-terminus of the accessory peptide, since the N-terminal glycine is critical for the accessory moiety's activity. This hybrid peptide, upon attachment to an E2 peptide or peptidomimetic at its C-terminus, is N-myristylated and further anchored to the target cell membrane, e.g., it serves to increase the local concentration of the peptide at the cell membrane.

To further illustrate use of an accessory peptide, a phosphorylatable accessory peptide is first covalently attached to the C-terminus of an internalizing peptide and then incorporated into a fusion protein with a peptide with KCNJ10 activity or peptidomimetic. The peptide component of the fusion protein intercalates into the target cell plasma membrane and, as a result, the accessory peptide is translocated across the membrane and protrudes into the cytoplasm of the target cell. On the cytoplasmic side of the plasma membrane, the accessory peptide is phosphorylated by cellular kinases at neutral pH. Once phosphorylated, the accessory peptide acts to irreversibly anchor the fusion protein into the membrane. Localization to the cell surface membrane can enhance the translocation of the polypeptide into the cell cytoplasm.

Suitable accessory peptides include peptides that are kinase substrates, peptides that possess a single positive charge, and peptides that contain sequences which are glycosylated by membrane-bound glycotransferases. Accessory peptides that are glycosylated by membrane-bound glycotransferases may include the sequence x-NLT-x, where "x" may be another peptide, an amino acid, coupling agent or hydrophobic molecule, for example. When this hydrophobic tripeptide is incubated with microsomal vesicles, it crosses vesicular membranes, is glycosylated on the luminal side, and is entrapped within the vesicles due to its hydrophilicity (C. Hirschberg et al., (1987) Ann. Rev. Biochem. 56:63-87). Accessory peptides that contain the sequence x-NLT-x thus will enhance target cell retention of corresponding polypeptide.

In another embodiment of this aspect of the invention, an accessory peptide can be used to enhance interaction of the peptide with KCNJ10 activity or peptidomimetic with the target cell. Exemplary accessory peptides in this regard include peptides derived from cell adhesion proteins containing the sequence "RGD", or peptides derived from laminin containing the sequence CDPGYIGSRC (SEQ ID NO:17). Extracellular matrix glycoproteins, such as fibronectin and laminin, bind to cell surfaces through receptor-mediated processes. A tripeptide sequence, RGD, has been identified as necessary for binding to cell surface receptors. This sequence is present in fibronectin, vitronectin, C3bi of complement, von-Willebrand factor, EGF receptor, transforming growth factor beta, collagen type I, lambda receptor of *E. Coli*, fibrinogen and Sindbis coat protein (E. Ruoslahti, Ann. Rev. Biochem. 57:375413, 1988). Cell surface receptors that recognize RGD sequences have been grouped into a superfamily of related proteins designated "integrins". Binding of "RGD peptides" to cell surface integrins will promote cell-surface retention, and ultimately translocation, of the polypeptide.

As described above, the internalizing and accessory peptides can each, independently, be added to the peptide with KCNJ10 activity or peptidomimetic by either chemical cross-linking or in the form of a fusion protein. In the instance of fusion proteins, unstructured polypeptide linkers can be included between each of the peptide moieties.

In general, the internalization peptide will be sufficient to also direct export of the polypeptide. However, where an accessory peptide is provided, such as an RGD sequence, it may be necessary to include a secretion signal sequence to direct export of the fusion protein from its host cell. In preferred embodiments, the secretion signal sequence is located at the extreme N-terminus, and is (optionally) flanked by a proteolytic site between the secretion signal and the rest of the fusion protein.

In certain instances, it may also be desirable to include a nuclear localization signal as part of the peptide with KCNJ10 activity.

In the generation of fusion polypeptides including a peptide with KCNJ10 activity, it may be necessary to include unstructured linkers in order to ensure proper folding of the various peptide domains. Many synthetic and natural linkers are known in the art and can be adapted for use in the present invention, including the $(Gly_3Ser)_4$ linker.

F. Transgenic Non-human Mammals

Animals for testing therapeutic agents can be selected after mutagenesis of whole animals or after treatment of germline cells or zygotes. Such treatments include insertion of mutant KCNJ10 alleles, usually from a second animal species, as well as insertion of disrupted homologous genes. Alternatively, the endogenous KCNJ10 gene of the animals may be disrupted by insertion or deletion mutation or other genetic alterations using conventional techniques (Shinkai et al., 1992, Cell 68:855-867; Mombaerts et al., 1992, Cell 68:869-877; Philpott et al., 1992, Science 256:1448-1452; Snouwaert et al., 1992, Science 257:1083-1088; Donehower et al., 1992, Nature 356:215-221). After test substances have been administered to the animals, the presence of SeSAME syndrome phenotype is assessed. If the test substance prevents or suppresses the appearance of SeSAME syndrome, then the test substance is a candidate therapeutic agent for treatment of SeSAME syndrome. These animal models provide an extremely important testing vehicle for potential therapeutic products.

Pharmaceutical Compositions of the Invention

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions that are useful in the methods of the invention may be prepared, packaged, or sold in formulations suitable for ophthalmic, oral, rectal, vaginal, parenteral, topical, pulmonary, intranasal, buccal, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Other active agents useful in the treatment of fibrosis include anti-inflammatories, including corticosteroids, and immunosuppressants.

Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intraocular, intravitreal, subcutaneous, intraperitoneal, intramuscular, intrasternal injection, intratumoral, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, Pa.), which is incorporated herein by reference.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

The materials and methods employed in the experiments disclosed herein are now described.

Patient Recruitment and DNA Preparation

The study protocol was approved by the Yale Human Investigation Committee. Consent for participation was obtained in accordance with Institutional Review Board standards. Patients were referred for studies of hypokalemic salt-losing nephropathies, and kindreds were chosen for further analysis by the presence of seizures, ataxia, and hearing impairment. Genomic DNA was prepared from venous blood of kindred members by standard procedures.

Genotyping

The samples were genotyped on the Illumina Human CNV370-Duo (for 441-1) and Illumina Human 610-Quad (for 404-1, 632-1, and 632-2) beadchips at the W.M. Keck Facility at Yale University. Sample processing and labeling were performed using the manufacturer's instructions. Mean call rate of the 4 samples was 99.50%.

Mapping Homozygous and IBD Intervals

Because the genotype data from 441-1 and 404-1 originated from different arrays, the data were compared to identify 346,073 shared single nucleotide polymorphisms (SNPs) to be analyzed by homozygosity mapping. Analysis of homozygous segments across 22 autosomes was performed using the "Runs of homozygosity" tool implemented in a whole genome association analysis toolkit (PLINK, v1.05, <<http://pngu.mgh.harvard.edu/purcell/plink>>). A fixed threshold of 200 consecutive SNPs and 2 Mb in length was selected, and 1 heterozygous SNP within a segment was allowed.

To check the IBD shared regions between the affected siblings, the genotype data from 632-1 and 632-2 were directly compared. Missing calls were discarded. Fixed thresholds of 200 consecutive SNPs and 1 Mb in length were used to call IBD segments.

DNA Sequencing

The following primer pair was used to amplify the coding exon of KCNJ10 using as a template genomic DNA of disease family members or controls. PCR generated a product with a size of 1,325 bp:

```
KCNJ10_F:
                                   (SEQ ID NO: 17)
5'-CATGGGGTGAGGGTTAGGAG-3'

KCNJ10_R:
                                   (SEQ ID NO: 18)
5'-GGGAGTGGAGGATGGGTG-3'
```

Products were analyzed via gel electrophoresis, and purified amplicons were sequenced using the following primers:

```
KCNJ10_F, KCNJ10_R, KCNJ10MF:
                                   (SEQ ID NO: 19)
5'-CGGGCTGAGACCATTCGTTTC-3'

KCNJ10MR:
                                   (SEQ ID NO: 20)
5'-AGGCTTTTGCGCATATTGGAAC-3'
```

Disease-causing mutations were confirmed by at least 2 independent sequences from different primers. In addition, in the 2 kindreds in which affected subjects were apparent compound heterozygotes, the coding region was amplified and cloned using the TOPO TA Cloning Kit (Invitrogen), and independent clones from each patient were sequenced to determine whether the identified mutations were in cis or trans.

Orthologs and Paralogs

Full-length orthologous and paralogous protein sequences from vertebrate and invertebrate species (including rodents, bird, fish, and fly) were extracted from GenBank. Orthologs were confirmed based on database identity of annotation or in a BLAST of the protein sequence against the human protein sequence, with the requirement that human KCNJ10 be the top hit. If an ortholog could not be identified, a paralog was studied. Protein sequences were aligned using the ClustalW algorithm. Gen-Bank accession numbers were: NP_002232.2 (human KCNJ10), NP_001034573.1 (mouse KCNJ10), XP_425554.2 (chicken paralog), NP_001072312.1 (frog KCNJ10), XP_001342993.1 (zebrafish ortholog), and NP_001097884.1 (fly paralog).

The results of the experiments presented in this Example are now described.

Example 1

Case Report: Kindred 441

The index case, patient 441-1, is a 24-year-old female of Afghan ancestry who is the fifth of 6 offspring of healthy first-cousins. Generalized seizures began at 3 months, occurring several times daily. Seizures were controlled initially with phenobarbital, and later diphenylhydantoin. Sitting was first demonstrated at age 1 year, crawling at age 20 months. At age 5 years 7 months, the patient presented for evaluation of developmental delay. At this time, she was unable to walk or speak. Physical examination was notable for atrophy of the lower extremities without contractures. Motor strength was slightly reduced in the upper, but markedly reduced in the lower extremities. Reflexes were normal. There was marked ataxia. Nerve conduction studies revealed reduced conduction velocity in the left peroneal and left tibial nerves (36 and 37 m/sec, respectively; nl 40-44 m/sec). A muscle and nerve biopsy showed normal muscle other than fiber-type disproportion; there was hypomyelination of the large myelinated nerve fibers in the sural nerve, with moderate progressive axonal neuropathy. Brain MRI showed normal myelination, and was normal with the exception of slightly coarsened frontal sulci. EEG, abdominal ultrasound, and karyotype analysis were normal.

Laboratory evaluation was remarkable for persistent hypokalemia, metabolic alkalosis, and hypomagnesemia (Table 1). Plasma renin activity (PRA) was elevated on repeated measures (8.1 and 7.6 ng/ml per hour, nl<2.8 ng/ml per hour). Twentyfour-hour urinary aldosterone level was elevated (31.3 µg; nl 5.9-17.6) and the $Ca^{2+}$/creatinine ratio was low (0.1 to 0.2 mmol/mmol). The patient was treated with oral potassium replacement, and required 30 meq per day to maintain a $K^+$ level in the normal range. At age 18, progressive hearing loss was noted. Brainstem-evoked response audiometry and pure-tone threshold audiometry were performed, and moderate-to-severe sensorineural hearing loss was documented.

TABLE 1

| Clinical feature | Patient number | | | | |
|---|---|---|---|---|---|
| | 327-1 | 404-1 | 441-1 | 632-1 | 632-2 |
| Ancestry | Great Britain | Turkey | Afghanistan | Canada | Canada |
| Consanguinity | N/A | Yes | Yes | No | No |
| Seizures (age onset, months) | + (N/A) | + (4) | + (3) | + (3) | + (3) |
| Ataxia | + | + | + | + | + |
| Developmental delay | + | + | + | + | + |
| Hearing loss | + | + | + | + | + |
| $K^+$ (mmol/l) | 2.9 | 3.15 | 3.1 | 3.1 | 2.9 |
| $Mg^{2+}$ (mmol/l) | 0.55 | 0.62 | 0.54 | 0.56 | 0.6 |
| $HCO_3^-$ (mmol/l) | 28 | 30 | 29 | 31 | 33 |
| $U_{Ca}/U_{Cr}$ (mmol/mmol) | 0.11 | 0.34 | 0.10 | N/A | 0.26 |
| $U_K/U_{Cr}$ (mmol/mmol) | 38.18 | 24.28 | 21.67 | N/A | 16.18 |
| $U_{Na}/U_{Cr}$ (mmol/mmol) | 19.09 | 25.86 | 32.50 | N/A | 23.86 |

$K^+$, serum potassium, nl 3.5-5 mmol/l;
serum magnesium, nl 0.8-1.2 mmol/l;
$HCO_3^-$, serum bicarbonate, nl 23-26 mmol/l;
$U_{Ca}/U_{Cr}$ urinary calcium/creatinine ratio, nl < 0.4 mmol/mmol);
$U_K/U_{Cr}$ urinary potassium/creatinine ratio nl 6-8 mmol/mmol or 1-1.5 mmol/mmol in hyperkalemia;
$U_{Na}/U_{Cr}$ urinary sodium/creatinine ratio, values are elevated and in the range observed with Gitelman syndrome.

The patient's family history is notable for 2 of 5 siblings with a related disorder, and one spontaneous abortion. The first child, a male, presented with seizures at age 4 months and was never able to walk. He died at age 7 years during a diarrheal illness. The sixth child, a male, presented with seizures and vomiting at age 5 months and was unable to walk until 16 months. He died at 18 months during an intercurrent infection. The other 3 children are healthy.

Definition of a New Clinical Syndrome In the review of 589 subjects referred for evaluation of Gitelman and Bartter syndromes, subjects were recognized from 3 additional kindreds with features similar to patient 441-1. The shared features included early onset seizures, mental retardation, ataxia, hypotonia, and sensorineural hearing loss. Intention tremor was noted in several cases and volume loss of the cerebellum in 2 cases (632-2 and 404-1).

Short stature was notable in 2 affected siblings (632-1 and 632-2), with a final height of 150 cm and 149 cm, respectively. Electrolyte abnormalities featured marked and persistent hypokalemic metabolic alkalosis in the absence of hypertension and striking hypomagnesemia that required electrolyte replacement and, in many cases, use of pharmacologic inhibitors of the epithelial sodium channel or aldosterone antagonists to prevent renal $K^+$ loss. Where available, 24-h urinary electrolyte measurements revealed renal $K^+$ and Mg2+ wasting and high urinary $Na^+$ levels. PRA and aldosterone levels, when measured, were always elevated, and salt craving, enuresis, and polyuria/polydipsia were reported. A summary of the patients' clinical and laboratory findings is provided in Table 1.

Mapping the Disease Locus The recurrent clinical features suggested a previously unrecognized clinical syndrome. Moreover, recurrence of a similar syndrome among siblings in 2 of these kindreds, and its occurrence in the setting of parental consanguinity in 2 kindreds, suggested autosomal recessive transmission.

To attempt to map the underlying disease locus, a genome-wide analysis of linkage was performed in the 3 informative kindreds (2 offspring of first-cousin marriage and 2 affected siblings from unrelated parents). The results demonstrated complete linkage of the putative trait locus to a single chromosome segment, 1q23.2-q23.3, with a lod score of 3.0. The maximum likelihood location is confined to a 2.5-Mb interval extending from 158.1M to 160.6Mbase pairs (FIG. 1A). No other chromosome segment showed linkage in all 3 kindreds. Significantly, the index case (441-1) did not show homozygosity at any of the known loci for Bartter or Gitelman syndrome, and sequencing of these genes revealed no evidence of pathogenic mutations.

Mutations in KCNJ10 The linked interval on chromosome 1 contains 70 well-defined and at least 6 hypothetical genes, none of which has previously been implicated in human disease phenotypes that would explain the features found in these patients. If the disease is caused by mutation in a single gene, it would likely be expressed in the CNS, inner ear, and kidney. KCNJ10, which encodes the inwardly rectifying $K^+$ channel Kir4.1 (also known as BIR10, BIRK1, KAB-2, Kir1.2), KCNJ10 consisting of 2 transmembrane segments and 1 pore, was identified as a strong candidate (FIG. 1B). KCNJ10 has been shown to be expressed in the CNS, cochlea, and distal nephron, and a mouse knockout has a neurological phenotype with many features similar to those seen in our patients.

Available members of the 4 kindreds with this syndrome were screened for KCNJ10 mutations by direct sequencing (FIG. 2). Homozygous missense mutations were found in the 2 consanguineous kindreds, compound heterozygous missense mutations in 1 outbred kindred, and a compound missense/premature termination mutation in 1 kindred. In the compound heterozygous patients, cloning of the coding region on single amplicons confirmed that the 2 mutations identified are in trans. To assess the significance of missense mutations, the KCNJ10 amino acid sequence was compared to orthologs in diverse vertebrate species including mammals, *Xenopus tropicalis*, and zebrafish, and closely related paralogs in chicken and *Drosophila melanogaster*. These species split from a common ancestor ~500 million years ago, and across these species, only 27% of the amino acids were completely conserved. All of the identified mutations occurred at positions that were completely conserved among all vertebrate species and all but one occurred at positions completely conserved through *Drosophila* (see FIG. 2).

Patient 327-1 was compound heterozygous for a nonsense and a missense mutation (see FIG. 2A). The nonsense mutation introduces a premature termination codon at position 199 in the cytoplasmic C terminus. This deletes a PDZ-binding domain that is known to be required for expression of Kir4.1 at the cell surface (Tanemoto et al., 2004, Am. J. Physiol. Renal Physiol. 287:F1148-F1153). This patient also harbors an R65P substitution immediately preceding the first transmembrane domain (FIG. 3).

This position is conserved in a related inward rectifier, Kir2.1, and expression of Kir2.1 containing mutation at this position abolished nearly all detectable whole-cell $K^+$ current when expressed in *Xenopus* oocytes (Lopes et al., 2002, Neuron 34:933-944).

Affected subject 404-1 was homozygous for a C140R missense mutation (see FIG. 2B). C140 is located in the P region near the start of the second transmembrane domain (see FIG. 3). This position is conserved in the related channel ROMK (position C153), and mutation of this residue to either alanine or serine has been shown to abolish ROMK function (Schulte et al., 1998, J. Biol. Chem. 273:34575-34579).

A missense mutation was found in kindred 441, resulting in a T164I substitution (see FIG. 2C). The index case is homozygous for the mutant allele, while both parents are heterozygotes and neither of 2 unaffected siblings are homozygous, providing further support for linkage (total lod score for linkage after inclusion of the 2 unaffected siblings increases to 3.25). Rapedius et al., 2007, Channels 1:327-330, have suggested that T164, which is located in the second transmembrane domain, forms an intra-subunit H-bond with lysine 67 in the first transmembrane domain, and that this interaction is critical for gating of the channel. Because this lysine is predicted to form an H-bond not only with the backbone carbonyl of Thr-164, but also with its side chain oxygen, mutation to isoleucine would eliminate this interaction and potentially affect the gating properties of the channel in response to pH and phosphatidylinositol 4,5-bisphosphate (PIP2).

Finally, in kindred 632, both affected siblings are compound heterozygotes for A167V and R297C mutations (see FIG. 2D). A167 is located at the end of the second transmembrane domain, close to the constriction at the inner helix bundle that likely corresponds to the gate of the channel (Nishida et al., 2007, EMBO J. 26:4005-4015). R297 lies in a highly conserved segment in the C terminus of the protein (see FIG. 3). Notably, a mutation at the residue corresponding to R297 has been found in ROMK (R292W), and was implicated as a loss of function mutation in Bartter's syndrome type II (Ji et al., 2008, Nature Genetics 40:592-599). Similarly, mutation of the conserved position in Kir2.1 (R312) to glutamine greatly reduces whole-cell currents and produces weakened interaction with PIP2 (Lopes et al., 2002, Neuron 34:933-944).

None of the identified mutations are in the dbSNP database. Resequencing of KCNJ10 in 103 unrelated Caucasian subjects did not identify any of these mutations and no missense variants at conserved residues were identified in any of the 206 alleles studied.

Thus, a previously unrecognized human syndrome featuring prominent neurological and renal features is described herein. In all 4 kindreds studied, the disease co-segregates with rare mutations in KCNJ10. The finding of 6 independent, rare KCNJ10 mutations in 4 families that significantly co-segregate with the disease under a recessive model and which show specificity for the disease provides genetic evidence that these mutations are the cause of this syndrome. The fact that many of the amino acids altered by mutations are conserved in other members of the inward rectifier $K^+$ channel family and have been shown to be essential for their normal function lends strong support for the functional significance of these mutations. The genetic and biochemical evidence support these mutations being a genetic loss of function. Several of the identified mutations are likely to affect channel activity via altered interaction with PIP2. Numerous functional studies in closely related inward rectifier potassium channels have underlined the crucial role of PIP2 to sustain activity of these channels (Lopes et al., 2002, Neuron 34:933-944).

PIP2 is a membrane-delimited second messenger, and binds proteins through electrostatic interactions at basic amino acids. These sites have been defined in many members of this gene family, and mutations at PIP2 binding sites have been implicated in other channelopathies, including Bartter's syndrome, caused by ROMK mutations, and Andersen's syndrome, caused by mutations in KCNJ2 encoding Kir2.1. A similar mechanism likely accounts for loss of function in at least 2 of the mutations identified here (R65P and R297C), which lie at inferred PIP2 binding sites. A third residue (T164) has been implicated in an H-bond between the 2 transmembrane helices, which again plays an important role in the channel's gating in response to PIP2 and pH (Rapedius et al., 2007, Channels 1:327-330).

Significant prior work has been done on KCNJ10; it appears to function as a heteromultimer at least in some tissues. The currents observed in native tissues have properties most similar to those produced by coexpression of Kir4.1 and Kir5.1 in heterologous systems, and immunofluorescence studies support colocalization of these gene products (Lachheb et al., 2008, Am. J. Physiol. Renal Physiol. 294:F1398-F1407; Lourdel et al., 2002, J. Physiol.

538:391-404). This observation raises the question of whether a related syndrome might be caused by mutation in Kir5.1.

In addition, mice with both constitutional and selective astrocyte knockout of KCNJ10 have been produced, with a resultant phenotype that is strikingly similar to the patients we describe (Djukic et al., 2007, J. Neuroscience 27:11354-11365; Kofuji et al., 2000, J. Neuroscience 20:5733-5740; Neusch et al., 2001, J. Neuroscience 21:5429-5438). The animals develop motor coordination deficits with awkward and jerky movements and loss of balance, and drag the hind limbs. They also suffer seizures and have sensorineural hearing loss (Djukic et al., 2007, J. Neuroscience 27:11354-11365; Rozengurt et al., 2003, Hearing Res. 177:71-80). Additionally, mice with the constitutional knockout appear to have a salt-wasting phenotype; however, this has not been well defined. These findings strongly support the mutations identified herein as causing loss of function.

In the brain, KCNJ10 appears to be primarily expressed in glial cells (Takumi et al., 1995, J. Biol. Chem. 270:16339-16346), specifically in astrocytes surrounding synapses and blood vessels, and oligodendrocyte cell bodies (Djukic et al., 2007, J. Neuroscience 27:11354-11365). Neuronal repolarization after excitatory stimuli is achieved via efflux of $K^+$, and it has been proposed that KCNJ10 plays a role in astrocyte clearance of this $K^+$ via "spatial buffering." If the resting membrane potential is set by KCNJ10, a local increase in extracellular $K^+$ concentration close to the synapse would favor $K^+$ uptake by astrocytes, and efflux at remote positions that have lower extracellular $K^+$ concentrations (i.e., the rise in extracellular $K^+$ would cause the local glial EK to be less negative than the aggregate cellular membrane potential). Loss of KCNJ10 would thus result in astrocyte depolarization [which is seen in astrocytes from KCNJ10-deficient mice (Djukic et al., 2007, J. Neuroscience 27:11354-11365)], loss of this $K^+$ clearance function, prolonged neuronal depolarization, and reduced seizure threshold. Similarly, astrocyte depolarization would reduce clearance of the excitatory neurotransmitter glutamate, which would also reduce seizure threshold [reduced glutamate uptake is also seen in astrocytes from KCNJ10-deficient mice (Djukic et al., 2007, J. Neuroscience 27:11354-11365)]. While other mechanisms (activities of the $Na^+$—$K^+$-ATPase or Na—K—Cl co-transporters) are also potentially involved in the regulation of synaptic $K^+$ (Kofuji et al., 2004, Neuroscience 129:1045-1056), the observed seizure activity in humans deficient for KCNJ10 indicates an important role of this channel in prevention of seizure activity.

Finally, it is of interest that common variation in the KCNJ10 gene has been suggested to be associated with seizure susceptibility (Buono et al., 2004, Epilepsy Res. 58:175-183), however, the functional significance of the implicated variants and the replicability of this finding has not been established.

Kir4.1 is expressed in intermediate cells of the stria vascularis (Ando et al., 1999, Cell. Tissue Res. 298:179-183), where it is believed to contribute to the generation of the endocochlear potential, as demonstrated by hearing loss in the KCNJ10-knockout mouse (Rozengurt et al., 2003, Hearing Res. 177:71-80) and the patients described herein. Both mice and humans with KCNJ10 mutations have marked ataxia and there is also lower extremity weakness in the mouse and some affected humans. Whether the ataxia is cerebellar in origin or sensory (due to loss of proprioception) has not been established and is hard to assess because of cognitive impairment of affected subjects. Intention tremor and volume loss in the cerebellum, as seen in some cases, suggest cerebellar involvement. However, peripheral sensory neuropathy might also contribute to the ataxia.

KCNJ10-deficient mice exhibit striking pathology of the spinal cord with dysmyelination, hypomyelination, and axonal degeneration along with massive spongiform vacuolation. MRI demonstrates marked white-matter pathology in the spinal cord and brainstem, while cerebellum, midbrain, and cortical regions seem unaffected at P12. It thus appears that Kir4.1 is required for oligodendrocyte development, and at least spinal cord myelination (Neusch et al., 2001, J. Neuroscience 21:5429-5438). The observation that sural nerve biopsy in one of our patients showed hypomyelination suggests a possible role for KCNJ10 in the peripheral nervous system as well, and Kir4.1 has been shown to be expressed in satellite cells (Hibino et al., 1999, Am. J. Physiol. 277:C638-C644).

The distinct electrolyte abnormalities in our patients add considerable new insight into the role of KCNJ10 in renal electrolyte homeostasis. The KCNJ10 gene product has been immunolocalized in the kidney. In contrast to the apical $K^+$ channels (e.g., KCNJ1 encoding ROMK and KCNMA1 encoding Maxi-K) that mediate $K^+$ secretion in the distal nephron, Kir4.1 localizes to the basolateral membranes of epithelia of the distal convoluted tubule, connecting tubule, and initial collecting tubule (Ito et al., 1996, FEBS Lett. 388:11-15). Weak immunoreactivity in the thick ascending limb of Henle has also been described (Tanemoto et al., 2004, Am. J. Physiol. Renal Physiol. 287:F1148-F1153). Patients with KCNJ10 deficiency display hypokalemia, metabolic alkalosis, hypomagnesemia and, where studied, elevated levels of renin and aldosterone.

The high renin and aldosterone, along with normal blood pressure, hypokalemia, and metabolic alkalosis strongly point to salt wasting as an incipient event in the renal features, and the reports of salt craving, polyuria, and enuresis are consistent with this. Moreover, these patients have elevated urinary sodium/creatinine ratios in the range seen in patients with Gitelman syndrome (Cruz et al., 2001, Nypertension 37:1458-1464). Loss of KCNJ10 function can result in salt wasting by impairing the activity of the $Na^+$—$K^+$-ATPase. The $Na^+$—$K^+$-ATPase is on the basolateral membrane, and its activity is required for $Na^+$ reabsorption, pumping $Na^+$ out of epithelia and $K^+$ in against their electrochemical potentials. Because very large amounts of filtered $Na^+$ must be reabsorbed by renal epithelia, the $K^+$ that enters the epithelial cell must be recycled to the interstitium by basolateral $K^+$ channels to allow continued $Na^+$ reabsorption. Without this mechanism, the $Na^+$—$K^+$-ATPase could be inhibited and the potential across the basolateral membrane diminished. This diminished negative intracellular potential will also attenuate the electrical gradient for the efflux of (FIG. 4B). The combined effects will produce impaired Na—Cl reabsorption.

Because much is known about the consequences of inhibition of salt reabsorption in different nephron segments (Nijenhuis et al., 2005, J. Clin. Invest. 115:1651-1658; Schultheis et al., 1998, J. Biol. Chem. 273:29150-19155), inferences may be made about where the effects of KCNJ10 deficiency are impairing salt reabsorption. The only site at which inhibition of salt reabsorption produces hypomagnesemia with reduced urinary calcium is the distal convoluted tubule. In contrast, loss of salt reabsorption in the thick ascending limb produces marked hypercalciuria and little hypomagnesemia (Simon et al., 1996, Nature Genetics 13:183-188), while loss of ENaC activity in the collecting duct produces hyperkalemia and acidosis rather than hypokalemia and alkalosis (Chang et al., 1996, Nature Genetics 12:248-253). Consequently, it is highly likely that impaired salt reabsorption in the DCT plays a prominent role in this syndrome. Because epithelial cells of the DCT have the greatest per-cell Na$^+$ reabsorption and energy demand (Reilly et al., 2000, Physiol. Rev. 80:277-313), it is possible that sodium pump activity in other nephron segments is also affected, but that the effect in the DCT predominates.

These considerations suggest an integrated model in which loss of Kir4.1 activity impairs salt reabsorption in the distal convoluted tubule (see FIGS. 4A-4B). Because salt reabsorption in the DCT comprises ~7% of the filtered load, loss of salt reabsorption here induces salt wasting, which activates the rennin-angiotensin system, increasing Na$^+$ reabsorption by the ENaC in the connecting tubule and collecting duct. This increases the electrical driving force for both K$^+$ and H$^+$ secretion, resulting in hypokalemia and metabolic alkalosis. As described above, loss of salt reabsorption in the DCT is also known to produce hypocalciuria and hypomagnesemia. While these renal electrolyte defects seem relatively mild, it is noteworthy that 2 siblings with this syndrome have died in the setting of diarrheal or other intercurrent infections, suggesting impaired ability to defend volume homeostasis under stress.

Little is known about the genes that underlie the most prevalent forms of epilepsy. In the last decade, gene defects have been identified that cause rare Mendelian forms of idiopathic epilepsy syndromes, and most of these genes encode ion channels, consistent with their role in maintaining membrane potential and regulating neuronal excitability (Weber et al., 2008, Dev. Med. Child. Neurol. 50:648-654).

It will be interesting to determine the prevalence of epilepsy caused by mutations in the KCNJ10 gene. In addition to the characteristic neurological features (developmental delay, ataxia, and hearing impairment), a simple blood test might help to screen for such patients, as all patients in this report presented with significant hypokalemia and hypomagnesemia.

These human findings raise the possibility that Kir4.1 could be a useful target for pharmacologic manipulation. Similar to the recently developed anticonvulsant drug retigabine, which opens KCNQ2/3 channels (Rundfeldt et al., 2000, Neurosci. Lett. 282:73-76), a Kir4.1 activator might have anticonvulsant effects; nonetheless, the expression of Kir4.1 in several tissues raises the question of whether there might be pleiotropic effects that could limit utility.

In summary, the data described herein define a unique autosomal, recessive syndrome, named SeSAME syndrome, characterized by seizures, sensorineural deafness, ataxia, mental retardation, and electrolyte imbalance (hypokalemic alkalosis and hypomagnesemia), and demonstrate that it is caused by mutations in KCNJ10.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of detecting a mutation in a KCNJ10 nucleic acid in a bodily sample from a subject, said method comprising:
  performing an allele specific detection assay on a KCNJ10 nucleic acid in said bodily sample obtained from said subject, wherein said allele specific detection assay comprises contacting the KCNJ10 nucleic acid with a detectably labeled oligonucleotide under high stringency hybridization conditions, wherein the detectably labeled oligonucleotide is substantially complementary to a KCNJ10 nucleic acid sequence comprising a KCNJ10 mutation, and wherein the KCNJ10 nucleic acid sequence comprises a sequence selected from the group consisting of SEQ ID NOs: 3-8, and
  detecting whether hybridization of said oligonucleotide with said KCNJ10 nucleic acid in said bodily sample takes place,
  whereby, if hybridization of said oligonucleotide with said KCNJ10 nucleic acid in said bodily sample is detected, a mutation in said KCNJ10 nucleic acid in said bodily sample from said subject is detected.

2. The method of claim 1, wherein said bodily sample is selected from the group consisting of a tissue, a cell and a bodily fluid.

3. The method of claim 2, wherein said bodily fluid comprises maternal serum or amniotic fluid.

4. The method of claim 1, wherein said KCNJ10 mutation is selected from the group consisting of a nonsense mutation, a missense mutation, and a truncated coding mRNA.

5. A method of detecting a mutation in a KCNJ10 nucleic acid, the method comprising:
  (a) contacting a KCNJ10 nucleic acid with a probe under high stringency hybridization conditions, wherein said detectably labeled probe specifically binds to a portion of a KCNJ10 nucleic acid that encodes R65P, relative to SEQ ID NO: 2,
  (b) detecting whether hybridization of said detectably labeled probe with said KCNJ10 nucleic acid takes place; and
  (c) identifying a mutation in the KCNJ10 nucleic acid when hybridization is detected in step (b).

6. The method of claim 5, wherein said probe is detectably labeled.

7. The method of claim 5, wherein said KCNJ10 nucleic acid is from a bodily sample selected from the group consisting of a tissue, a cell and a bodily fluid.

8. The method of claim 6, wherein said bodily sample is from a human subject at risk of developing SeSAME syndrome.

* * * * *

SEQUENCE LISTING

<160> NUMBER OF SEQ ID NOS: 20

<210> SEQ ID NO 1
<211> LENGTH: 1140
<212> TYPE: DNA
<213> ORGANISM: Homo sapiens

<400> SEQUENCE: 1

```
atgacgtcag ttgccaaggt gtattacagt cagaccactc agacagaaag ccggcccta      60 atgggcccag ggatacgacg gcggagagtc ctgacaaaag atggtcgcag caacgtgaga    120
atggagcaca ttgccgacaa gcgcttcctc tacctcaagg acctgtggac aaccttcatt    180
gacatgcagt ggcgctacaa gcttctgctc ttctctgcga cctttgcagg cacatggttc    240
ctctttggcg tggtgtggta tctggtagct gtggcacatg gggacctgct ggagctggac    300
cccccggcca accacacccc ctgtgtggta caggtgcaca cactcactgg agccttcctc    360
ttctcccttg aatcccaaac caccattggc tatggcttcc gctacatcag tgaggaatgt    420
ccactggcca ttgtgcttct tattgcccag ctggtgctca ccaccatcct ggaaatcttc    480
atcacaggta ccttcctggc gaagattgcc cggcccaaga agcgggctga gaccattcgt    540
ttcagccagc atgcagttgt ggcctcccac aatggcaagc cctgcctcat gatccgagtt    600
gccaatatgc gcaaaagcct cctcattggc tgccaggtga caggaaaact gcttcagacc    660
caccaaacca aggaagggga gaacatccgg ctcaaccagg tcaatgtgac tttccaagta    720
gacacagcct ctgacagccc cttccttatt ctaccccta ccttctatca tgtggtagat    780
gagaccagtc ccttgaaaga tctccctctt cgcagtggtg agggtgactt tgagctggtg    840
ctgatcctaa gtgggacagt ggagtccacc agtgccacct gtcaggtgcg cacttcctac    900
```

```
ctgccagagg agatcctttg gggctacgag ttcacacctg ccatctcact gtcagccagt    960
ggtaaataca tagctgactt tagccttttt gaccaagttg tgaaagtggc ctctcctagt   1020
ggcctccgtg acagcactgt acgctacgga gaccctgaaa agctcaagtt ggaggagtca   1080
ttaagggagc aagctgagaa ggagggcagt gcccttagtg tgcgcatcag caatgtctga   1140
```

<210> SEQ ID NO 2
<211> LENGTH: 379
<212> TYPE: PRT
<213> ORGANISM: Homo sapiens

<400> SEQUENCE: 2

```
Met Thr Ser Val Ala Lys Val Tyr Tyr Ser Gln Thr Thr Gln Thr Glu
1               5                   10                  15

Ser Arg Pro Leu Met Gly Pro Gly Ile Arg Arg Arg Arg Val Leu Thr
            20                  25                  30

Lys Asp Gly Arg Ser Asn Val Arg Met Glu His Ile Ala Asp Lys Arg
        35                  40                  45

Phe Leu Tyr Leu Lys Asp Leu Trp Thr Thr Phe Ile Asp Met Gln Trp
    50                  55                  60

Arg Tyr Lys Leu Leu Phe Ser Ala Thr Phe Ala Gly Thr Trp Phe
65                  70                  75                  80

Leu Phe Gly Val Val Trp Tyr Leu Val Ala Val Ala His Gly Asp Leu
                85                  90                  95

Leu Glu Leu Asp Pro Pro Ala Asn His Thr Pro Cys Val Val Gln Val
            100                 105                 110

His Thr Leu Thr Gly Ala Phe Leu Phe Ser Leu Glu Ser Gln Thr Thr
        115                 120                 125

Ile Gly Tyr Gly Phe Arg Tyr Ile Ser Glu Glu Cys Pro Leu Ala Ile
    130                 135                 140

Val Leu Leu Ile Ala Gln Leu Val Leu Thr Thr Ile Leu Glu Ile Phe
145                 150                 155                 160

Ile Thr Gly Thr Phe Leu Ala Lys Ile Ala Arg Pro Lys Lys Arg Ala
                165                 170                 175

Glu Thr Ile Arg Phe Ser Gln His Ala Val Val Ala Ser His Asn Gly
            180                 185                 190

Lys Pro Cys Leu Met Ile Arg Val Ala Asn Met Arg Lys Ser Leu Leu
        195                 200                 205

Ile Gly Cys Gln Val Thr Gly Lys Leu Leu Gln Thr His Gln Thr Lys
    210                 215                 220

Glu Gly Glu Asn Ile Arg Leu Asn Gln Val Asn Val Thr Phe Gln Val
225                 230                 235                 240

Asp Thr Ala Ser Asp Ser Pro Phe Leu Ile Leu Pro Leu Thr Phe Tyr
                245                 250                 255

His Val Val Asp Glu Thr Ser Pro Leu Lys Asp Leu Pro Leu Arg Ser
            260                 265                 270

Gly Glu Gly Asp Phe Glu Leu Val Leu Ile Leu Ser Gly Thr Val Glu
        275                 280                 285

Ser Thr Ser Ala Thr Cys Gln Val Arg Thr Ser Tyr Leu Pro Glu Glu
    290                 295                 300

Ile Leu Trp Gly Tyr Glu Phe Thr Pro Ala Ile Ser Leu Ser Ala Ser
305                 310                 315                 320

Gly Lys Tyr Ile Ala Asp Phe Ser Leu Phe Asp Gln Val Val Lys Val
                325                 330                 335
```

```
Ala Ser Pro Ser Gly Leu Arg Asp Ser Thr Val Arg Tyr Gly Asp Pro
            340                 345                 350

Glu Lys Leu Lys Leu Glu Glu Ser Leu Arg Glu Gln Ala Glu Lys Glu
        355                 360                 365

Gly Ser Ala Leu Ser Val Arg Ile Ser Asn Val
    370                 375

<210> SEQ ID NO 3
<211> LENGTH: 1140
<212> TYPE: DNA
<213> ORGANISM: Homo sapiens

<400> SEQUENCE: 3
atgacgtcag ttgccaaggt gtattacagt cagaccactc agacagaaag ccggccccta        60
atgggcccag ggatacgacg gcggagagtc ctgacaaaag atggtcgcag caacgtgaga       120
atggagcaca ttgccgacaa gcgcttcctc tacctcaagg acctgtggac aaccttcatt       180
gacatgcagt ggcccuacaa gcttctgctc ttctctgcga cctttgcagg cacatggttc       240
```

| | |
|---|---|
| atcacaggta ccttcctggc gaagattgcc cggcccaaga agcgggctga gaccattcgt | 540 |
| ttcagccagc atgcagttgt ggcctcccac aatggcaagc cctgcctcat gatccgagtt | 600 |
| gccaatatgc gcaaaagcct cctcattggc tgccaggtga caggaaaact gcttcagacc | 660 |
| caccaaacca aggaagggga gaacatccgg ctcaaccagg tcaatgtgac tttccaagta | 720 |
| gacacagcct ctgacagccc cttccttatt ctaccccta ccttctatca tgtggtagat | 780 |
| gagaccagtc ccttgaaaga tctccctctt cgcagtggtg agggtgactt tgagctggtg | 840 |
| ctgatcctaa gtgggacagt ggagtccacc agtgccacct gtcaggtgcg cacttcctac | 900 |
| ctgccagagg agatcctttg gggctacgag ttcacacctg ccatctcact gtcagccagt | 960 |
| ggtaaataca tagctgactt tagcctttttt gaccaagttg tgaaagtggc ctctcctagt | 1020 |
| ggcctccgtg acagcactgt acgctacgga gaccctgaaa agctcaagtt ggaggagtca | 1080 |
| ttaagggagc aagctgagaa ggagggcagt gcccttagtg tgcgcatcag caatgtctga | 1140 |

<210> SEQ ID NO 5
<211> LENGTH: 1140
<212> TYPE: DNA
<213> ORGANISM: Homo sapiens

<400> SEQUENCE: 5

| | |
|---|---|
| atgacgtcag ttgccaaggt gtattacagt cagaccactc agacagaaag ccggccccta | 60 |
| atgggcccag ggatacgacg gcggagagtc ctgacaaaag atggtcgcag caacgtgaga | 120 |
| atggagcaca ttgccgacaa gcgcttcctc tacctcaagg acctgtggac aaccttcatt | 180 |
| gacatgcagt ggcgctacaa gcttctgctc ttctctgcga cctttgcagg cacatggttc | 240 |
| ctctttggcg tggtgtggta tctggtagct gtggcacatg gggacctgct ggagctggac | 300 |
| cccccggcca accacacccc ctgtgtggta caggtgcaca cactcactgg agccttcctc | 360 |
| ttctcccttg aatcccaaac caccattggc tatggcttcc gctacatcag tgaggaatgt | 420 |
| ccactggcca ttgtgcttct tattgcccag ctggtgctca ccaccatcct ggaaatcttc | 480 |
| atcacaggta tcttcctggc gaagattgcc cggcccaaga agcgggctga gaccattcgt | 540 |
| ttcagccagc atgcagttgt ggcctcccac aatggcaagc cctgcctcat gatccgagtt | 600 |
| gccaatatgc gcaaaagcct cctcattggc tgccaggtga caggaaaact gcttcagacc | 660 |
| caccaaacca aggaagggga gaacatccgg ctcaaccagg tcaatgtgac tttccaagta | 720 |
| gacacagcct ctgacagccc cttccttatt ctaccccta ccttctatca tgtggtagat | 780 |
| gagaccagtc ccttgaaaga tctccctctt cgcagtggtg agggtgactt tgagctggtg | 840 |
| ctgatcctaa gtgggacagt ggagtccacc agtgccacct gtcaggtgcg cacttcctac | 900 |
| ctgccagagg agatcctttg gggctacgag ttcacacctg ccatctcact gtcagccagt | 960 |
| ggtaaataca tagctgactt tagcctttttt gaccaagttg tgaaagtggc ctctcctagt | 1020 |
| ggcctccgtg acagcactgt acgctacgga gaccctgaaa agctcaagtt ggaggagtca | 1080 |
| ttaagggagc aagctgagaa ggagggcagt gcccttagtg tgcgcatcag caatgtctga | 1140 |

<210> SEQ ID NO 6
<211> LENGTH: 1140
<212> TYPE: DNA
<213> ORGANISM: Homo sapiens

<400> SEQUENCE: 6

| | |
|---|---|
| atgacgtcag ttgccaaggt gtattacagt cagaccactc agacagaaag ccggccccta | 60 |
| atgggcccag ggatacgacg gcggagagtc ctgacaaaag atggtcgcag caacgtgaga | 120 |

| | |
|---|---|
| atggagcaca ttgccgacaa gcgcttcctc tacctcaagg acctgtggac aaccttcatt | 180 |
| gacatgcagt ggcgctacaa gcttctgctc ttctctgcga cctttgcagg cacatggttc | 240 |
| ctctttggcg tggtgtggta tctggtagct gtggcacatg gggacctgct ggagctggac | 300 |
| cccccggcca accacacccc ctgtgtggta caggtgcaca cactcactgg agccttcctc | 360 |
| ttctcccttg aatcccaaac caccattggc tatggcttcc gctacatcag tgaggaatgt | 420 |
| ccactggcca ttgtgcttct tattgcccag ctggtgctca ccaccatcct ggaaatcttc | 480 |
| atcacaggta tcttcctggc gaagattgcc cggcccaaga agcgggctga gaccattcgt | 540 |
| ttcagccagc atgcagttgt ggcctccac aatggcaagc cctgcctcat gatccgagtt | 600 |
| gccaatatgc gcaaaagcct cctcattggc tgccaggtga caggaaaaact gcttcagacc | 660 |
| caccaaaacca aggaagggga gaacatccgg ctcaaccagg tcaatgtgac tttccaagta | 720 |
| gacacagcct ctgacagccc cttccttatt ctaccccta ccttctatca tgtggtagat | 780 |
| gagaccagtc ccttgaaaga tctccctctt cgcagtggtg agggtgactt tgagctggtg | 840 |
| ctgatcctaa gtgggacagt ggagtccacc agtgccacct gtcaggtgcg cacttcctac | 900 |
| ctgccagagg agatcctttg gggctacgag ttcacacctg ccatctcact gtcagccagt | 960 |
| ggtaaataca tagctgactt tagccttttt gaccaagttg tgaaagtggc ctctcctagt | 1020 |
| ggcctccgtg acagcactgt acgctacgga gaccctgaaa agctcaagtt ggaggagtca | 1080 |
| ttaagggagc aagctgagaa ggagggcagt gcccttagtg tgcgcatcag caatgtctga | 1140 |

<210> SEQ ID NO 7
<211> LENGTH: 1140
<212> TYPE: DNA
<213> ORGANISM: Homo sapiens

<400> SEQUENCE: 7

| | |
|---|---|
| atgacgtcag ttgccaaggt gtattacagt cagaccactc agacagaaag ccggccccta | 60 |
| atgggcccag ggatacgacg gcggagagtc ctgacaaaag atggtcgcag caacgtgaga | 120 |
| atggagcaca ttgccgacaa gcgcttcctc tacctcaagg acctgtggac aaccttcatt | 180 |
| gacatgcagt ggcgctacaa gcttctgctc ttctctgcga cctttgcagg cacatggttc | 240 |
| ctctttggcg tggtgtggta tctggtagct gtggcacatg gggacctgct ggagctggac | 300 |
| cccccggcca accacacccc ctgtgtggta caggtgcaca cactcactgg agccttcctc | 360 |
| ttctcccttg aatcccaaac caccattggc tatggcttcc gctacatcag tgaggaatgt | 420 |
| ccactggcca ttgtgcttct tattgcccag ctggtgctca ccaccatcct ggaaatcttc | 480 |
| atcacaggta ccttcctggc gaagattgcc cggcccaaga agcgggctga gaccattcgt | 540 |
| ttcagccagc atgcagttgt ggcctccac aatggcaagc cctgcctcat gatctgagtt | 600 |
| gccaatatgc gcaaaagcct cctcattggc tgccaggtga caggaaaaact gcttcagacc | 660 |
| caccaaaacca aggaagggga gaacatccgg ctcaaccagg tcaatgtgac tttccaagta | 720 |
| gacacagcct ctgacagccc cttccttatt ctaccccta ccttctatca tgtggtagat | 780 |
| gagaccagtc ccttgaaaga tctccctctt cgcagtggtg agggtgactt tgagctggtg | 840 |
| ctgatcctaa gtgggacagt ggagtccacc agtgccacct gtcaggtgcg cacttcctac | 900 |
| ctgccagagg agatcctttg gggctacgag ttcacacctg ccatctcact gtcagccagt | 960 |
| ggtaaataca tagctgactt tagccttttt gaccaagttg tgaaagtggc ctctcctagt | 1020 |
| ggcctccgtg acagcactgt acgctacgga gaccctgaaa agctcaagtt ggaggagtca | 1080 |
| ttaagggagc aagctgagaa ggagggcagt gcccttagtg tgcgcatcag caatgtctga | 1140 |

<210> SEQ ID NO 8
<211> LENGTH: 1140
<212> TYPE: DNA
<213> ORGANISM: Homo sapiens

<400> SEQUENCE: 8

```
atgacgtcag ttgccaaggt gtattacagt cagaccactc agacagaaag ccggccccta      60
atgggcccag ggatacgacg gcggagagtc ctgacaaaag atggtcgcag caacgtgaga     120
atggagcaca ttgccgacaa agcttcctc tacctcaagg acctgtggac aaccttcatt      180
gacatgcagt ggcgctacaa agcttctgctc ttctctgcga ccttttgcagg cacatggttc    240
ctctttggcg tggtgtggta tctggtagct gtggcacatg ggacctgct ggagctggac      300
cccccggcca accacacccc ctgtgtggta caggtgcaca cactcactgg agccttcctc     360
ttctcccttg aatcccaaac caccattggc tatggcttcc gctacatcag tgaggaatgt    420
ccactggcca ttgtgcttct tattgcccag ctggtgctca ccaccatcct ggaaatcttc    480
atcacaggta cctcctggc gaagattgcc cggcccaaga gcgggctga accattcgt       540
ttcagccagc atgcagttgt ggcctcccac aatggcaagc cctgcctcat gatccgagtt    600
gccaatatgc gcaaaagcct cctcattggc tgccaggtga caggaaaact gcttcagacc    660
caccaaaacca aggaagggga aacatccgg ctcaaccagg tcaatgtgac tttccaagta    720
gacacagcct ctgacagccc cttccttatt ctacccctta ccttctatca tgtggtagat    780
gagaccagtc ccttgaaaga tctccctctt cgcagtggtg agggtgactt tgagctggtg    840
ctgatcctaa gtgggacagt ggagtccacc agtgccacct gtcaggtgtg cacttcctac    900
ctgccagagg agatcctttg gggctacgag ttcacacctg ccatctcact gtcagccagt    960
ggtaaataca tagctgactt tagcctttttt gaccaagttg tgaaagtggc ctctcctagt   1020
ggcctccgtg acagcactgt acgctacgga gaccctgaaa agctcaagtt ggaggagtca   1080
ttaagggagc aagctgagaa ggagggcagt gcccttagtg tgcgcatcag caatgtctga   1140
```

<210> SEQ ID NO 9
<211> LENGTH: 379
<212> TYPE: PRT
<213> ORGANISM: Homo sapiens

<400> SEQUENCE: 9

```
Met Thr Ser Val Ala Lys Val Tyr Tyr Ser Gln Thr Thr Gln Thr Glu
1               5                   10                  15

Ser Arg Pro Leu Met Gly Pro Gly Ile Arg Arg Arg Val Leu Thr
            20                  25                  30

Lys Asp Gly Arg Ser Asn Val Arg Met Glu His Ile Ala Asp Lys Arg
        35                  40                  45

Phe Leu Tyr Leu Lys Asp Leu Trp Thr Thr Phe Ile Asp Met Gln Trp
    50                  55                  60

Pro Tyr Lys Leu Leu Leu Phe Ser Ala Thr Phe Ala Gly Thr Trp Phe
65                  70                  75                  80

Leu Phe Gly Val Val Trp Tyr Leu Val Ala Val Ala His Gly Asp Leu
                85                  90                  95

Leu Glu Leu Asp Pro Pro Ala Asn His Thr Pro Cys Val Val Gln Val
            100                 105                 110

His Thr Leu Thr Gly Ala Phe Leu Phe Ser Leu Glu Ser Gln Thr Thr
        115                 120                 125

Ile Gly Tyr Gly Phe Arg Tyr Ile Ser Glu Glu Cys Pro Leu Ala Ile
    130                 135                 140
```

```
Val Leu Leu Ile Ala Gln Leu Val Leu Thr Thr Ile Leu Glu Ile Phe
145                 150                 155                 160

Ile Thr Gly Thr Phe Leu Ala Lys Ile Ala Arg Pro Lys Lys Arg Ala
            165                 170                 175

Glu Thr Ile Arg Phe Ser Gln His Ala Val Val Ala Ser His Asn Gly
            180                 185                 190

Lys Pro Cys Leu Met Ile Arg Val Ala Asn Met Arg Lys Ser Leu Leu
            195                 200                 205

Ile Gly Cys Gln Val Thr Gly Lys Leu Leu Gln Thr His Gln Thr Lys
210                 215                 220

Glu Gly Glu Asn Ile Arg Leu Asn Gln Val Asn Val Thr Phe Gln Val
225                 230                 235                 240

Asp Thr Ala Ser Asp Ser Pro Phe Leu Ile Leu Pro Leu Thr Phe Tyr
            245                 250                 255

His Val Val Asp Glu Thr Ser Pro Leu Lys Asp Leu Pro Leu Arg Ser
            260                 265                 270

Gly Glu Gly Asp Phe Glu Leu Val Leu Ile Leu Ser Gly Thr Val Glu
            275                 280                 285

Ser Thr Ser Ala Thr Cys Gln Val Arg Thr Ser Tyr Leu Pro Glu Glu
290                 295                 300

Ile Leu Trp Gly Tyr Glu Phe Thr Pro Ala Ile Ser Leu Ser Ala Ser
305                 310                 315                 320

Gly Lys Tyr Ile Ala Asp Phe Ser Leu Phe Asp Gln Val Val Lys Val
            325                 330                 335

Ala Ser Pro Ser Gly Leu Arg Asp Ser Thr Val Arg Tyr Gly Asp Pro
            340                 345                 350

Glu Lys Leu Lys Leu Glu Glu Ser Leu Arg Glu Gln Ala Glu Lys Glu
            355                 360                 365

Gly Ser Ala Leu Ser Val Arg Ile Ser Asn Val
            370                 375

<210> SEQ ID NO 10
<211> LENGTH: 379
<212> TYPE: PRT
<213> ORGANISM: Homo sapiens

<400> SEQUENCE: 10

Met Thr Ser Val Ala Lys Val Tyr Tyr Ser Gln Thr Thr Gln Thr Glu
1               5                   10                  15

Ser Arg Pro Leu Met Gly Pro Gly Ile Arg Arg Arg Val Leu Thr
            20                  25                  30

Lys Asp Gly Arg Ser Asn Val Arg Met Glu His Ile Ala Asp Lys Arg
            35                  40                  45

Phe Leu Tyr Leu Lys Asp Leu Trp Thr Thr Phe Ile Asp Met Gln Trp
    50                  55                  60

Arg Tyr Lys Leu Leu Leu Phe Ser Ala Thr Phe Ala Gly Thr Trp Phe
65                  70                  75                  80

Leu Phe Gly Val Val Trp Tyr Leu Val Ala Val Ala His Gly Asp Leu
                85                  90                  95

Leu Glu Leu Asp Pro Pro Ala Asn His Thr Pro Cys Val Gln Val
            100                 105                 110

His Thr Leu Thr Gly Ala Phe Leu Phe Ser Leu Glu Ser Gln Thr Thr
            115                 120                 125

Ile Gly Tyr Gly Phe Arg Tyr Ile Ser Glu Glu Arg Pro Leu Ala Ile
130                 135                 140
```

```
Val Leu Leu Ile Ala Gln Leu Val Leu Thr Thr Ile Leu Glu Ile Phe
145                 150                 155                 160

Ile Thr Gly Thr Phe Leu Ala Lys Ile Ala Arg Pro Lys Lys Arg Ala
                165                 170                 175

Glu Thr Ile Arg Phe Ser Gln His Ala Val Val Ala Ser His Asn Gly
            180                 185                 190

Lys Pro Cys Leu Met Ile Arg Val Ala Asn Met Arg Lys Ser Leu Leu
        195                 200                 205

Ile Gly Cys Gln Val Thr Gly Lys Leu Leu Gln Thr His Gln Thr Lys
    210                 215                 220

Glu Gly Glu Asn Ile Arg Leu Asn Gln Val Asn Val Thr Phe Gln Val
225                 230                 235                 240

Asp Thr Ala Ser Asp Ser Pro Phe Leu Ile Leu Pro Leu Thr Phe Tyr
                245                 250                 255

His Val Val Asp Glu Thr Ser Pro Leu Lys Asp Leu Pro Leu Arg Ser
            260                 265                 270

Gly Glu Gly Asp Phe Glu Leu Val Leu Ile Leu Ser Gly Thr Val Glu
        275                 280                 285

Ser Thr Ser Ala Thr Cys Gln Val Arg Thr Ser Tyr Leu Pro Glu Glu
    290                 295                 300

Ile Leu Trp Gly Tyr Glu Phe Thr Pro Ala Ile Ser Leu Ser Ala Ser
305                 310                 315                 320

Gly Lys Tyr Ile Ala Asp Phe Ser Leu Phe Asp Gln Val Val Lys Val
                325                 330                 335

Ala Ser Pro Ser Gly Leu Arg Asp Ser Thr Val Arg Tyr Gly Asp Pro
            340                 345                 350

Glu Lys Leu Lys Leu Glu Glu Ser Leu Arg Glu Gln Ala Glu Lys Glu
        355                 360                 365

Gly Ser Ala Leu Ser Val Arg Ile Ser Asn Val
    370                 375

<210> SEQ ID NO 11
<211> LENGTH: 379
<212> TYPE: PRT
<213> ORGANISM: Homo sapiens

<400> SEQUENCE: 11

Met Thr Ser Val Ala Lys Val Tyr Tyr Ser Gln Thr Thr Gln Thr Glu
1               5                   10                  15

Ser Arg Pro Leu Met Gly Pro Gly Ile Arg Arg Arg Val Leu Thr
                20                  25                  30

Lys Asp Gly Arg Ser Asn Val Arg Met Glu His Ile Ala Asp Lys Arg
            35                  40                  45

Phe Leu Tyr Leu Lys Asp Leu Trp Thr Thr Phe Ile Asp Met Gln Trp
        50                  55                  60

Arg Tyr Lys Leu Leu Phe Ser Ala Thr Phe Ala Gly Thr Trp Phe
65                  70                  75                  80

Leu Phe Gly Val Val Trp Tyr Leu Val Ala Val Ala His Gly Asp Leu
                85                  90                  95

Leu Glu Leu Asp Pro Pro Ala Asn His Thr Pro Cys Val Gln Val
            100                 105                 110

His Thr Leu Thr Gly Ala Phe Leu Phe Ser Leu Glu Ser Gln Thr Thr
        115                 120                 125

Ile Gly Tyr Gly Phe Arg Tyr Ile Ser Glu Glu Cys Pro Leu Ala Ile
130                 135                 140
```

Val Leu Leu Ile Ala Gln Leu Val Leu Thr Thr Ile Leu Glu Ile Phe
145                 150                 155                 160

Ile Thr Gly Ile Phe Leu Ala Lys Ile Ala Arg Pro Lys Lys Arg Ala
                165                 170                 175

Glu Thr Ile Arg Phe Ser Gln His Ala Val Val Ala Ser His Asn Gly
                180                 185                 190

Lys Pro Cys Leu Met Ile Arg Val Ala Asn Met Arg Lys Ser Leu Leu
                195                 200                 205

Ile Gly Cys Gln Val Thr Gly Lys Leu Leu Gln Thr His Gln Thr Lys
            210                 215                 220

Glu Gly Glu Asn Ile Arg Leu Asn Gln Val Asn Val Thr Phe Gln Val
225                 230                 235                 240

Asp Thr Ala Ser Asp Ser Pro Phe Leu Ile Leu Pro Leu Thr Phe Tyr
                245                 250                 255

His Val Val Asp Glu Thr Ser Pro Leu Lys Asp Leu Pro Leu Arg Ser
                260                 265                 270

Gly Glu Gly Asp Phe Glu Leu Val Leu Ile Leu Ser Gly Thr Val Glu
            275                 280                 285

Ser Thr Ser Ala Thr Cys Gln Val Arg Thr Ser Tyr Leu Pro Glu Glu
290                 295                 300

Ile Leu Trp Gly Tyr Glu Phe Thr Pro Ala Ile Ser Leu Ser Ala Ser
305                 310                 315                 320

Gly Lys Tyr Ile Ala Asp Phe Ser Leu Phe Asp Gln Val Val Lys Val
                325                 330                 335

Ala Ser Pro Ser Gly Leu Arg Asp Ser Thr Val Arg Tyr Gly Asp Pro
                340                 345                 350

Glu Lys Leu Lys Leu Glu Glu Ser Leu Arg Glu Gln Ala Glu Lys Glu
                355                 360                 365

Gly Ser Ala Leu Ser Val Arg Ile Ser Asn Val
            370                 375

<210> SEQ ID NO 12
<211> LENGTH: 379
<212> TYPE: PRT
<213> ORGANISM: Homo sapiens

<400> SEQUENCE: 12

Met Thr Ser Val Ala Lys Val Tyr Tyr Ser Gln Thr Thr Gln Thr Glu
1               5                   10                  15

Ser Arg Pro Leu Met Gly Pro Gly Ile Arg Arg Arg Val Leu Thr
                20                  25                  30

Lys Asp Gly Arg Ser Asn Val Arg Met Glu His Ile Ala Asp Lys Arg
            35                  40                  45

Phe Leu Tyr Leu Lys Asp Leu Trp Thr Thr Phe Ile Asp Met Gln Trp
        50                  55                  60

Arg Tyr Lys Leu Leu Leu Phe Ser Ala Thr Phe Ala Gly Thr Trp Phe
65                  70                  75                  80

Leu Phe Gly Val Val Trp Tyr Leu Val Ala Val Ala His Gly Asp Leu
                85                  90                  95

Leu Glu Leu Asp Pro Pro Ala Asn His Thr Pro Cys Val Gln Val
                100                 105                 110

His Thr Leu Thr Gly Ala Phe Leu Phe Ser Leu Glu Ser Gln Thr Thr
            115                 120                 125

Ile Gly Tyr Gly Phe Arg Tyr Ile Ser Glu Glu Cys Pro Leu Ala Ile
        130                 135                 140

Val Leu Leu Ile Ala Gln Leu Val Leu Thr Thr Ile Leu Glu Ile Phe
145                 150                 155                 160

Ile Thr Gly Thr Phe Leu Val Lys Ile Ala Arg Pro Lys Lys Arg Ala
                165                 170                 175

Glu Thr Ile Arg Phe Ser Gln His Ala Val Val Ala Ser His Asn Gly
            180                 185                 190

Lys Pro Cys Leu Met Ile Arg Val Ala Asn Met Arg Lys Ser Leu Leu
        195                 200                 205

Ile Gly Cys Gln Val Thr Gly Lys Leu Leu Gln His Gln Thr Lys
    210                 215                 220

Glu Gly Glu Asn Ile Arg Leu Asn Gln Val Asn Val Thr Phe Gln Val
225                 230                 235                 240

Asp Thr Ala Ser Asp Ser Pro Phe Leu Ile Leu Pro Leu Thr Phe Tyr
                245                 250                 255

His Val Val Asp Glu Thr Ser Pro Leu Lys Asp Leu Pro Leu Arg Ser
            260                 265                 270

Gly Glu Gly Asp Phe Glu Leu Val Leu Ile Leu Ser Gly Thr Val Glu
        275                 280                 285

Ser Thr Ser Ala Thr Cys Gln Val Arg Thr Ser Tyr Leu Pro Glu Glu
290                 295                 300

Ile Leu Trp Gly Tyr Glu Phe Thr Pro Ala Ile Ser Leu Ser Ala Ser
305                 310                 315                 320

Gly Lys Tyr Ile Ala Asp Phe Ser Leu Phe Asp Gln Val Val Lys Val
                325                 330                 335

Ala Ser Pro Ser Gly Leu Arg Asp Ser Thr Val Arg Tyr Gly Asp Pro
            340                 345                 350

Glu Lys Leu Lys Leu Glu Glu Ser Leu Arg Glu Gln Ala Glu Lys Glu
        355                 360                 365

Gly Ser Ala Leu Ser Val Arg Ile Ser Asn Val
    370                 375

<210> SEQ ID NO 13
<211> LENGTH: 199
<212> TYPE: PRT
<213> ORGANISM: Homo sapiens

<400> SEQUENCE: 13

Met Thr Ser Val Ala Lys Val Tyr Tyr Ser Gln Thr Thr Gln Thr Glu
1               5                   10                  15

Ser Arg Pro Leu Met Gly Pro Gly Ile Arg Arg Arg Val Leu Thr
                20                  25                  30

Lys Asp Gly Arg Ser Asn Val Arg Met Glu His Ile Ala Asp Lys Arg
            35                  40                  45

Phe Leu Tyr Leu Lys Asp Leu Trp Thr Thr Phe Ile Asp Met Gln Trp
        50                  55                  60

Arg Tyr Lys Leu Leu Phe Ser Ala Thr Phe Ala Gly Thr Trp Phe
65                  70                  75                  80

Leu Phe Gly Val Val Trp Tyr Leu Val Ala Val Ala His Gly Asp Leu
                85                  90                  95

Leu Glu Leu Asp Pro Pro Ala Asn His Thr Pro Cys Val Gln Val
            100                 105                 110

His Thr Leu Thr Gly Ala Phe Leu Phe Ser Leu Glu Ser Gln Thr Thr
        115                 120                 125

Ile Gly Tyr Gly Phe Arg Tyr Ile Ser Glu Glu Cys Pro Leu Ala Ile
    130                 135                 140

```
Val Leu Leu Ile Ala Gln Leu Val Leu Thr Thr Ile Leu Glu Ile Phe
145                 150                 155                 160

Ile Thr Gly Thr Phe Leu Ala Lys Ile Ala Arg Pro Lys Lys Arg Ala
                165                 170                 175

Glu Thr Ile Arg Phe Ser Gln His Ala Val Val Ala Ser His Asn Gly
            180                 185                 190

Lys Pro Cys Leu Met Ile Arg
            195

<210> SEQ ID NO 14
<211> LENGTH: 379
<212> TYPE: PRT
<213> ORGANISM: Homo sapiens

<400> SEQUENCE: 14

Met Thr Ser Val Ala Lys Val Tyr Tyr Ser Gln Thr Thr Gln Thr Glu
1               5                   10                  15

Ser Arg Pro Leu Met Gly Pro Gly Ile Arg Arg Arg Val Leu Thr
            20                  25                  30

Lys Asp Gly Arg Ser Asn Val Arg Met Glu His Ile Ala Asp Lys Arg
        35                  40                  45

Phe Leu Tyr Leu Lys Asp Leu Trp Thr Thr Phe Ile Asp Met Gln Trp
    50                  55                  60

Arg Tyr Lys Leu Leu Phe Ser Ala Thr Phe Ala Gly Thr Trp Phe
65                  70                  75                  80

Leu Phe Gly Val Val Trp Tyr Leu Val Ala Val Ala His Gly Asp Leu
                85                  90                  95

Leu Glu Leu Asp Pro Pro Ala Asn His Thr Pro Cys Val Val Gln Val
            100                 105                 110

His Thr Leu Thr Gly Ala Phe Leu Phe Ser Leu Glu Ser Gln Thr Thr
        115                 120                 125

Ile Gly Tyr Gly Phe Arg Tyr Ile Ser Glu Glu Cys Pro Leu Ala Ile
    130                 135                 140

Val Leu Leu Ile Ala Gln Leu Val Leu Thr Thr Ile Leu Glu Ile Phe
145                 150                 155                 160

Ile Thr Gly Thr Phe Leu Ala Lys Ile Ala Arg Pro Lys Lys Arg Ala
                165                 170                 175

Glu Thr Ile Arg Phe Ser Gln His Ala Val Val Ala Ser His Asn Gly
            180                 185                 190

Lys Pro Cys Leu Met Ile Arg Val Ala Asn Met Arg Lys Ser Leu Leu
        195                 200                 205

Ile Gly Cys Gln Val Thr Gly Lys Leu Leu Gln Thr His Gln Thr Lys
    210                 215                 220

Glu Gly Glu Asn Ile Arg Leu Asn Gln Val Asn Val Thr Phe Gln Val
225                 230                 235                 240

Asp Thr Ala Ser Asp Ser Pro Phe Leu Ile Leu Pro Leu Thr Phe Tyr
                245                 250                 255

His Val Val Asp Glu Thr Ser Pro Leu Lys Asp Leu Pro Leu Arg Ser
            260                 265                 270

Gly Glu Gly Asp Phe Glu Leu Val Leu Ile Leu Ser Gly Thr Val Glu
        275                 280                 285

Ser Thr Ser Ala Thr Cys Gln Val Cys Thr Ser Tyr Leu Pro Glu Glu
    290                 295                 300

Ile Leu Trp Gly Tyr Glu Phe Thr Pro Ala Ile Ser Leu Ser Ala Ser
305                 310                 315                 320
```

Gly Lys Tyr Ile Ala Asp Phe Ser Leu Phe Asp Gln Val Val Lys Val
            325                 330                 335

Ala Ser Pro Ser Gly Leu Arg Asp Ser Thr Val Arg Tyr Gly Asp Pro
        340                 345                 350

Glu Lys Leu Lys Leu Glu Glu Ser Leu Arg Glu Gln Ala Glu Lys Glu
    355                 360                 365

Gly Ser Ala Leu Ser Val Arg Ile Ser Asn Val
    370                 375

<210> SEQ ID NO 15
<211> LENGTH: 12
<212> TYPE: PRT
<213> ORGANISM: Artificial Sequence
<220> FEATURE:
<223> OTHER INFORMATION: chemically synthesized

<400> SEQUENCE: 15

Cys Met His Ile Glu Ser Leu Asp Ser Tyr Thr Cys
1               5                   10

<210> SEQ ID NO 16
<211> LENGTH: 10
<212> TYPE: PRT
<213> ORGANISM: Artificial Sequence
<220> FEATURE:
<223> OTHER INFORMATION: chemically synthesized

<400> SEQUENCE: 16

Cys Asp Pro Gly Tyr Ile Gly Ser Arg Cys
1               5                   10

<210> SEQ ID NO 17
<211> LENGTH: 20
<212> TYPE: DNA
<213> ORGANISM: Artificial Sequence
<220> FEATURE:
<223> OTHER INFORMATION: chemically synthesized

<400> SEQUENCE: 17
catggggtga gggttaggag                                              20

<210> SEQ ID NO 18
<211> LENGTH: 18
<212> TYPE: DNA
<213> ORGANISM: Artificial Sequence
<220> FEATURE:
<223> OTHER INFORMATION: chemically synthesized

<400> SEQUENCE: 18
gggagtggag gatgggtg                                                18

<210> SEQ ID NO 19
<211> LENGTH: 21
<212> TYPE: DNA
<213> ORGANISM: Artificial Sequence
<220> FEATURE:
<223> OTHER INFORMATION: chemically synthesized

<400> SEQUENCE: 19
cgggctgaga ccattcgttt c                                            21

<210> SEQ ID NO 20
<211> LENGTH: 22
<212> TYPE: DNA
<213> ORGANISM: Artificial Sequence

```
<220> FEATURE:
<223> OTHER INFORMATION: chemically synthesized

<400> SEQUENCE: 20
aggcttttgc gcatattgga ac                                              22
```